United States Patent
Figueiredo et al.

(10) Patent No.: US 9,877,923 B2
(45) Date of Patent: Jan. 30, 2018

(54) PROCESS FOR PREPARING THERAPEUTIC NANOPARTICLES

(71) Applicant: Pfizer Inc., New York, NY (US)

(72) Inventors: Maria Figueiredo, Somerville, MA (US); Erick Peeke, Somerville, MA (US); David Dewitt, Allston, MA (US); Christina Van Geen Hoven, Cambridge, MA (US); Greg Troiano, Pembroke, MA (US); James Wright, Lexington, MA (US); Young-Ho Song, Natick, MA (US); Hong Wang, Newton, MA (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 14/027,696

(22) Filed: Sep. 16, 2013

(65) Prior Publication Data

US 2014/0186452 A1 Jul. 3, 2014

Related U.S. Application Data

(60) Provisional application No. 61/702,037, filed on Sep. 17, 2012.

(51) Int. Cl.
| | |
|---|---|
| A61K 9/14 | (2006.01) |
| A61K 47/12 | (2006.01) |
| A61K 31/047 | (2006.01) |
| A61K 31/13 | (2006.01) |
| A61K 9/16 | (2006.01) |
| A61K 9/51 | (2006.01) |
| A61K 31/506 | (2006.01) |

(52) U.S. Cl.
CPC .......... *A61K 9/1682* (2013.01); *A61K 9/1617* (2013.01); *A61K 9/1647* (2013.01); *A61K 9/5153* (2013.01); *A61K 31/506* (2013.01); *A61K 47/12* (2013.01)

(58) Field of Classification Search
None
See application file for complete search history.

(56) References Cited

U.S. PATENT DOCUMENTS

| | | | |
|---|---|---|---|
| 5,302,401 A | 4/1994 | Liversidge et al. | |
| 5,543,158 A | 8/1996 | Gref et al. | |
| 5,563,122 A | 10/1996 | Endo et al. | |
| 5,578,325 A | 11/1996 | Domb et al. | |
| 5,766,635 A | 6/1998 | Spenleuhauer et al. | |
| 6,007,845 A | 12/1999 | Domb et al. | |
| 6,136,846 A | 10/2000 | Rubinfeld et al. | |
| 6,139,870 A | 10/2000 | Verrecchia | |
| 6,201,072 B1 | 3/2001 | Rathi et al. | |
| 6,254,890 B1 | 7/2001 | Hirosue et al. | |
| 6,265,609 B1 | 7/2001 | Jackson et al. | |
| 6,346,274 B1 | 2/2002 | Koll et al. | |
| 6,395,718 B1 | 5/2002 | Slusher et al. | |
| 6,528,499 B1 | 3/2003 | Kozikowski et al. | |
| 6,841,547 B2 | 1/2005 | Brown et al. | |
| 6,875,886 B2 | 4/2005 | Frangioni | |
| 6,890,946 B2 | 5/2005 | Nakshatri et al. | |
| 6,890,950 B2 | 5/2005 | Boothman et al. | |
| 6,899,898 B2 | 5/2005 | Albayrak | |
| 6,902,743 B1 | 6/2005 | Setterstrom et al. | |
| 6,916,788 B2 | 7/2005 | Seo et al. | |
| 7,422,902 B1 | 9/2008 | Wheeler et al. | |
| 7,687,071 B1 | 3/2010 | Heger et al. | |
| 7,772,274 B1 * | 8/2010 | Palepu ............... | A61K 9/0019 514/449 |
| 8,003,128 B2 | 8/2011 | Kreuter et al. | |
| 8,034,765 B2 | 10/2011 | De et al. | |
| 8,206,747 B2 | 6/2012 | Zale et al. | |
| 8,211,473 B2 | 7/2012 | Troiano et al. | |
| 8,236,330 B2 | 8/2012 | Zale et al. | |
| 8,246,968 B2 | 8/2012 | Zale et al. | |
| 8,273,363 B2 | 9/2012 | Zale et al. | |
| 8,293,276 B2 | 10/2012 | Troiano et al. | |
| 8,318,208 B1 | 11/2012 | Zale et al. | |
| 8,318,211 B2 | 11/2012 | Zale et al. | |
| 8,357,401 B2 | 1/2013 | Troiano et al. | |
| 8,420,123 B2 | 4/2013 | Troiano et al. | |
| 8,518,963 B2 | 8/2013 | Ali et al. | |
| 8,563,041 B2 | 10/2013 | Grayson et al. | |
| 8,603,534 B2 | 12/2013 | Zale et al. | |
| 8,603,535 B2 | 12/2013 | Troiano et al. | |
| 8,609,142 B2 | 12/2013 | Troiano et al. | |

(Continued)

FOREIGN PATENT DOCUMENTS

| | | |
|---|---|---|
| CN | 1957911 A | 5/2007 |
| CN | 1961864 A | 5/2007 |

(Continued)

OTHER PUBLICATIONS

Lee, S. et al., "Nano spray drying: A novel method of preparing protein nanoparticles for protein therapy," International Journal of Pharmaceutics 403 (2011) 192-200.*
Dong et al., "(Methoxy poly(ethylene glycol)-poly(lactide) (MPEG-PLA) nanoparticles for controlled delivery of anticancer drugs," (2004) Biomaterials. 25:2843-2849.
Dorati et al., "Polyethylenglycol-co-poly-D,L-lactide copolymer based microspheres: preparation, characterization and delivery of a model protein," *J Microencapsul.* (2008).
Extended European Search Report for EP 11835279.8 dated Feb. 28, 2014, 8 pages.
Extended European Search Report for EP 14150948.9 dated Jul. 8, 2014, 8 pages.

(Continued)

*Primary Examiner* — Tracy Vivlemore
*Assistant Examiner* — Monica A Shin
(74) *Attorney, Agent, or Firm* — Feng Shao

(57) ABSTRACT

The present disclosure generally relates to a process for preparing therapeutic nanoparticles, where the process includes combining a therapeutic agent with an organic acid. The therapeutic nanoparticles may have, for example, improved drug loading and/or drug release properties.

24 Claims, 5 Drawing Sheets

(56) References Cited

U.S. PATENT DOCUMENTS

| | | | |
|---|---|---|---|
| 8,613,951 B2 | 12/2013 | Zale et al. | |
| 8,613,954 B2 | 12/2013 | Zale et al. | |
| 8,617,608 B2 | 12/2013 | Zale et al. | |
| 8,623,417 B1 | 1/2014 | Zale et al. | |
| 8,637,083 B2 | 1/2014 | Troiano et al. | |
| 8,652,528 B2 | 2/2014 | Troiano et al. | |
| 8,663,700 B2 | 3/2014 | Troiano et al. | |
| 2002/0045582 A1 | 4/2002 | Margolin et al. | |
| 2002/0119916 A1 | 8/2002 | Hassan | |
| 2003/0068377 A1 | 4/2003 | Fowers et al. | |
| 2003/0143184 A1 | 7/2003 | Seo et al. | |
| 2003/0181530 A1* | 9/2003 | Ursin | A61K 47/20 514/651 |
| 2003/0232887 A1 | 12/2003 | Johnson et al. | |
| 2003/0235619 A1 | 12/2003 | Allen et al. | |
| 2004/0054190 A1 | 3/2004 | Pomper et al. | |
| 2004/0071768 A1 | 4/2004 | Sarris et al. | |
| 2004/0081688 A1 | 4/2004 | Del Curto et al. | |
| 2004/0086544 A1 | 5/2004 | Bezemer et al. | |
| 2004/0096477 A1 | 5/2004 | Chauhan et al. | |
| 2004/0185170 A1 | 9/2004 | Chungi et al. | |
| 2004/0219224 A1 | 11/2004 | Yakovlevsky et al. | |
| 2004/0220081 A1 | 11/2004 | Kreitz et al. | |
| 2004/0247624 A1 | 12/2004 | Unger et al. | |
| 2004/0247680 A1 | 12/2004 | Farokhzad et al. | |
| 2005/0037075 A1 | 2/2005 | Farokhzad et al. | |
| 2005/0037086 A1 | 2/2005 | Tyo et al. | |
| 2005/0063976 A1 | 3/2005 | Schultes et al. | |
| 2005/0123617 A1 | 6/2005 | Chang et al. | |
| 2005/0136258 A1 | 6/2005 | Nie et al. | |
| 2005/0142205 A1 | 6/2005 | Rashba-Step et al. | |
| 2005/0201972 A1 | 9/2005 | Seo et al. | |
| 2005/0256071 A1 | 11/2005 | Davis | |
| 2005/0266067 A1 | 12/2005 | Sengupta et al. | |
| 2006/0002852 A1 | 1/2006 | Saltzman et al. | |
| 2006/0002971 A1 | 1/2006 | Saltzman et al. | |
| 2006/0034925 A1 | 2/2006 | Au et al. | |
| 2006/0057219 A1 | 3/2006 | Nagasaki et al. | |
| 2006/0110460 A1 | 5/2006 | Ferret et al. | |
| 2006/0165987 A1 | 7/2006 | Hildgen et al. | |
| 2007/0031402 A1 | 2/2007 | Zhang et al. | |
| 2007/0041901 A1 | 2/2007 | Diener et al. | |
| 2007/0043066 A1 | 2/2007 | Sum et al. | |
| 2007/0053845 A1 | 3/2007 | Sengupta et al. | |
| 2007/0154554 A1 | 7/2007 | Burgermeister et al. | |
| 2008/0057102 A1 | 3/2008 | Roorda | |
| 2008/0081074 A1 | 4/2008 | Gu et al. | |
| 2008/0124400 A1 | 5/2008 | Liggins et al. | |
| 2008/0193381 A1 | 8/2008 | Babich et al. | |
| 2008/0267876 A1 | 10/2008 | Benita et al. | |
| 2009/0022806 A1 | 1/2009 | Mousa et al. | |
| 2009/0053293 A1 | 2/2009 | Liang et al. | |
| 2009/0053315 A1 | 2/2009 | Brough et al. | |
| 2009/0061009 A1 | 3/2009 | Schwarz et al. | |
| 2009/0074753 A1 | 3/2009 | Lynch | |
| 2009/0074828 A1 | 3/2009 | Alexis et al. | |
| 2009/0155326 A1 | 6/2009 | Mack et al. | |
| 2009/0155349 A1 | 6/2009 | Heller et al. | |
| 2009/0170753 A1 | 7/2009 | Welz et al. | |
| 2009/0196933 A1 | 8/2009 | De et al. | |
| 2009/0247552 A1 | 10/2009 | Sawa et al. | |
| 2009/0306120 A1 | 12/2009 | Lim et al. | |
| 2009/0312402 A1 | 12/2009 | Contag et al. | |
| 2009/0317479 A1 | 12/2009 | Ishihara et al. | |
| 2010/0008998 A1 | 1/2010 | Kang et al. | |
| 2010/0015050 A1 | 1/2010 | Panyam et al. | |
| 2010/0040537 A1 | 2/2010 | Gu et al. | |
| 2010/0068286 A1* | 3/2010 | Troiano | A61K 9/10 424/489 |
| 2010/0087337 A1 | 4/2010 | Dewitt | |
| 2010/0104645 A1 | 4/2010 | Ali et al. | |
| 2010/0166866 A1 | 7/2010 | Fischer et al. | |
| 2010/0216804 A1 | 8/2010 | Zale et al. | |
| 2010/0266491 A1 | 10/2010 | Farokhzad et al. | |
| 2010/0303723 A1 | 12/2010 | Farokhzad et al. | |
| 2010/0303900 A1 | 12/2010 | Ramstack et al. | |
| 2010/0316725 A1 | 12/2010 | Ryde et al. | |
| 2011/0125090 A1 | 5/2011 | Peyman | |
| 2011/0159079 A1 | 6/2011 | Li et al. | |
| 2011/0200677 A1 | 8/2011 | Chandran et al. | |
| 2011/0217377 A1 | 9/2011 | Zale et al. | |
| 2011/0275704 A1 | 11/2011 | Troiano et al. | |
| 2011/0294717 A1 | 12/2011 | Ali et al. | |
| 2012/0276162 A1 | 11/2012 | Zale et al. | |
| 2013/0034608 A1 | 2/2013 | Zale et al. | |
| 2013/0101672 A1 | 4/2013 | Cheng et al. | |
| 2013/0108668 A1 | 5/2013 | Figueiredo et al. | |
| 2013/0115293 A1 | 5/2013 | Sabnis et al. | |
| 2013/0172406 A1 | 7/2013 | Zale et al. | |
| 2013/0189315 A1 | 7/2013 | Zale et al. | |
| 2013/0230568 A1 | 9/2013 | Troiano et al. | |
| 2013/0236500 A1 | 9/2013 | Zale et al. | |
| 2013/0243827 A1 | 9/2013 | Troiano et al. | |
| 2013/0243863 A1 | 9/2013 | Troiano et al. | |
| 2013/0302433 A1 | 11/2013 | Troiano et al. | |
| 2014/0030351 A1 | 1/2014 | Zale et al. | |
| 2014/0093579 A1 | 4/2014 | Zale et al. | |
| 2014/0142165 A1 | 5/2014 | Grayson et al. | |
| 2014/0178475 A1 | 6/2014 | Figueiredo et al. | |
| 2014/0186452 A1 | 7/2014 | Figueiredo et al. | |
| 2014/0186453 A1 | 7/2014 | Zale et al. | |
| 2014/0248358 A1 | 9/2014 | Figueiredo et al. | |
| 2014/0249158 A1 | 9/2014 | Figueiredo et al. | |
| 2014/0308363 A1 | 10/2014 | Zale | |
| 2014/0356443 A1 | 12/2014 | Brisander et al. | |
| 2015/0056300 A1* | 2/2015 | Dewitt | A61K 9/0019 424/649 |

FOREIGN PATENT DOCUMENTS

| | | |
|---|---|---|
| CN | 1969816 A | 5/2007 |
| CN | 1969818 A | 5/2007 |
| CN | 101053553 A | 10/2007 |
| CN | 101396340 A | 4/2009 |
| CN | 101396342 A | 4/2009 |
| CN | 101433520 A | 5/2009 |
| EA | 011594 B1 | 12/2007 |
| EP | 0805678 A1 | 11/1997 |
| EP | 1985309 A1 | 10/2008 |
| EP | 2106806 A1 | 10/2009 |
| JP | H10-194995 A | 7/1998 |
| JP | 2006131577 A | 5/2006 |
| JP | 2006321763 A | 11/2006 |
| KR | 10-0418916 | 3/2002 |
| KR | 20020041712 A | 6/2002 |
| RU | 2007140909 A | 5/2009 |
| WO | WO-1989000846 A1 | 2/1989 |
| WO | WO-9428874 A1 | 12/1994 |
| WO | WO-95003357 A1 | 2/1995 |
| WO | WO-95035097 A1 | 12/1995 |
| WO | WO-97041837 A2 | 11/1997 |
| WO | WO-200000222 A1 | 1/2000 |
| WO | WO-00019996 A1 | 4/2000 |
| WO | WO-2001087345 A1 | 11/2001 |
| WO | WO-2002045689 A1 | 6/2002 |
| WO | WO-02080846 A2 | 10/2002 |
| WO | WO-2002098885 A1 | 12/2002 |
| WO | WO-03017987 A1 | 3/2003 |
| WO | WO-03032906 A2 | 4/2003 |
| WO | WO-2003055469 A1 | 7/2003 |
| WO | WO-2003086369 A2 | 10/2003 |
| WO | WO-2004060059 A2 | 7/2004 |
| WO | WO-2004084871 A1 | 10/2004 |
| WO | WO-2004089291 A2 | 10/2004 |
| WO | WO-2005009357 A2 | 2/2005 |
| WO | WO-2005020989 A1 | 3/2005 |
| WO | WO-2005046572 A2 | 5/2005 |
| WO | WO-2006093991 A1 | 9/2006 |
| WO | WO-2007024323 A2 | 3/2007 |
| WO | WO-2007028341 A1 | 3/2007 |
| WO | WO-2007034479 A2 | 3/2007 |
| WO | WO-2007074604 A1 | 7/2007 |
| WO | WO-2007110152 A2 | 10/2007 |
| WO | WO-2007133807 A2 | 11/2007 |

(56) References Cited

FOREIGN PATENT DOCUMENTS

| | | |
|---|---|---|
| WO | WO-2008016602 A2 | 2/2008 |
| WO | WO-2008019142 A2 | 2/2008 |
| WO | WO-2008058192 A2 | 5/2008 |
| WO | WO-2008105773 A2 | 9/2008 |
| WO | WO-2008109163 A1 | 9/2008 |
| WO | WO-2008121949 A1 | 10/2008 |
| WO | WO-2008124632 A1 | 10/2008 |
| WO | WO-2008124634 A1 | 10/2008 |
| WO | WO-2008124639 A2 | 10/2008 |
| WO | WO-2008139804 A1 | 11/2008 |
| WO | WO-20080151245 A1 | 12/2008 |
| WO | WO-200970302 A1 | 6/2009 |
| WO | WO-2009074274 A1 | 6/2009 |
| WO | WO-2009084801 A1 | 7/2009 |
| WO | WO-2009121631 A2 | 10/2009 |
| WO | WO-2010/005721 A2 | 1/2010 |
| WO | WO-201005721 A2 | 1/2010 |
| WO | WO-201005723 A2 | 1/2010 |
| WO | WO-201005725 A2 | 1/2010 |
| WO | WO-201005726 A2 | 1/2010 |
| WO | WO-2010068866 A2 | 6/2010 |
| WO | WO-2010075072 A2 | 7/2010 |
| WO | WO-2010114768 A1 | 10/2010 |
| WO | WO-2010114770 A1 | 10/2010 |
| WO | WO-2010117668 A1 | 10/2010 |
| WO | WO-2011072218 A2 | 6/2011 |
| WO | WO-2011079279 A2 | 6/2011 |
| WO | WO-2011084513 A2 | 7/2011 |
| WO | WO-2011084518 A2 | 7/2011 |
| WO | WO-2011084521 A2 | 7/2011 |
| WO | WO-2011119995 A2 | 9/2011 |
| WO | WO-2012040513 A1 | 3/2012 |
| WO | WO-2012054923 A2 | 4/2012 |
| WO | WO-2012166923 A2 | 12/2012 |
| WO | WO-2013044219 A1 | 3/2013 |
| WO | WO-2013127490 A1 | 9/2013 |
| WO | WO-2014043618 A1 | 3/2014 |
| WO | WO-2014043625 A1 | 3/2014 |

OTHER PUBLICATIONS

Farokhzad et al., "Nanoparticle-aptamer bioconjugates for cancer targeting," *Expert Opin Drug Deliv.* (2006) 3(3):311-24.
Govender et al., "PLGA nanoparticles prepared by nanoprecipitation: drug loading and release studies of a water soluble drug " *J Control Release.* (1999) 57(2):171-85.
Gross, "Oral pH-modified release budesonide for treatment of inflammatory bowel disease, collagenous and lymphocytic colitis," *Expert Opin Pharmacother.* (2008) 9(7):1257-1265.
Jenning et al., "Characterisation of a novel solid lipid nanoparticle carrier system based on binary mixtures of liquid and solid lipids," *Int J Pharm.* (2000) 199(2):167-77.
Lewis, "Hawley's Condensed Chemical Dictionary, 15th ed.," Wiley-Interscience (2007) entries for "acid," "base," "dissociation constant," "partition coefficient," and "pK," pp. 16, 127, 472, 947, and 998.
Okassa et al., "Optimization of iron oxide nanoparticles encapsulation within poly(d,l-lactide-co-glycolide) sub-micron particles," *Eur J Pharm Biopharm.* (2007) 67(1):31-8.
Ren et al., "Preparation and characterization of magnetic PLA-PEG composite nanoparticles for drug targeting," *Reactive & Functional Polymers.* (2006) 66:944-951.
Stolnik et al., "(Polylactide-poly(ethylene glycol) micellar-like particles as potential drug carriers: production, colloidal properties and biological performance," (2001) *Journal Drug Targeting.* 9:361-378.
Toxnet database "Chemical/Physical Properties" for "Oleic Acid," "Dodecanoic Acid," "Procaine," "Sunitinib," and "Vincristine," pp. 1-22.
van Vlerken and Amiji, "Multi-functional polymeric nanoparticles for tumour-targeted drug delivery," *Expert Opin Drug Deliv.* (2006) 3(2):205-16.

Yoo et al., "Protein-fatty acid complex for enhanced loading and stability within biodegradable nanoparticles," *J Pharm Sci.* (2001) 90(2):194-201.
"Docetaxel Dosage," [retrieved on Mar. 28, 2013] http://www.drugs.com/dosage/docetaxel.html.
"Taxotere Dosage," [retrieved on Mar. 28, 2013]. http://www.drugs.com/dosage/taxotere.html.
Abdelwahed et al., "Freeze-Drying of Nanoparticles: Formulation, Process and Storage Considerations," *Adv. Drug Deliv. Rev.* (2006) 58:1688-1713.
Abizaid et al., "Sirolimus-Eluting Stents Inhibits Neointimal Hyperplasia in Diabetic Patients," *Eur. Heart J.* (2006) 25:104-112.
Adams et al., "Amphiphilic Block Copolymers for Drug Delivery", *J. Pharm. Sci.* (2003) 92, 1343-1355.
Altmann (Epothilone B and its analogs—a new family of anticancer agents, *Mini Rev Med Chem.* (2003) 3(2):149-158; Abstract Only [retrieved from Bentham Science, <URL: http://www.eurekaselect.com/80911/artcile>], 1 page.
Altmann (Epothilone B and its analogs—a new family of anticancer agents, *Mini Rev Med Chem.* (2003) 3(2):149-158; Abstract Only [retrieved from PUBMED, < URL: http://www.ncbi.nlm.nih.gov/pubmed/12570848>]), 1 page.
Avgoustakis, "Pegylated poly(lactide) and poly(lactide-co-glycolide) nanoparticles: Preparation, properties and possible applications in drug delivery," *Current Drug Delivery.* (2004) 1(4):321-333.
Barinka et al., "Interactions Between Human Glutamate Carboxypeptidase II and Urea-Based Inhibitors: Structural Characterization," *J. Med. Chem.* (2008) 51:7737-7743.
Barinka et al., "Structural Insight into the Pharmacophore Pocket of Human Glutamate Carboxypeptidase II," *J. Med. Chem.* (2007) 50:3267-3273.
Bilati et al., "Nanoprecipitation Versus Emulsion-based Techniques for the Encapsulation of Proteins into Biodegradable Nanoparticles and Process-related Stability Issues," *PharmSciTech.* (2005) 6(4):E594-E604.
Blindt et al., "A Novel Drug-Eluting Stent Coated with an Integrin-Binding Cyclic Arg-Gly-Asp Peptide Inhibits Neointimal Hyperplasia by Recruiting Endothelial Progenitor Cells," *J. Amer. Coll. Cardiol.* (2006) 47(9):1786-1795.
Caliceti et al., "Effective Protein Release from PEG/PLA Nanoparticles Produced by Compressed Gas Anti-Solvent Precipitation Techniques," *Journal of Controlled Release.* (2004) 94:195-205.
Chandran, et al., "Characterization of a Targeted Nanoparticle Functionalized with a Urea-Based Inhibitor of Prostate-Specific Membrane Antigen (PSMA)," *Cancer Biol. Ther.* (2008) 7:4:1-9.
Chen et al., "Radiohalogenated Prostate-Specific Membrane Antigen (PSMA)-Based Ureas as Imaging Agents for Prostate Cancer," *J. Med. Chem.* (2008) 51(24):7933-7943.
Cheng et al., "Formulation of Functionalized PLGA-PEG Nanoparticles for in Vivo Targeted Drug Delivery," *Biomaterials.* (2008) 28:869-879.
Dancey et al., "Therapeutic Targets" mTOR and Related Pathways, *Cancer Biol. Ther.* (2006) 5:9: 1065-1073.
Davaran, "Preparation and in Vitro Evaluation of Linear and Star-Branched PLGA Nanoparticles for Insulin Delivery," *J. Bioact. Compat. Polym.* (2008) 23:115-131.
De Jaeghere et al., "Formulation and Lyoprotection of Poly(lactic acid-co-ethylene oxide) Nanoparticles: Influence on Physical Stability and in Vitro Cell Uptake," *Pharm. Res.* (1999) 16(6):859-866.
De Jaeghere et al., "Freeze-Drying and Lyopreservation of Diblock and Triblock Poly(Lactic Acid)-Poly(Ethylene Oxide) (PLA-PEO) Copolymer Nanoparticles " *Pharmaceutical Development and Technology.* (2000) 5(4):473-483.
Dong et al., "In vitro and in vivo evaluation of methoxy polyethylene glycol-polylactide (MPEG-PLA) nanoparticles for small-molecule drug chemotherapy," (2007) Biomaterials.
Eurasian Official Action for EA 201170040, dated Jun. 29, 2012.
Eurasian Official Action for EA 201170038, dated Aug. 12, 2013.
Eurasian Search Report for Application No. EA 201170039, dated Nov. 21, 2011.
Eurasian Search Report for Application No. EA 201100765, dated Aug. 2, 2013.

(56) References Cited

OTHER PUBLICATIONS

Eurasian Search Report for Application No. EA 201290497, dated Jan. 15, 2013.
Eurasian Search Report for Application No. EA201170038, dated Jul. 8, 2011.
European Examination Report for EP 09794913.5, dated Jul. 16, 2012.
Ewesuedo et al., "Chapter 1: Systemically Administrated Drugs." *Drug Delivery Systems in Cancer Therapy*. Ed. D.M. Brown. Totowa:Humana, 2003, pp. 3-14.
Extended European Search Report for Application No. 09835578.7, dated May 18, 2012.
Extended European Search Report for Application No. EP 09794913.5 dated Jul. 8, 2011.
Extended European Search Report for Application No. EP 09794915.0, dated Jan. 25, 2012.
Extended European Search Report for Application No. EP 10836748.3, dated Mar. 21, 2013.
Extended European Search Report for Application No. EP 11186037.5, dated Mar. 2, 2012.
Extended European Search Report for EP 09794913.5 dated Jul. 4, 2013, 9 pages.
Extended European Search Report for EP 09794917.6 dated Aug. 7, 2013, 8 pages.
Extended European Search Report for EP 10842554.7 dated Jul. 10, 2013, 9 pages.
Extended European Search Report for EP 10842556.2 dated Jul. 8, 2013, 9 pages.
Extended European Search Report for EP 10842557.0 dated Jul. 8, 2013, 11 pages.
Extended European Search Report for EP 13162786.1 dated Aug. 30, 2013, 7 pages.
Extended European Search Report for EP 13162789.5 dated Aug. 30, 2013, 7 pages.
Farokhzad et al., "Nanoparticle-Aptamer Bioconjugates: A New Approach for Targeting Prostate Cancer Cells," *Cancer Res.* (dated Nov. 1, 2004) 64:7668-7672.
Farokhzad et al., "Targeted Nanoparticle-Aptamer Bioconjugates for Cancer Chemotherapy In Vivo" *Proc. Natl. Acad. Sci. USA.* (2006) 103(16):6315-6320.
Feng et al., "Nanoparticles of Biodegradable Polymers for Clinical Administration of Paclitaxel," *Current Medicinal Chemistry.* (2004) 11:413-424.
Foss et al., "Radiolabeled Small-Molecule Ligands for Prostate-Specific Membrane Antigen: In Vivo Imaging in Experimental Models of Prostate Cancer," *Clin. Cancer Res.* (2005) 11(11): 4022-4028.
Foss, Poster Session: Novel Probes and Activation Strategies, Part 3, "Synthesis and Validation of a Novel Small-Molecule Fluorescent Probe for PSMA Expression in Human Tumor Neovasculature," 4th Annual Meeting for the Society for Molecular Imaging, (Sep. 7-10, 2005.).
Fournier et al., "Experimental Studies and Preliminary Clinical Trial of Vinorelbine-loaded Polymeric Bioresorbable Implants for the Local Treatment of Solid Tumors" *Cancer Research.* (1991) 51:5384-5391.
Galsky et al., "Cabazitaxel," *Nature Reviews.* (2010) 9:677-678.
Gao et al., "In Vivo Cancer Targeting and Imaging with Semiconductor Quantum Dots," *Nat. Biotechnol.* (2004) 22, 8: 969-976.
Gill et al., "Modulated Differential Scanning Calorimetry," *J. Thermal Analysis.* (1993) 40:931-939.
Govender et al., "Defining the Drug Incorporation Properties of PLA-PEG Nanoparticles," *Int. J. Pharm.* (2000) 199:95-110.
Gref et al., "Stealth' Corona-Core Nanoparticles Surface Modified by Polyethylene Glycol (PEG): Influences of the Corona (PEG Chaing Length and Surface Density) and of the Core Composition on Phagocytic Uptake and Plasma Protein Adsorption," *Colloids and Surfaces B: Biointerfaces.* (2000) 301-313.
Gref et al., "Biodegradable Long-Circulating Polymeric Nanospheres," *Science.* (1994).263:1600-1603.
Gref et al., "Development and Characterization of CyA-loaded Poly(lactic acid)-poly(ethylene glycol)PEG Micro- and Nanoparticles. Comparison with Conventional PLA Particulate Carriers." *Eur. J. Pharm. Biopharm.* (2001) 51:111-118.
Gu et al., "Precise Engineering of Targeted Nanoparticles by Using Self-Assembled . Biointegrated Block Copolymers" *Proc. Natl. Acad. Sci. USA.* (2008) 105:2586-2591.
Heald et al., "Poly(lactic acid)-Poly(ethylene oxide) (PLA-PEG) Nanoparticles: NMR Studies of the Central Solidlike PLA Core and the Liquid PEG Corona," *Langmuir.* (2002) 18:3669-3675.
Hederstrom et al., "Purification and Surface Modification of Polymeric Nanoparticles for Medical Applications" Master's Thesis. SINTEF Materials and Chemistry, Trondheim, Norway, Mar. 3, 2008.
Heldman et al., "Paclitaxel stent coating inhibits neointimal hyperplasia at 4 weeks in a porcine model of coronary restenosis," *Circulation.* (2001) 103:2289-2295.
Hrkach et al., "Preclinical Development and Clinical Translation of a PSMA-Targeted Docetaxel Nanoparticle with a Differentiated Pharmacological Profile," *Sci. Trans. Med.* (2012). 4:1-11.
Humblet et al., "An HPLC/Mass Spectrometry Platform for the Development of Multimodality Contrast Agents and Targeted Therapeutics: Prostate-Specific Membrane Antigen Small Molecule Derivatives," *Contrast Med. Mol. Imaging.* (2006) 1:196-211.
Humblet et al., "High-Affinity Near-Infrared Fluorescent Small-Molecule Contrast Agents for in Vivo Imaging of Prostate-Specific Membrane Antigen," *Mol. Imaging.* ( 2005) 4:448-462.
International Preliminary Report on Patentability for PCT/US2010/060575 dated Jun. 19, 2012, 11 pages.
International Search Report for Application No. PCT/US08/13158 dated Jan. 20, 2009 and dated Feb. 17, 2009.
International Search Report for Application No. PCT/US08/58873 dated Aug. 15, 2008 and dated Aug. 28, 2008.
International Search Report for Application No. PCT/US09/47513 dated Jan. 18, 2010 and dated Jan. 18, 2010.
International Search Report for Application No. PCT/US09/67672 dated Aug. 20, 2010 and dated Aug. 23, 2010.
International Search Report for Application No. PCT/US09/68028 dated Aug. 9, 2010 and dated Aug. 23, 2010.
International Search Report for Application No. PCT/US10/59879 dated Aug. 30, 2011 and dated Aug. 30, 2011.
International Search Report for Application No. PCT/US10/60564 dated Sep. 29, 2011 and dated Sep. 29, 2011.
International Search Report for Application No. PCT/US10/60570 dated Aug. 25, 2011 and dated Aug. 25, 2011.
International Search Report for Application No. PCT/US10/60575 dated Aug. 25, 2011 and dated Aug. 25, 2011.
International Search Report for Application No. PCT/US11/057498 dated May 9, 2012 and dated May 10, 2012.
International Search Report for Application No. PCT/US2012/040215 dated Nov. 16, 2012 and dated Nov. 16, 2012.
International Search Report for Application No. PCT/US2012/056891 dated Jan. 4, 2013 and dated Jan. 4, 2013.
International Search Report for Application No. PCT/US2013/059949, dated Jan. 2, 2014 and dated Jan. 2, 2014, 5 pages.
International Search Report for PCT/US09/47515 dated Jan. 18, 2010 and dated Jan. 19, 2010.
International Search Report for PCT/US09/47517 dated Feb. 23, 2010 and dated Mar. 2, 2010.
International Search Report for PCT/US09/47518 dated Mar. 5, 2010 and dated Mar. 5, 2010.
Jayaprakash et al., "Design and Synthesis of a PSMA Inhibitor-Doxorubicin Conjugate for Targeted Prostate Cancer Therapy," *ChemMedChem* 2006, 1, pp. 299-302.
Jeong et al., "Effect of cryoprotectants on the reconstitution of surfactant-free nanoparticles of (poly)DL-lacticle-co-glycolide)," *J. of Microencapsulation.* (2005) 22(6):593-601.
Jiang et al., "Preparation of PLA and PLGA Nanoparticles by Binary Organic Solvent Diffusion Method," *J. Cent. South Univ. Technol.* (2003) 10(3):202-206.
Kimura et al., "Local Delivery of Imatinib Mesylate (STI571)-Incorporated Nanoparticle Ex Vivo Suppresses Vein Graft Neointima Formation," *Cancer Res.* (2008) 118:S65-S70.

(56) References Cited

OTHER PUBLICATIONS

Koziara et al., "Blood Compatibility of Cetyl Alcohol/Polysorbate-Based Nanoparticles," Pharma. Res. (2005) 22(11):1821-1828.
Kozikowski et al., Design of Remarkably Simple, Yet Potent Urea-Based Inhibitors of Glutamate Carboxypeptidase II (NAALADase), J. Med. Chem. (2001) 44:298-301.
Kozikowski et al., "Synthesis of Urea-Based Inhibitors as Active Site Probes of Glutamate Carboxypeptidase II: Efficacy as Analgesic Agents," J. Med. Chem. (2004) 47:1729-1738.
Kwon, "Long Acting Porous Microparticle for Pulmonary Protein Delivery," Int. J. Pharm. (2007) 333:5-9.
Li et al., "Post-Operative Imatinib in Patients with Intermediate or High Risk Gastrointestinal Stromal Tumor," EJSO. (2011) 37:319-324.
Lyseng-Williamson et al., "Docetaxel A Review of its Use in Metastatic Breast Cancer," Drugs. (2005) 65(17):2513-16.
Majer et al., "Synthesis and Biological Evaluation of Thiol-Based Inhibitors of Glutamate Carboxypeptidase II: Discovery of an Orally Active GCP II Inhibitor," J. Med. Chem. (2003) 46:1989-1996.
Maresca et al., "A Series of Halogenated Heterodimeric Inhibitors of Prostate Specific Membrane Antigen (PSMA) as Radiolabeled Probes for Targeting Prostate Cancer " J. Med. Chem. (2009) 52(2):347-57.
Matsumoto et al., "Preparation of Nanoparticles consisted of poly(L-lactide)-poly(ethylene glycol)poly(L-lactide) and Their Evaluation In Vitro," International J. of Pharmaceutics. (1999) 185:93-101.
Mease et al., "N-[N-[(S)-1,3-Dicarboxypropyl] Carbamoyl]-4-[18F] Fluorobenzyl-L-Cysteine, [18F] DCFBC: A New Imaging Probe for Prostate Cancer" Clin. Cancer Res. (2008) 14(10):3036-3043.
Merck (Betamethasone, Merck Index (Knovel, copyright 2006, 2012)), 3 pages.
Misra et al., "Production of Multimeric Prostate-Specific Membrane Antigen Small-Molecule Radiotracers Using a Solid-Phase 99m Tc Preloading Strategy," J. Nuclear Med. (2007) 48(8):1379-1389.
Murugesan et al., "Pegylated Poly(lactide-co-glycolidel (PLGA) Nanoparticulate Delivery of Docetaxel: Synthesis of Diblock Copolymers, Optimization of Preparation Variables on Formulation Characteristics and in Vitro Release Studies." J. Biomed. Nanotechnol. (2007) 3:52-60.
Musumeci et al., "Lyoprotected Nanosphere Formulations for Paclitaxel Controlled Delivery." J. Nanosci. Nanotech. (2006) 6:3118-3125.
Musumeci et al., "PLA/PLGA Nanoparticles for Sustained Release of Docetaxel " Int. J. Pharm. (2006) 325:172-179.
Ojer, "Spray-Drying of Poly(anhydride) Nanoparticles for Drug/Antigen Delivery," J. Drug Del. Sci. Tech. (2010) 20(5):353-359.
Oliver et al., "Conformational and SAR Analysis of NAALADase and PSMA Inhibitors " Biorg. Med. Chem. (2003) 11:4455-4461.
Olivier, "Drug Transport to Brain with Targeted Nanoparticles," The Journal of the American Society for Experimental NeuroTherapeutics. (2005) 2:108-119.
Omelczuk et al., "The Influence of Polymer Glass Transition Temperature and Molecular Weight on Drug Release from Tablets Containing Poly(DL-lactic acid)." Pharm. Res. (1992) 9(1):26-32.
Peracchia et al., "PEG-coated nanospheres from amphiphilic diblock and multiblock copolymers: Investigation of their drug encapsulation and release characteristics," Journal of Controlled Release. (1996) 46:223-231.
Pomper, Martin G., Russell H. Morgan Department of Radiology and Radiological Science, Johns Hopkins University, "New Developments in Molecular Imaging of Prostate Cancer," Topical Symposium on: Advanced Molecular Imaging Techniques in the Detection, Diagnosis, Therapy, and Follow-up of Prostate Cancer, Palazzo Barberini, Rome, Dec. 6, 2005.

Pourcelle, "PCL-PEG-based Nanoparticles Grafted with GRGDS Peptide: Preparation and Surface Analysis by XPS " Biomacromolecules. (2007) 8:3977-3983.
Pulkkinen et al., "Three-Step Tumor Targeting of Paclitaxel Using Biotinylated PLA-PEG Nanoparticles and Avidin-Biotin Technology: Formulation Development and In Vitro Anticancer Activity", Eur. J. Pharm. Biopharm. (2008) 70:66-74.
Riley et al., "Colloidal Stability and Drug Incorporation Aspects of Micellar-like PLA-PEG Nanoparticles," Colloids Surf. B: Biointer. (1999) 16:147-59.
Sapra et al., "Ligand-Targeted Liposomal Anticancer Drugs," Prog. Lipid Res. (2003) 42:439-462.
Senthilkumar et al., "Long Circulating PEGylated Poly(D,L-lactide-co-glycolide) Nanoparticulate Delivery of Docetaxel to Solid Tumors," J. Drug Target. (2008) 424-435.
Sweetman, "Martindale: The Complete Drug Reference," 33rd ed., 2002, Pharmaceutical Press, entry for Docetaxel, p. 534.
Tamilvanan et al., "Manufacturing Techniques and Excipients Used During the Design of Biodegradable Polymer-Based Microspheres Containing Therapeutic Peptide/Protein for Parenteral Controlled Drug Delivery," J. Pharm. Sci. Tech. (2008) 62(2):125-154.
Tang, Hailun, et al., "Prostate Targeting Ligands Based on N-Acetylated α-Linked Acidic Dipeptidase," Biochem. Biophys. Res. Comm. 307 (2003), pp. 8-14.
Tobio et al., "Stealth PLA-PEG Nanoparticles as Protein Carriers for Nasal Administration," Pharm. Res. (1998) 15(2):270-275.
Verrecchia et al., "Non-stealth (poly(lactic acid/albumin) ) and stealth (poly(lactic acid-polyethylene glycol) ) nanoparticles as injectable drug carriers," J. of Controlled Release. (1995) 36:49-61.
Vicari et al., "Paclitaxel Loading in PLGA Nanospheres Affected the in Vitro Drug Cell Accumulation and Antiproliferative Activity," BMC Cancer. (2008) 8:212.
Yamamoto et al., "Long-Circulating Poly(ethylene glycol)-poly(D,L-lactide) block copolymer micelles with Modulated Surface Charge," Journal of Controlled Release. (2001) 77:27-38.
Zhang et al., "Neointimal Hyperplasia Persists at Six Months after Siroli Mus-Eluting Stent Implantation in Diabetic Porcine," Cardiovasc. Diabetol. (2007) 6:16:1-7.
Zhou et al., "NAAG Peptidase Inhibitors and Their Potential for Diagnosis and Therapy," Nature Rev. Drug Discov. (2005) 4:1015-1026.
International Search Report for Application No. PCT/US2013/059936, dated Feb. 4, 2014 and mailed Feb. 4, 2014, 8 pages.
U.S. Appl. No. 14/346,456, Methods of Treating Cancers With Therapeutic Nanoparticles, filed Mar. 21, 2014.
U.S. Appl. No. 14/276,461 Published as US 2014/0248358, Therapeutic Nanoparticles Comprising a Therapeutic Agent and Methods of Making and Using Same, filed May 13, 2014.
U.S. Appl. No. 14/276,490 Published as US 2014/0249158, Therapeutic Nanoparticles Comprising a Therapeutic Agent and Methods of Making and Using Same, filed May 13, 2014.
Balaram et al.; "Visibile spectrometric determination of imatinib mesylate in bulk drug and pharmaceutical formulations," Asian J. of Chemistry, vol. 21, No. 7, p. 5241-5244, published 2009.
Chio, Seung Ho, "Hydrophobic ion pair formation between leuprolide and sodium oleate for sustained release from biodegradable polymeric microspheres," 2000, Elsevier, Int. Journ. Of Pharm., vol. 203, pp. 193-202.
Clinical Trials, "A Study of BIND-014 Given to Patients with Advanced or Mestastatic Cancer," [retrieved on May 9, 2014] Retrived from the internet <URL: http://clinicaltrials.gov/archive/NCT01300533/2013_04_30>, 4 pages.
Faivre, Sandrie et al. "Molecular basis for sunitinib efficacy and future clinical development," 2007; Nature Publishing Group, Nature Reviews, vol. 6, pp. 734-745.
Green, "Facilitated transfer of cationic drugs across a lipoidal membrane by oleic acid and lauric acid," 1987, Elsevier; Int. J. of Pharm., vol. 37, pp. 251-255.
Gulati, Monica, "Lipophilic drug derivatives in liposomes" 1998 Elsevier, Int. J. of Pharm., vol. 165, pp. 129-168.
International Search Report and Written Opinion for Application No. PCT/US2014/044617, dated Oct. 3, 2014 and mailed Oct. 3, 2014, 13 pages.

(56) References Cited

OTHER PUBLICATIONS

Mackay, Donald Physical-Chemical Properties and Environmental Fate for Organic Chemicals, 2006, Taylor & Francis, Chapter 13, carboxylic acids, pp. 2688-2778.

Meyer, Jeffrey, D.; "Hydrophobic Ion Pairing: Altering the Solubility Properties of Biomolecules," 1998, Plenum; Pharmaceutical Research, vol. 15, No. 2, pp. 188-193.

Pinkerton "Formation of Stable Nanocarriers by in Situ Ion Pairing during Block Copolymer directed Rapid Precipitation," 2012, American Chemical Society, Molecular Pharmaceuticals.

Szasz, Gyorgy et al. "Ion-Pair Partition of Quaternary Ammonium Drugs: The influence of Counter ions of Different Lipophilicity, Size, and Flexibility," 1999, PLENUM, Pharm. Res. vol. 16, No. 10, pp. 1633-1638.

Amiji et al.; "Multi-functional polymeric nanoparticles for tumour-targeted drug delivery," 2006, Ashley Publications; Expert opinion on Drug Delivery, vol. 3, No. 2, pp. 205-216.

Song, et al.; "Transport of Organic Cation Drugs: Effect of Ion-Pair Formation with Bile Salts on the Biliary Excretion and Pharmacokinetics," 2013, Elsevier; Pharmacology & Therapeutics, vol. 138, pp. 142-154.

Dorati et al., "Polyethylenglycol-co-poly-D, L-lactide copolymer based microspheres: preparation, characterization and delivery of a model protein," J. Microencapsul. (2008) 25(5):330-338.

Gross, "Oral pH-modified release budesonide for treatment of inflammatory bowel disease, collagenous and lymphocyctic colitis," Expert Opin Pharmacother. (2008) 9(7): 1257-1265.

\* cited by examiner

– 1 –
PROCESS FOR PREPARING THERAPEUTIC NANOPARTICLES

REFERENCE TO RELATED APPLICATIONS

This application claims the benefit of and priority to U.S. Ser. No. 61/702,037, filed Sep. 17, 2012, which is hereby incorporated by reference in its entirety.

BACKGROUND

Systems that deliver certain drugs to a patient (e.g., targeted to a particular tissue or cell type or targeted to a specific diseased tissue but not normal tissue) or that control release of drugs have long been recognized as beneficial.

For example, therapeutics that include an active drug and that are, e.g., targeted to a particular tissue or cell type or targeted to a specific diseased tissue but not to normal tissue, may reduce the amount of the drug in tissues of the body that are not targeted. This is particularly important when treating a condition such as cancer where it is desirable that a cytotoxic dose of the drug is delivered to cancer cells without killing the surrounding non-cancerous tissue. Effective drug targeting may reduce the undesirable and sometimes life threatening side effects common in anticancer therapy. In addition, such therapeutics may allow drugs to reach certain tissues they would otherwise be unable to reach.

Therapeutics that offer controlled release and/or targeted therapy also must be able to deliver an effective amount of drug, which is a known limitation in other nanoparticle delivery systems. For example, it can be a challenge to prepare nanoparticle systems that have an appropriate amount of drug associated with each nanoparticle, while keeping the size of the nanoparticles small enough to have advantageous delivery properties. However, while it is desirable to load a nanoparticle with a high quantity of therapeutic agent, nanoparticle preparations that use a drug load that is too high will result in nanoparticles that are too large for practical therapeutic use.

Accordingly, a need exists for nanoparticle therapeutics and methods of making such nanoparticles that are capable of delivering therapeutic levels of drug to treat diseases such as cancer, while also reducing patient side effects.

SUMMARY

Described herein is a process for preparing therapeutic nanoparticles, where the process includes combining a therapeutic agent with an organic acid.

In one aspect, a method of preparing a plurality of therapeutic nanoparticles is provided. The method comprises combining a therapeutic agent, a first polymer, and an organic acid with an organic solvent to form a first organic phase having about 1 to about 50% solids, combining the first organic phase with a first aqueous solution to form the plurality of therapeutic nanoparticles, and recovering the therapeutic nanoparticles by filtration.

In some embodiments, the organic acid may have a $pK_a$ of less than about 3.5 at 25° C. In other embodiments, the organic acid may have a $pK_a$ of less than about 2.0 at 25° C. In still other embodiments, the organic acid may have a $pK_a$ of less than about 1 at 25° C. In further embodiments, the organic acid may have a $pK_a$ of less than about 0 at 25° C.

In some cases, the organic acid may have a boiling point of between about 50° C. and about 110° C. In some embodiments, the organic acid may have a melting point of between about −30° C. and about 0° C.

In some instances, the therapeutic nanoparticles may comprise about 0.2 to about 35 weight percent of the therapeutic agent. In other instances, the therapeutic nanoparticles may comprise about 1 to about 10 weight percent of the therapeutic agent.

In some embodiments, the method may be a first method and the therapeutic nanoparticles may have a therapeutic agent loading at least about 2 times higher as compared to therapeutic nanoparticles prepared by a second method, wherein the second method is identical to the first method except that the second method does not include the organic acid. In some cases, the therapeutic nanoparticles may have a therapeutic agent loading at least about 5 times higher. In other cases, the therapeutic nanoparticles may have a therapeutic agent loading at least about 10 times higher.

In some cases, the therapeutic agent may have a solubility in a first solution consisting of the therapeutic agent, the organic solvent, and the organic acid that is at least 5 times higher as compared to a second solution consisting of the therapeutic agent and the organic solvent. In other cases, the therapeutic agent may have a solubility in a first solution consisting of the therapeutic agent, the organic solvent, and the organic acid that is between about 2 to about 20 times higher as compared to a second solution consisting of the therapeutic agent and the organic solvent. In some embodiments, the concentration of the organic acid may be at least about 1 weight percent, at least about 2 weight percent, or at least about 3 weight percent. In other embodiments, the concentration of the organic acid may be between about 1 to about 10 weight percent.

In some embodiments, the organic acid may be a halogenated carboxylic acid. For example, the halogenated carboxylic acid may be trifluoroacetic acid.

In some instances, the therapeutic nanoparticles may substantially immediately release less than about 5% of the therapeutic agent when placed in a phosphate buffer solution at 37° C. In other instances, the therapeutic nanoparticles may release about 0.01 to about 25% of the therapeutic agent over about 1 hour when placed in a phosphate buffer solution at 37° C. In still other instances, the therapeutic nanoparticles may release about 10 to about 45% of the therapeutic agent over about 4 hours when placed in a phosphate buffer solution at 37° C.

In some embodiments, the therapeutic nanoparticles may have a diameter of about 60 nm to about 150 nm, about 80 nm to about 150 nm, or about 90 nm to about 140 nm.

In some cases, combining the first organic phase with the first aqueous solution may comprise emulsifying a second phase, formed from combining the first organic phase with the first aqueous solution, to form an emulsion phase.

In some embodiments, the method further comprises quenching the emulsion phase to form a quenched phase. For example, the method may further comprise adding a drug solubilizer to the quenched phase to form a solubilized phase of unencapsulated therapeutic agent.

In some cases, emulsifying the second phase may comprise emulsifying the second phase to form a coarse emulsion, and emulsifying the coarse emulsion to form a fine emulsion phase.

In certain embodiments, the organic solvent may comprise a solvent selected from the group consisting of ethyl acetate, benzyl alcohol, methylene chloride, chloroform, toluene, methyl ethyl ketone, dimethyl formamide, dimethyl sulfoxide, acetone, acetonitrile, acetic acid, Tween 80 and Span 80, and combinations of two or more thereof.

In some embodiments, the aqueous solution may comprise a reagent selected from the group consisting of sodium cholate, ethyl acetate, benzyl alcohol or combinations thereof.

Emulsifying the second phase may, in some embodiments, comprise using a rotor stator homogenizer, probe sonicator, stir bar, or high pressure homogenizer. In some cases, emulsifying the coarse emulsion may comprise using a high pressure homogenizer. In some embodiments, emulsifying the primary emulsion may comprise about 2 to about 3 passes through the homogenizer. In some instances, the homogenizer feed pressure may be about 2000 to about 8000 psi per interaction chamber. The homogenizer may, in some instances, comprise multiple interaction chambers.

In some embodiments, quenching may be at least partially performed at a temperature of about 5° C. or less. In other embodiments, quenching may be performed at about 0° C. to about 5° C.

In some cases, the quench:emulsion ratio may be about 2:1 to about 40:1 or about 5:1 to about 15:1.

In some embodiments, the drug solubilizer may be selected from the group consisting of Tween 80, Tween 20, polyvinyl pyrrolidone, cyclodextran, sodium dodecyl sulfate, and sodium cholate. In other embodiments, the drug solubilizer may be selected from the group consisting of diethylnitrosamine, sodium acetate, urea, glycerin, propylene glycol, glycofurol, poly(ethylene)glycol, bris(polyoxyethyleneglycolddodecyl ether, sodium benzoate, and sodium salicylate. The ratio of drug solubilizer to therapeutic agent may, in some embodiments, be about 200:1 to about 10:1.

In some instances, filtration may comprise tangential flow filtration. In some embodiments, filtration may comprise filtering at a first temperature of about 0° C. to about 5° C. In some cases, filtration may further comprise filtering at a second temperature of about 20° C. to about 30° C. Filtering may, in some embodiments, comprise processing about 1 to about 30 diavolumes at about 0° C. to about 5° C. and processing at least one diavolume at about 20° C. to about 30° C. In another example, filtering may comprise processing about 1 to about 30 diavolumes at about 0° C. to about 5° C. and processing about 1 to about 15 diavolumes at about 20° C. to about 30° C. In some instances, filtration may comprise processing different diavolumes at different distinct temperatures.

In some embodiments, the method may further comprise purifying the solubilized phase before the filtration to substantially remove the organic solvent, unencapsulated therapeutic agent, and/or drug solubilizer.

In some cases, filtration may comprise sterile filtration. For example, the sterile filtration may comprise filtering the therapeutic nanoparticles using a filtration train at a controlled rate. The filtration train may, in some instances, comprise a depth filter and a sterile filter.

In some embodiments, the first polymer may be a diblock poly(lactic) acid-poly(ethylene)glycol copolymer. In other embodiments, the first polymer may be a diblock poly(lactic)-co-poly(glycolic) acid-poly(ethylene)glycol copolymer. In some instances, the method further comprises combining a second polymer with the organic solvent, wherein the second polymer is a poly(lactic) acid-poly(ethylene) glycol copolymer functionalized with a targeting ligand. In some cases, the method further comprises combining a second polymer with the organic solvent, wherein the second polymer is a poly(lactic) acid-co-poly(glycolic) acid-poly(ethylene)glycol copolymer functionalized with a targeting ligand. The targeting ligand may, in some embodiments, be covalently bound to the poly(ethylene) glycol.

In certain embodiments, the organic acid comprises a mixture of two or more organic acids. For example, in some embodiments, the organic acid comprises a mixture of two organic acids, a mixture of three organic acids, a mixture of four organic acids, or a mixture of five organic acids.

In another aspect, a method of preparing a plurality of therapeutic nanoparticles is provided. The method comprises combining a therapeutic agent, a first polymer, and an organic acid, with an organic solvent to form a first organic phase having about 1 to about 50% solids, combining the first organic phase with a first aqueous solution to form a second phase, emulsifying the second phase to form an emulsion phase, quenching the emulsion phase to form a quenched phase, and filtering the solubilized phase to recover the therapeutic nanoparticles.

In yet another aspect, a therapeutic nanoparticle is provided. The therapeutic nanoparticle is prepared by emulsification of a first organic phase comprising a first polymer, a therapeutic agent, and an organic acid thereby forming an emulsion phase, quenching of the emulsion phase thereby forming a quenched phase, and filtration of the quenched phase to recover the therapeutic nanoparticles.

In still another aspect, a therapeutic nanoparticle is provided. The therapeutic nanoparticle comprises about 0.2 to about 35 weight percent of a Bcr-Abl tyrosine-kinase inhibitor, and about 50 to about 99.8 weight percent of a diblock poly(lactic) acid-poly(ethylene)glycol copolymer or a diblock poly(lactic)-co-poly(glycolic) acid-poly(ethylene) glycol copolymer, wherein the therapeutic nanoparticle comprises about 10 to about 30 weight percent poly(ethylene)glycol.

In some embodiments, the therapeutic nanoparticle may further comprise an organic acid having a $pK_a$ of less than about 3.5 at 25° C. In another embodiment, the organic acid may have a $pK_a$ of between about −1 and about 2 at 25° C.

In some cases, the organic acid may be trifluoroacetic acid.

In some embodiments, the hydrodynamic diameter of the therapeutic nanoparticle may be about 60 to about 150 nm. In another embodiment, the hydrodynamic diameter of the therapeutic nanoparticle may be about 90 to about 140 nm.

In some instances, the therapeutic nanoparticle may comprise about 1 to about 10 weight percent of the Bcr-Abl tyrosine-kinase inhibitor. In other instances, the therapeutic nanoparticle may comprise about 2 to about 5 weight percent of the Bcr-Abl tyrosine-kinase inhibitor.

In some embodiments, the therapeutic nanoparticle may substantially retain the Bcr-Abl tyrosine-kinase inhibitor for at least 1 minute when placed in a phosphate buffer solution at 37° C. In other embodiments, the therapeutic nanoparticle may substantially immediately release less than about 5% of the Bcr-Abl tyrosine-kinase inhibitor when placed in a phosphate buffer solution at 37° C. In further embodiments, the therapeutic nanoparticle may release about 0.01 to about 25% of the Bcr-Abl tyrosine-kinase inhibitor over about 1 hour when placed in a phosphate buffer solution at 37° C. In still other embodiments, the therapeutic nanoparticle may release about 10 to about 45% of the Bcr-Abl tyrosine-kinase inhibitor over about 4 hours when placed in a phosphate buffer solution at 37° C.

In some cases, the Bcr-Abl tyrosine-kinase inhibitor may be dasatinib or a pharmaceutically acceptable salt thereof. In other cases, the Bcr-Abl tyrosine-kinase inhibitor may be selected from the group consisting of imatinib, nilotinib, dasatinib, bosutinib, ponatinib, bafetinib, and pharmaceutically acceptable salts thereof.

In some embodiments, the therapeutic nanoparticle the poly(lactic) acid-poly(ethylene)glycol copolymer may have a poly(lactic) acid number average molecular weight fraction of about 0.6 to about 0.95, about 0.6 to about 0.8, about 0.75 to about 0.85, or about 0.7 to about 0.9.

In certain embodiments, the therapeutic nanoparticle may comprise about 10 to about 25 weight percent poly(ethylene)glycol, about 10 to about 20 weight percent poly(ethylene)glycol, about 15 to about 25 weight percent poly(ethylene)glycol, or about 20 to about 30 weight percent poly(ethylene)glycol.

In some cases, the therapeutic nanoparticle may further comprise about 0.2 to about 30 weight percent poly(lactic) acid-poly(ethylene)glycol copolymer functionalized with a targeting ligand. In some embodiments, the therapeutic nanoparticle may further comprise about 0.2 to about 30 weight percent poly(lactic) acid-co-poly(glycolic) acid-poly(ethylene)glycol copolymer functionalized with a targeting ligand. The targeting ligand may be covalently bound to the poly(ethylene)glycol.

In another aspect, a therapeutic nanoparticle is provided. The therapeutic nanoparticle comprises about 0.5 to about 35 weight percent of dasatinib or a pharmaceutically acceptable salt thereof, about 30 to about 99.5 weight percent poly(lactic) acid-poly(ethylene)glycol copolymer or poly(lactic)-co-poly(glycolic) acid-poly(ethylene)glycol copolymer, and optionally about 0.0001 to about 0.5 weight percent of an organic acid having a $pK_a$ of less than about 3.5 at 25° C., wherein the therapeutic nanoparticle comprises about 10 to about 25 weight percent poly(ethylene)glycol.

In certain embodiments, a contemplated therapeutic nanoparticle further comprises a mixture of two or more organic acids. For example, in some embodiments, a contemplated therapeutic nanoparticle comprises a mixture of two organic acids, a mixture of three organic acids, a mixture of four organic acids, or a mixture of five organic acids.

In yet another aspect, a therapeutic nanoparticle is provided. The therapeutic nanoparticle is prepared by emulsification of a first organic phase comprising a first polymer, a Bcr-Abl tyrosine-kinase inhibitor, and an organic acid having a $pK_a$ of less than about 3.5 at 25° C. thereby forming an emulsion phase, quenching of the emulsion phase thereby forming a quenched phase, and filtration of the quenched phase to recover the therapeutic nanoparticles.

In still another aspect, a pharmaceutically acceptable composition is provided. The pharmaceutically acceptable composition may comprise a plurality of therapeutic nanoparticles as described herein and a pharmaceutically acceptable excipient.

In some embodiments, the pharmaceutically acceptable composition may further comprise a saccharide. In some instances, the saccharide may be a disaccharide selected from the group consisting of sucrose or trehalose, or a mixture thereof. In another embodiment, the pharmaceutically acceptable composition may further comprise a cyclodextrin. In some cases, the cyclodextrin may be selected from the group consisting of α-cyclodextrin, β-cyclodextrin, γ-cyclodextrin, and mixtures thereof.

In yet another aspect, a method of treating cancer in a patient in need thereof is provided. The method comprises administering to the patient a therapeutically effective amount of a composition comprising a therapeutic nanoparticle as described herein. In some embodiments, the cancer may be chronic myelogenous leukemia. In other embodiments, the cancer may be selected from the group consisting of chronic myelomonocytic leukemia, hypereosinophilic syndrome, renal cell carcinoma, hepatocellular carcinoma, Philadelphia chromosome positive acute lymphoblastic leukemia, non-small cell lung cancer, pancreatic cancer, breast cancer, a solid tumor, and mantle cell lymphoma.

In still another aspect, a method of treating a gastrointestinal stromal tumor in a patient in need thereof is provided. The method comprises administering to the patient a therapeutically effective amount of a composition comprising a therapeutic nanoparticle as described herein.

In another aspect, there is provided a therapeutic nanoparticle as described herein for use as a medicament in a warm-blooded animal such as man.

In yet another aspect, there is provided a therapeutic nanoparticle as described herein for use in the production of an anti-proliferative effect in a warm-blooded animal such as man.

In still another aspect, there is provided a therapeutic nanoparticle as described herein for use in a warm-blooded animal such as man as an anti-invasive agent in the containment and/or treatment of solid tumor disease.

In yet another aspect, there is provided the use of a therapeutic nanoparticle as described herein in the prevention or treatment of cancer in a warm blooded animal such as man.

In still another aspect, there is provided a therapeutic nanoparticle as described herein for use in the prevention or treatment of cancer in a warm blooded animal such as man.

In yet another aspect, there is provided the use of a therapeutic nanoparticle as described herein in the manufacture of a medicament for the prevention or treatment of cancer in a warm blooded animal such as man.

In still another aspect, there is provided the use of a therapeutic nanoparticle as described herein for the production of an anti-proliferative effect in a warm-blooded animal such as man.

In yet another aspect, there is provided the use of a therapeutic nanoparticle as described herein in the manufacture of a medicament for use in the production of an anti-proliferative effect in a warm-blooded animal such as man.

In still another aspect, there is provided the use of a therapeutic nanoparticle as described herein in the manufacture of a medicament for use in a warm-blooded animal such as man as an anti-invasive agent in the containment and/or treatment of solid tumor disease.

In yet another aspect, there is provided a method for producing an anti-proliferative effect in a warm blooded animal, such as man, in need of such treatment which comprises administering to said animal an effective amount of a therapeutic nanoparticle as described herein.

In still another aspect, there is provided a method for producing an anti-invasive effect by the containment and/or treatment of solid tumor disease in a warm blooded animal, such as man, in need of such treatment which comprises administering to said animal an effective amount of a therapeutic nanoparticle as described herein.

In yet another aspect, there is provided a therapeutic nanoparticle as described herein for use in the prevention or treatment of solid tumor disease in a warm blooded animal such as man.

In still another aspect, there is provided the use of a therapeutic nanoparticle as described herein in the manufacture of a medicament for use in the prevention or treatment of solid tumor disease in a warm blooded animal such as man.

In yet another aspect, there is provided a method for the prevention or treatment of solid tumor disease in a warm blooded animal, such as man, in need of such treatment which comprises administering to said animal an effective amount of a therapeutic nanoparticle as described herein.

DETAILED DESCRIPTION

Figure 1:
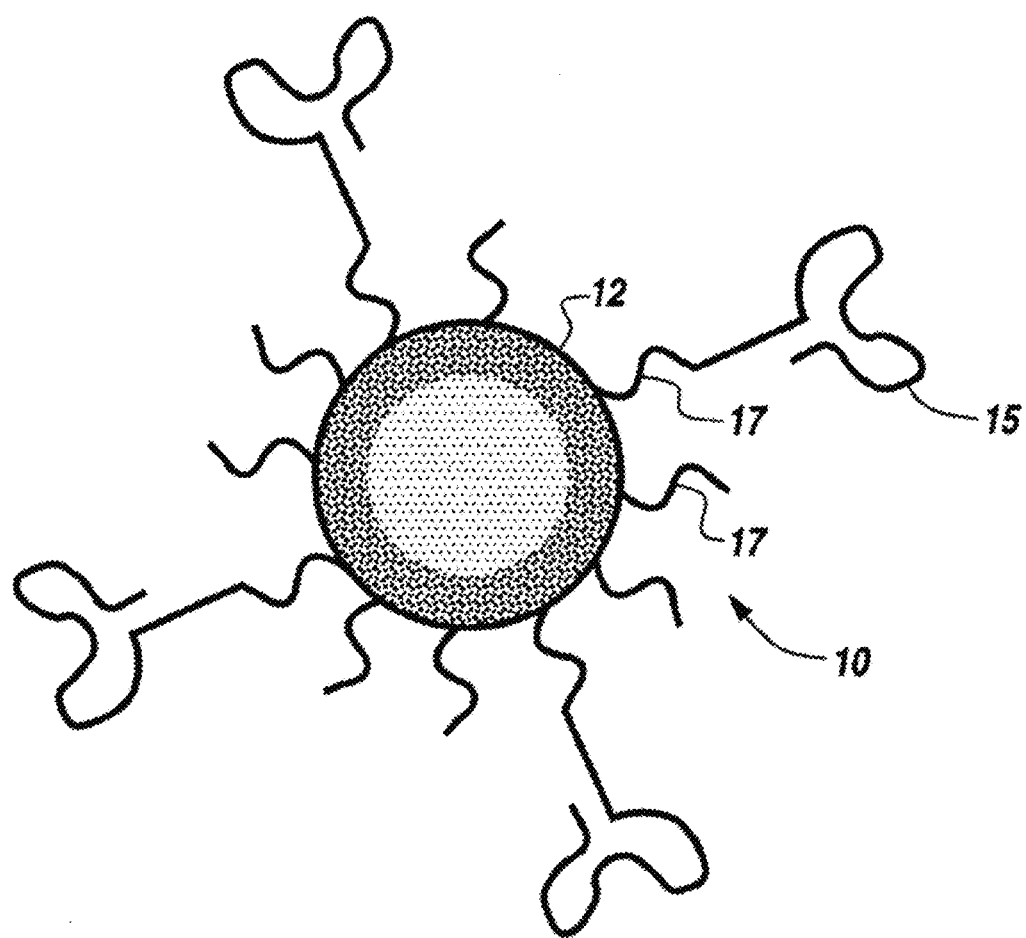
FIG. 1 depicts a pictorial representation of one embodiment of a disclosed nanoparticle.

Described herein is a process for preparing therapeutic nanoparticles, where the process includes combining a therapeutic agent with an organic acid. In some embodiments, inclusion of an organic acid in a nanoparticle preparation process may result in nanoparticles containing a substantially high loading of a therapeutic agent. Furthermore, in certain embodiments, nanoparticles that include or are prepared in the presence of the organic acid may exhibit improved controlled release properties. For example, the disclosed nanoparticles may more slowly release the therapeutic agent as compared to nanoparticles prepared in the absence of the organic acid. Also described herein are therapeutic nanoparticles prepared by the disclosed process.

As one of ordinary skill in the art will appreciate, nanoparticle formulations of some therapeutic agents prove more problematic than for other therapeutic agents. For example, attempting to prepare nanoparticles containing a problematic therapeutic agent can result in nanoparticles with insufficient drug loading, poorly controlled release properties, particles that are too large, etc. Surprisingly, it has been discovered that including an acid (e.g., trifluoroacetic acid) in a process for preparing therapeutic nanoparticles can improve the properties of the resultant therapeutic nanoparticles. As discussed above, in some embodiments, use of an acid in a disclosed process may confer advantageous properties to therapeutic nanoparticles prepared by the process, such as, e.g., improved drug loading and/or controlled release properties. Without wishing to be bound by any theory, it is believed that the acid confers advantageous properties to disclosed nanoparticles by improving the solubility of the therapeutic agent in solvents used in the preparation of the therapeutic nanoparticles.

Any suitable acid may be used in a nanoparticle preparation process. In some embodiments, the acid may be an organic acid. For example, a contemplated acid may be a carboxylic acid (e.g., a monocarboxylic acid, dicarboxylic acid, tricarboxylic acid, or the like), a sulfinic acid, a sulfenic acid, or a sulfonic acid. In some cases, a contemplated acid may include a mixture of two or more acids. For example, in some embodiments, a contemplated acid may comprise a mixture of two acids, in some embodiments a mixture of three acids, in some embodiments a mixture of four acids, or in some embodiments a mixture of five acids. In certain embodiments, an ester of an acid may be used. In some cases, a salt of an acid may be used. In some embodiments, the acid may be an inorganic acid. Exemplary inorganic acids include hydrochloric acid, nitric acid, phosphoric acid, sulfuric acid, boric acid, hydrofluoric acid, and hydrobromic acid.

For example, a disclosed carboxylic acid may be an aliphatic carboxylic acid (e.g., a carboxylic acid having a cyclic or acyclic, branched or unbranched, hydrocarbon chain). Disclosed carboxylic acids may, in some embodiments, be substituted with one or more functional groups including, but not limited to, halogen (i.e., F, Cl, Br, and I), sulfonyl, nitro, and oxo. For example, the carboxylic acid may be a halogenated carboxylic acid (e.g., trifluoroacetic acid). In certain embodiments, a disclosed carboxylic acid may be unsubstituted.

Exemplary carboxylic acids may include a substituted or unsubstituted fatty acid (e.g., $C_8$-$C_{50}$ fatty acid). In some instances, the fatty acid may be a $C_{10}$-$C_{20}$ fatty acid. In other instances, the fatty acid may be a $C_{15}$-$C_{20}$ fatty acid. The fatty acid may, in some cases, be saturated. In other embodiments, the fatty acid may be unsaturated. For instance, the fatty acid may be a monounsaturated fatty acid or a polyunsaturated fatty acid. In some embodiments, a double bond of an unsaturated fatty acid group can be in the cis conformation. In some embodiments, a double bond of an unsaturated fatty acid can be in the trans conformation Non-limiting examples of carboxylic acids include formic acid, acetic acid, propionic acid, butyric acid, valeric acid, caproic acid, heptanoic acid, caprylic acid, nonanoic acid, capric acid, undecanoic acid, lauric acid, tridecanoic acid, myristic acid, pentadecanoic acid, palmitic acid, heptadecanoic acid, stearic acid, nonadecanoic acid, arachidic acid, heneicosanoic acid, behenic acid, tricosanoic acid, lignoceric acid, pentacosanoic acid, cerotic acid, heptacosanoic acid, montanic acid, nonacosanoic acid, melissic acid, henatriacontanoic acid, lacceroic acid, psyllic acid, geddic acid, ceroplastic acid, hexatriacontanoic acid, 2-methylpropionic acid, 2-methylbutyric acid, 3-methylbutyric acid, 2-methylpentanoic acid, 2-ethylhexanoic acid, 2-propylheptanoic acid, pivalic acid, palmitoleic acid, oleic acid, vaccenic acid, linoleic acid, alpha-linolenic acid, gamma-linoleic acid, arachidonic, gadoleic acid, eicosapentaenoic acid, docosahexaenoic acid, erucic acid, cyclohexanecarboxylic acid, acrylic acid, methacrylic acid, crotonic acid, cinnamic acid, phenylacetic acid, oxalic acid, malonic acid, succinic acid, glutaric acid, adipic acid, maleic acid, malic acid, tartaric acid (e.g., dextotartaric, mesotartaric acid, etc.), citric acid, gluconic acid, aspartic acid, glutaminic acid, fumaric acid, itaconic acid, halogenated carboxylic acids such as fluoroacetic acid, difluoroacetic acid, trifluoroacetic acid, chloroacetic acid, dichloroacetic acid, and trichloroacetic acid, sulfonic acids such as triflic acid, methanesulfonic acid, benzenesulfonic acid, and p-toluenesulfonic acid, and combinations thereof.

In some instances, a contemplated acid may have a molecular weight of less than about 1000 Da, in some embodiments less than about 500 Da, in some embodiments less than about 400 Da, in some embodiments less than about 300 Da, in some embodiments less than about 250 Da, in some embodiments less than about 200 Da, in some embodiments less than about 150 Da, in some embodiments less than about 100 Da, in some embodiments less than about 90 Da, in some embodiments less than about 85 Da and in some embodiments less than about 75 Da. In some cases, the acid may have a molecular weight of between about 40 Da and about 1000 Da, in some embodiments between about 91 Da and about 1000 Da, in some embodiments between about 95 Da and about 1000 Da, in some embodiments between about 100 Da and about 1000 Da, in some embodiments between about 91 Da and about 150 Da, in some embodiments between about 95 Da and about 150 Da, and in some embodiments between about 100 Da and about 150 Da.

In some embodiments, an acid may be chosen, at least in part, on the basis of the strength of the acid. For example, the acid may have an acid dissociation constant in water ($pK_a$) of about −15 to about 7, in some embodiments about −3 to about 5, in some embodiments about −3 to about 4, in some embodiments about −3 to about 3.5, in some embodiments about −3 to about 3, in some embodiments about −3 to about 2, in some embodiments about −3 to about 1, in some embodiments about −3 to about 0.5, in some embodiments about −0.5 to about 0.5, in some embodiments about 1 to about 7, in some embodiments about 2 to about 7, in some embodiments about 3 to about 7, in some embodiments about 4 to about 6, in some embodiments about 4 to about 5.5, in some embodiments about 4 to about 5, and in some embodiments about 4.5 to about 5, determined at 25° C. In some embodiments, the acid may have a $pK_a$ of less than about 7, less than about 5, less than about 3.5, less than about 3, less than about 2, less than about 1, or less than about 0, determined at 25° C.

In some embodiments, a contemplated acid may have a phase transition temperature that is advantageous, for example, for improving the properties of the therapeutic nanoparticles or for reducing the concentration (e.g., by vacuum) of the acid in the final therapeutic nanoparticles. For instance, the acid may have a boiling point of less than about 300° C. or in some cases less than about 100° C. In certain embodiments, the acid may have a boiling point of between about 50° C. and about 110° C. or in some cases between about 60° C. and about 90° C. In some cases, the acid may have a melting point of less than about 15° C., in some cases less than about 10° C., or in some cases less than about 0° C. In certain embodiments, the acid may have a melting point of between about −30° C. and about 0° C. or in some cases between about −20° C. and about −10° C.

For example, an acid for use in methods nanoparticles disclosed herein may be chosen, at least in part, on the basis of the solubility of the therapeutic agent in a solvent comprising the acid. For example, in some embodiments, a therapeutic agent dissolved in a solvent comprising the acid may have a solubility of between about 15 mg/mL to about 200 mg/mL, between about 20 mg/mL to about 200 mg/mL, between about 25 mg/mL to about 200 mg/mL, between about 50 mg/mL to about 200 mg/mL, between about 75 mg/mL to about 200 mg/mL, between about 100 mg/mL to about 200 mg/mL, or between about 125 mg/mL to about 175 mg/mL. In some embodiments, a therapeutic agent dissolved in a solvent comprising the acid may have a solubility greater than about 50 mg/mL or greater than about 100 mg/mL. In some embodiments, a therapeutic agent dissolved in a solvent comprising the acid (e.g., a first solution consisting of the therapeutic agent, solvent, and acid) may have a solubility of at least about 2 times greater, in some embodiments at least about 5 times greater, in some embodiments at least about 10 times greater, in some embodiments at least about 20 times greater, in some embodiments about 2 times to about 20 times greater, or in some embodiments about 10 times to about 20 times greater than when the therapeutic agent is dissolved in a solvent that does not contain the acid (e.g., a second solution consisting of the therapeutic agent and the solvent). As discussed in more detail below, the concentration of acid in a drug solution may be between about 1% and about 10%, or in some embodiments between about 2.5% and about 3.5%.

As discussed in more detail below, in some instances, the concentration of acid in a drug solution (i.e., a therapeutic agent solution) may be between about 1 weight percent and about 10 weight percent, or in some embodiments between about 2.5 weight percent and about 3.5 weight percent. In certain embodiments, the concentration of acid in a drug solution may be at least about 1 weight percent, in some embodiments at least about 2 weight percent, in some embodiments at least about 3 weight percent, in some embodiments at least about 10 weight percent.

In some cases, a solution containing the therapeutic agent may be prepared separately from a solution containing the polymer, and the two solutions may then be combined prior to nanoparticle formulation. For instance, in one embodiment, a first solution contains the therapeutic agent and the acid, and a second solution contains the polymer and optionally the acid. Formulations where the second solution does not contain the acid may be advantageous, for example, for minimizing the amount of acid used in a process or, in some cases, for minimizing contact time between the acid and, e.g., a polymer that can degrade in the presence of the acid. In other cases, a single solution may be prepared containing the therapeutic agent, polymer, and acid.

In certain embodiments, the acid may have a solubility of at least about 100 mg per 100 mL of water, at least about 1 g per 100 mL of water, at least about 10 g per 100 mL of water, or at least about 50 g per 100 mL of water, determined at 25° C. In other embodiments, the acid may have a solubility of between about 100 mg per 100 mL of water to about 1 g per 100 mL of water, between about 0.5 g per 100 mL of water to about 2 g per 100 mL of water, between about 1 g per 100 mL of water to about 10 g per 100 mL of water, or between about 5 g per 100 mL of water to about 50 g per 100 mL of water, determined at 25° C. In some embodiments, the acid may be miscible with water at 25° C.

In some embodiments, disclosed nanoparticles may be essentially free of the acid used during the preparation of the nanoparticles. In other embodiments, disclosed nanoparticles may comprise the acid. For instance, in some embodiments, the acid content in disclosed nanoparticles may be between about 0.0001 wt % to about 0.5 wt %, between about 0.001 wt % to about 0.5 wt %, between about 0.01 wt % to about 0.5 wt %, between about 0.1 wt % to about 0.5 wt %, between about 0.0001 wt % to about 0.4 wt %, between about 0.0001 wt % to about 0.3 wt %, between about 0.0001 wt % to about 0.2 wt %, between about 0.0001 wt % to about 0.1 wt %, between about 0.0001 wt % to about 0.01 wt %, or between about 0.0001 wt % to about 0.001 wt %.

In some embodiments, disclosed nanoparticles substantially immediately release (e.g., over about 1 minute to about 30 minutes, about 1 minute to about 25 minutes, about 5 minutes to about 30 minutes, about 5 minutes to about 1 hour, about 1 hour, or about 24 hours) less than about 2%, less than about 5%, less than about 10%, less than about 15%, less than about 20%, less than about 25%, or less than about 30% of the therapeutic agent, for example when placed in a phosphate buffer solution at room temperature (e.g., 25° C.) and/or at 37° C. In certain embodiments, disclosed nanoparticles comprising a therapeutic agent may release the therapeutic agent when placed in an aqueous solution (e.g., a phosphate buffer solution), e.g., at 25° C. and/or at 37° C., at a rate substantially corresponding to about 0.01 to about 50%, in some embodiments about 0.01 to about 25%, in some embodiments about 0.01 to about 15%, or in some embodiments about 0.01 to about 10%, of the therapeutic agent released over about 1 hour. In some embodiments, disclosed nanoparticles comprising a therapeutic agent may release the therapeutic agent when placed in an aqueous solution (e.g., a phosphate buffer solution), e.g., at 25° C. and/or at 37° C., at a rate substantially corresponding to about 10 to about 70%, in some embodiments about 10 to about 45%, in some embodiments about 10 to about 35%, or in some embodiments about 10 to about 25%, of the therapeutic agent released over about 4 hours.

In some embodiments, disclosed nanoparticles may substantially retain the therapeutic agent, e.g., for at least about 1 minute, at least about 1 hour, or more, when placed in a phosphate buffer solution at 37° C.

Nanoparticles disclosed herein include one, two, three or more biocompatible and/or biodegradable polymers. For example, a contemplated nanoparticle may include about 40 to about 99.8 weight percent, in some embodiments about 50 to about 99.8 weight percent, in some embodiments about 50 to about 99.5 weight percent, in some embodiments about 50 to about 98 weight percent, in some embodiments about 40 to about 94 weight percent, in some embodiments about 50 to about 94 weight percent, in some embodiments about 60 to about 96 weight percent, in some embodiments about 60 to about 85 weight percent, and in some embodiments about 65 to about 85 weight percent of one or more block co-polymers that include a biodegradable polymer and poly(ethylene glycol) (PEG), and about 0 to about 50 weight percent of a biodegradable homopolymer.

Disclosed nanoparticles may include a therapeutic agent. For example, a composition comprising such nanoparticles may be capable of delivering an effective amount of the therapeutic agent to, e.g., a target body area of a patient. Any suitable therapeutic agent may be used in disclosed nanoparticles.

In some embodiments, disclosed nanoparticles may include about 0.2 to about 35 weight percent, about 0.2 to about 20 weight percent, about 0.2 to about 10 weight percent, about 0.2 to about 5 weight percent, about 0.3 to about 5 weight percent, about 0.4 to about 5 weight percent, about 0.5 to about 5 weight percent, about 0.75 to about 5 weight percent, about 1 to about 5 weight percent, about 2 to about 5 weight percent, about 0.3 to about 3 weight percent, about 0.4 to about 3 weight percent, about 0.5 to about 3 weight percent, about 0.75 to about 3 weight percent, about 1 to about 3 weight percent, about 2 to about 3 weight percent, about 2 to about 10 weight percent, about 2 to about 20 weight percent, about 2 to about 30 weight percent, about 3 to about 40 weight percent, about 5 to about 15 weight percent, about 5 to about 30 weight percent, about 10 to about 30 weight percent, about 15 to 25 weight percent, or even about 4 to about 25 weight percent of a therapeutic agent.

In certain embodiments, disclosed nanoparticles comprise an acid and/or are prepared by a process that includes an acid. Such nanoparticles may have a higher drug loading than nanoparticles prepared by a process without acid. For example, drug loading (e.g., by weight) of disclosed nanoparticles prepared by a process comprising the acid may be between about 2 times to about 10 times higher than disclosed nanoparticles prepared by a process without the acid. In some embodiments, the drug loading (by weight) of disclosed nanoparticles prepared by a first process comprising the acid may be at least about 2 times higher, at least about 3 times higher, at least about 4 times higher, at least about 5 times higher, or at least about 10 times higher than disclosed nanoparticles prepared by a second process, where the second process is identical to the first process except that the second process does not include the acid.

In one embodiment, disclosed therapeutic nanoparticles may include a targeting ligand, e.g., a low-molecular weight PSMA ligand effective for targeting or binding to prostate specific membrane antigen. In certain embodiments, the low-molecular weight ligand is conjugated to a polymer, and the nanoparticle comprises a certain ratio of ligand-conjugated polymer (e.g., PLA-PEG-Ligand) to non-functionalized polymer (e.g., PLA-PEG or PLGA-PEG). The nanoparticle can have an optimized ratio of these two polymers such that an effective amount of ligand is associated with the nanoparticle for treatment of a disease or disorder, such as cancer. For example, an increased ligand density may increase target binding (cell binding/target uptake), making the nanoparticle "target specific." Alternatively, a certain concentration of non-functionalized polymer (e.g., non-functionalized PLGA-PEG copolymer) in the nanoparticle can control inflammation and/or immunogenicity (i.e., the ability to provoke an immune response), and allow the nanoparticle to have a circulation half-life that is adequate for the treatment of a disease or disorder (e.g., prostate cancer). Furthermore, the non-functionalized polymer may, in some embodiments, lower the rate of clearance from the circulatory system via the reticuloendothelial system (RES). Thus, the non-functionalized polymer may provide the nanoparticle with characteristics that may allow the particle to travel through the body upon administration. In some embodiments, a non-functionalized polymer may balance an otherwise high concentration of ligands, which can otherwise accelerate clearance by the subject, resulting in less delivery to the target cells.

In some embodiments, nanoparticles disclosed herein may include functionalized polymers conjugated to a ligand that constitute approximately 0.1-50, e.g., 0.1-30, e.g., 0.1-20, e.g., 0.1-10 mole percent of the entire polymer composition of the nanoparticle (i.e., functionalized +non-functionalized polymer). Also disclosed herein, in another embodiment, are nanoparticles that include a polymer conjugated (e.g., covalently with (i.e., through a linker (e.g., an alkylene linker)) or a bond) with one or more low-molecular weight ligands, wherein the weight percent low-molecular weight ligand with respect to total polymer is between about 0.001 and 5, e.g., between about 0.001 and 2, e.g., between about 0.001 and 1.

In some embodiments, disclosed nanoparticles may be able to bind efficiently to or otherwise associate with a biological entity, for example, a particular membrane component or cell surface receptor. Targeting of a therapeutic agent (e.g., to a particular tissue or cell type, to a specific diseased tissue but not to normal tissue, etc.) is desirable for the treatment of tissue specific diseases such as solid tumor cancers (e.g., prostate cancer). For example, in contrast to systemic delivery of a cytotoxic anti-cancer agent, the nanoparticles disclosed herein may substantially prevent the agent from killing healthy cells. Additionally, disclosed nanoparticles may allow for the administration of a lower dose of the agent (as compared to an effective amount of agent administered without disclosed nanoparticles or formulations) which may reduce the undesirable side effects commonly associated with traditional chemotherapy.

In general, a "nanoparticle" refers to any particle having a diameter of less than 1000 nm, e.g., about 10 nm to about 200 nm. Disclosed therapeutic nanoparticles may include nanoparticles having a diameter of about 60 to about 120 nm, or about 70 to about 120 nm, or about 80 to about 120 nm, or about 90 to about 120 nm, or about 100 to about 120 nm, or about 60 to about 130 nm, or about 70 to about 130 nm, or about 80 to about 130 nm, or about 90 to about 130 nm, or about 100 to about 130 nm, or about 110 to about 130 nm, or about 60 to about 140 nm, or about 70 to about 140 nm, or about 80 to about 140 nm, or about 90 to about 140 nm, or about 100 to about 140 nm, or about 110 to about 140 nm, or about 60 to about 150 nm, or about 70 to about 150 nm, or about 80 to about 150 nm, or about 90 to about 150 nm, or about 100 to about 150 nm, or about 110 to about 150 nm, or about 120 to about 150 nm.

Polymers

In some embodiments, the nanoparticles may comprise a matrix of polymers and a therapeutic agent. In some embodiments, a therapeutic agent and/or targeting moiety (i.e., a low-molecular weight PSMA ligand) can be associated with at least part of the polymeric matrix. For example, in some embodiments, a targeting moiety (e.g., ligand) can be covalently associated with the surface of a polymeric matrix. In some embodiments, covalent association is mediated by a linker. The therapeutic agent can be associated with the surface of, encapsulated within, surrounded by, and/or dispersed throughout the polymeric matrix.

A wide variety of polymers and methods for forming particles therefrom are known in the art of drug delivery. In some embodiments, the disclosure is directed toward nanoparticles with at least two macromolecules, wherein the first macromolecule comprises a first polymer bound to a low-molecular weight ligand (e.g., targeting moiety); and the second macromolecule comprising a second polymer that is not bound to a targeting moiety. The nanoparticle can optionally include one or more additional, unfunctionalized, polymers.

Any suitable polymer can be used in the disclosed nanoparticles. Polymers can be natural or unnatural (synthetic) polymers. Polymers can be homopolymers or copolymers comprising two or more monomers. In terms of sequence, copolymers can be random, block, or comprise a combination of random and block sequences. Typically, polymers are organic polymers.

The term "polymer," as used herein, is given its ordinary meaning as used in the art, i.e., a molecular structure comprising one or more repeat units (monomers), connected by covalent bonds. The repeat units may all be identical, or in some cases, there may be more than one type of repeat unit present within the polymer. In some cases, the polymer can be biologically derived, i.e., a biopolymer. Non-limiting examples include peptides or proteins. In some cases, additional moieties may also be present in the polymer, for example biological moieties such as those described below. If more than one type of repeat unit is present within the polymer, then the polymer is said to be a "copolymer." It is to be understood that in any embodiment employing a polymer, the polymer being employed may be a copolymer in some cases. The repeat units forming the copolymer may be arranged in any fashion. For example, the repeat units may be arranged in a random order, in an alternating order, or as a block copolymer, i.e., comprising one or more regions each comprising a first repeat unit (e.g., a first block), and one or more regions each comprising a second repeat unit (e.g., a second block), etc. Block copolymers may have two (a diblock copolymer), three (a triblock copolymer), or more numbers of distinct blocks.

Disclosed particles can include copolymers, which, in some embodiments, describes two or more polymers (such as those described herein) that have been associated with each other, usually by covalent bonding of the two or more polymers together. Thus, a copolymer may comprise a first polymer and a second polymer, which have been conjugated together to form a block copolymer where the first polymer can be a first block of the block copolymer and the second polymer can be a second block of the block copolymer. Of course, those of ordinary skill in the art will understand that a block copolymer may, in some cases, contain multiple blocks of polymer, and that a "block copolymer," as used herein, is not limited to only block copolymers having only a single first block and a single second block. For instance, a block copolymer may comprise a first block comprising a first polymer, a second block comprising a second polymer, and a third block comprising a third polymer or the first polymer, etc. In some cases, block copolymers can contain any number of first blocks of a first polymer and second blocks of a second polymer (and in certain cases, third blocks, fourth blocks, etc.). In addition, it should be noted that block copolymers can also be formed, in some instances, from other block copolymers. For example, a first block copolymer may be conjugated to another polymer (which may be a homopolymer, a biopolymer, another block copolymer, etc.), to form a new block copolymer containing multiple types of blocks, and/or to other moieties (e.g., to non-polymeric moieties).

In some embodiments, the polymer (e.g., copolymer, e.g., block copolymer) can be amphiphilic, i.e., having a hydrophilic portion and a hydrophobic portion, or a relatively hydrophilic portion and a relatively hydrophobic portion. A hydrophilic polymer can be one generally that attracts water and a hydrophobic polymer can be one that generally repels water. A hydrophilic or a hydrophobic polymer can be identified, for example, by preparing a sample of the polymer and measuring its contact angle with water (typically, the polymer will have a contact angle of less than 60°, while a hydrophobic polymer will have a contact angle of greater than about 60°). In some cases, the hydrophilicity of two or more polymers may be measured relative to each other, i.e., a first polymer may be more hydrophilic than a second polymer. For instance, the first polymer may have a smaller contact angle than the second polymer.

In one set of embodiments, a polymer (e.g., copolymer, e.g., block copolymer) contemplated herein includes a biocompatible polymer, i.e., the polymer that does not typically induce an adverse response when inserted or injected into a living subject, for example, without significant inflammation and/or acute rejection of the polymer by the immune system, for instance, via a T-cell response. Accordingly, the therapeutic particles contemplated herein can be non-immunogenic. The term non-immunogenic as used herein refers to endogenous growth factor in its native state which normally elicits no, or only minimal levels of, circulating antibodies, T-cells, or reactive immune cells, and which normally does not elicit in the individual an immune response against itself.

Biocompatibility typically refers to the acute rejection of material by at least a portion of the immune system, i.e., a nonbiocompatible material implanted into a subject provokes an immune response in the subject that can be severe enough such that the rejection of the material by the immune system cannot be adequately controlled, and often is of a degree such that the material must be removed from the subject. One simple test to determine biocompatibility can be to expose a polymer to cells in vitro; biocompatible polymers are polymers that typically will not result in significant cell death at moderate concentrations, e.g., at concentrations of 50 micrograms/$10^6$ cells. For instance, a biocompatible polymer may cause less than about 20% cell death when exposed to cells such as fibroblasts or epithelial cells, even if phagocytosed or otherwise uptaken by such cells. Non-limiting examples of biocompatible polymers that may be useful in various embodiments include polydioxanone (PDO), polyhydroxyalkanoate, polyhydroxybutyrate, poly(glycerol sebacate), polyglycolide (i.e., poly(glycolic) acid) (PGA), polylactide (i.e., poly(lactic) acid) (PLA), poly(lactic) acid-co-poly(glycolic) acid (PLGA), polycaprolactone, or copolymers or derivatives including these and/or other polymers.

In certain embodiments, contemplated biocompatible polymers may be biodegradable, i.e., the polymer is able to degrade, chemically and/or biologically, within a physiological environment, such as within the body. As used herein, "biodegradable" polymers are those that, when introduced into cells, are broken down by the cellular machinery (biologically degradable) and/or by a chemical process, such as hydrolysis, (chemically degradable) into components that the cells can either reuse or dispose of without significant toxic effect on the cells. In one embodiment, the biodegradable polymer and their degradation byproducts can be biocompatible.

Particles disclosed herein may or may not contain PEG. In addition, certain embodiments can be directed towards copolymers containing poly(ester-ether)s, e.g., polymers having repeat units joined by ester bonds (e.g., R—C(O)—O—R' bonds) and ether bonds (e.g., R—O—R' bonds). In some embodiments, a biodegradable polymer, such as a hydrolyzable polymer, containing carboxylic acid groups, may be conjugated with poly(ethylene glycol) repeat units to form a poly(ester-ether). A polymer (e.g., copolymer, e.g., block copolymer) containing poly(ethylene glycol) repeat units can also be referred to as a "PEGylated" polymer.

For instance, a contemplated polymer may be one that hydrolyzes spontaneously upon exposure to water (e.g., within a subject), the polymer may degrade upon exposure to heat (e.g., at temperatures of about 37° C.). Degradation of a polymer may occur at varying rates, depending on the polymer or copolymer used. For example, the half-life of the polymer (the time at which 50% of the polymer can be degraded into monomers and/or other nonpolymeric moieties) may be on the order of days, weeks, months, or years, depending on the polymer. The polymers may be biologically degraded, e.g., by enzymatic activity or cellular machinery, in some cases, for example, through exposure to a lysozyme (e.g., having relatively low pH). In some cases, the polymers may be broken down into monomers and/or other nonpolymeric moieties that cells can either reuse or dispose of without significant toxic effect on the cells (for example, polylactide may be hydrolyzed to form lactic acid, polyglycolide may be hydrolyzed to form glycolic acid, etc.).

In some embodiments, polymers may be polyesters, including copolymers comprising lactic acid and glycolic acid units, such as poly(lactic acid-co-glycolic acid) and poly(lactide-co-glycolide), collectively referred to herein as "PLGA"; and homopolymers comprising glycolic acid units, referred to herein as "PGA," and lactic acid units, such as poly-L-lactic acid, poly-D-lactic acid, poly-D,L-lactic acid, poly-L-lactide, poly-D-lactide, and poly-D,L-lactide, collectively referred to herein as "PLA." In some embodiments, exemplary polyesters include, for example, polyhydroxyacids; PEGylated polymers and copolymers of lactide and glycolide (e.g., PEGylated PLA, PEGylated PGA, PEGylated PLGA, and derivatives thereof). In some embodiments, polyesters include, for example, polyanhydrides, poly(ortho ester) PEGylated poly(ortho ester), poly(caprolactone), PEGylated poly(caprolactone), polylysine, PEGylated polylysine, poly(ethylene imine), PEGylated poly(ethylene imine), poly(L-lactide-co-L-lysine), poly(serine ester), poly(4-hydroxy-L-proline ester), poly[α-(4-aminobutyl)-L-glycolic acid], and derivatives thereof.

In some embodiments, a polymer may be PLGA. PLGA is a biocompatible and biodegradable co-polymer of lactic acid and glycolic acid, and various forms of PLGA can be characterized by the ratio of lactic acid:glycolic acid. Lactic acid can be L-lactic acid, D-lactic acid, or D,L-lactic acid. The degradation rate of PLGA can be adjusted by altering the lactic acid-glycolic acid ratio. In some embodiments, PLGA can be characterized by a lactic acid:glycolic acid ratio of approximately 85:15, approximately 75:25, approximately 60:40, approximately 50:50, approximately 40:60, approximately 25:75, or approximately 15:85. In some embodiments, the ratio of lactic acid to glycolic acid monomers in the polymer of the particle (e.g., the PLGA block copolymer or PLGA-PEG block copolymer), may be selected to optimize for various parameters such as water uptake, therapeutic agent release and/or polymer degradation kinetics can be optimized.

In some embodiments, polymers may be one or more acrylic polymers. In certain embodiments, acrylic polymers include, for example, acrylic acid and methacrylic acid copolymers, methyl methacrylate copolymers, ethoxyethyl methacrylates, cyanoethyl methacrylate, amino alkyl methacrylate copolymer, poly(acrylic acid), poly(methacrylic acid), methacrylic acid alkylamide copolymer, poly(methyl methacrylate), poly(methacrylic acid polyacrylamide, amino alkyl methacrylate copolymer, glycidyl methacrylate copolymers, polycyanoacrylates, and combinations comprising one or more of the foregoing polymers. The acrylic polymer may comprise fully-polymerized copolymers of acrylic and methacrylic acid esters with a low content of quaternary ammonium groups.

In some embodiments, polymers can be cationic polymers. In general, cationic polymers are able to condense and/or protect negatively charged strands of nucleic acids (e.g., DNA, RNA, or derivatives thereof). Amine-containing polymers such as poly(lysine), polyethylene imine (PEI), and poly(amidoamine) dendrimers are contemplated for use, in some embodiments, in a disclosed particle.

In some embodiments, polymers can be degradable polyesters bearing cationic side chains. Examples of these polyesters include poly(L-lactide-co-L-lysine), poly(serine ester), and poly(4-hydroxy-L-proline ester).

It is contemplated that PEG may be terminated and include an end group, for example, when PEG is not conjugated to a ligand. For example, PEG may terminate in a hydroxyl, a methoxy or other alkoxyl group, a methyl or other alkyl group, an aryl group, a carboxylic acid, an amine, an amide, an acetyl group, a guanidino group, or an imidazole. Other contemplated end groups include azide, alkyne, maleimide, aldehyde, hydrazide, hydroxylamine, alkoxyamine, or thiol moieties.

Those of ordinary skill in the art will know of methods and techniques for PEGylating a polymer, for example, by using EDC (1-ethyl-3-(3-dimethylaminopropyl)carbodiimide hydrochloride) and NHS (N-hydroxysuccinimide) to react a polymer to a PEG group terminating in an amine, by ring opening polymerization techniques (ROMP), or the like In one embodiment, the molecular weight (or e.g., the ratio of molecular weights of, e.g., different blocks of a copolymer) of the polymers can be optimized for effective treatment as disclosed herein. For example, the molecular weight of a polymer may influence particle degradation rate (such as when the molecular weight of a biodegradable polymer can be adjusted), solubility, water uptake, and drug release kinetics. For example, the molecular weight of the polymer (or e.g., the ratio of molecular weights of, e.g., different blocks of a copolymer) can be adjusted such that the particle biodegrades in the subject being treated within a reasonable period of time (ranging from a few hours to 1-2 weeks, 3-4 weeks, 5-6 weeks, 7-8 weeks, etc.). A disclosed particle can for example comprise a diblock copolymer of PEG and PL(G)A, wherein for example, the PEG portion may have a number average molecular weight of about 1,000-20,000, e.g., about 2,000-20,000, e.g., about 2 to about 10,000, and the PL(G)A portion may have a number average molecular weight of about 5,000 to about 20,000, or about 5,000-100,000, e.g., about 20,000-70,000, e.g., about 15,000-50,000.

For example, disclosed here is an exemplary therapeutic nanoparticle that includes about 10 to about 99 weight percent poly(lactic) acid-poly(ethylene)glycol copolymer or poly(lactic)-co-poly(glycolic) acid-poly(ethylene)glycol copolymer, or about 20 to about 80 weight percent, about 40 to about 80 weight percent, or about 30 to about 50 weight percent, or about 70 to about 90 weight percent poly(lactic) acid-poly(ethylene)glycol copolymer or poly(lactic)-co-poly(glycolic) acid-poly(ethylene)glycol copolymer. Exemplary poly(lactic) acid-poly(ethylene)glycol copolymers can include a number average molecular weight of about 15 to about 20 kDa, or about 10 to about 25 kDa of poly(lactic) acid and a number average molecular weight of about 4 to about 6, or about 2 kDa to about 10 kDa of poly(ethylene) glycol.

In some embodiments, the poly(lactic) acid-poly(ethylene)glycol copolymer may have a poly(lactic) acid number average molecular weight fraction of about 0.6 to about 0.95, in some embodiments between about 0.7 to about 0.9, in some embodiments between about 0.6 to about 0.8, in some embodiments between about 0.7 to about 0.8, in some embodiments between about 0.75 to about 0.85, in some embodiments between about 0.8 to about 0.9, and in some embodiments between about 0.85 to about 0.95. It should be understood that the poly(lactic) acid number average molecular weight fraction may be calculated by dividing the number average molecular weight of the poly(lactic) acid component of the copolymer by the sum of the number average molecular weight of the poly(lactic) acid component and the number average molecular weight of the poly(ethylene)glycol component.

Disclosed nanoparticles may optionally include about 1 to about 50 weight percent poly(lactic) acid or poly(lactic) acid-co-poly(glycolic) acid (which does not include PEG), or may optionally include about 1 to about 50 weight percent, or about 10 to about 50 weight percent or about 30 to about 50 weight percent poly(lactic) acid or poly(lactic) acid-co-poly(glycolic) acid. For example, poly(lactic) or poly(lactic)-co-poly(glycolic) acid may have a number average molecule weight of about 5 to about 15 kDa, or about 5 to about 12 kDa. Exemplary PLA may have a number average molecular weight of about 5 to about 10 kDa. Exemplary PLGA may have a number average molecular weight of about 8 to about 12 kDa.

A therapeutic nanoparticle may, in some embodiments, contain about 10 to about 30 weight percent, in some embodiments about 10 to about 25 weight percent, in some embodiments about 10 to about 20 weight percent, in some embodiments about 10 to about 15 weight percent, in some embodiments about 15 to about 20 weight percent, in some embodiments about 15 to about 25 weight percent, in some embodiments about 20 to about 25 weight percent, in some embodiments about 20 to about 30 weight percent, or in some embodiments about 25 to about 30 weight percent of poly(ethylene)glycol, where the poly(ethylene)glycol may be present as a poly(lactic) acid-poly(ethylene)glycol copolymer, poly(lactic)-co-poly(glycolic) acid-poly(ethylene) glycol copolymer, or poly(ethylene)glycol homopolymer.

In certain embodiments, the polymers of the nanoparticles can be conjugated to a lipid. The polymer can be, for example, a lipid-terminated PEG. As described below, the lipid portion of the polymer can be used for self-assembly with another polymer, facilitating the formation of a nanoparticle. For example, a hydrophilic polymer could be conjugated to a lipid that will self-assemble with a hydrophobic polymer.

In some embodiments, lipids are oils. In general, any oil known in the art can be conjugated to the polymers used in the nanoparticles. In some embodiments, an oil can comprise one or more fatty acid groups or salts thereof. In some embodiments, a fatty acid group can comprise digestible, long chain (e.g., $C_8$-$C_{50}$), substituted or unsubstituted hydrocarbons. In some embodiments, a fatty acid group can be a $C_{10}$-$C_{20}$ fatty acid or salt thereof. In some embodiments, a fatty acid group can be a $C_{15}$-$C_{20}$ fatty acid or salt thereof. In some embodiments, a fatty acid can be unsaturated. In some embodiments, a fatty acid group can be monounsaturated. In some embodiments, a fatty acid group can be polyunsaturated. In some embodiments, a double bond of an unsaturated fatty acid group can be in the cis conformation. In some embodiments, a double bond of an unsaturated fatty acid can be in the trans conformation.

In some embodiments, a fatty acid group can be one or more of butyric, caproic, caprylic, capric, lauric, myristic, palmitic, stearic, arachidic, behenic, or lignoceric acid. In some embodiments, a fatty acid group can be one or more of palmitoleic, oleic, vaccenic, linoleic, alpha-linolenic, gamma-linoleic, arachidonic, gadoleic, arachidonic, eicosapentaenoic, docosahexaenoic, or erucic acid.

In a particular embodiment, the lipid is of the Formula V:

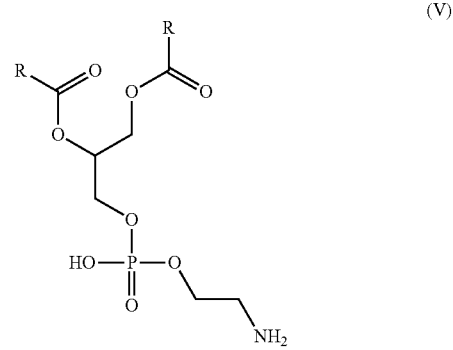

and salts thereof, wherein each R is, independently, $C_{1-30}$ alkyl. In one embodiment of Formula V, the lipid is 1,2 distearoyl-sn-glycero-3-phosphoethanolamine (DSPE), and salts thereof, e.g., the sodium salt.

In one embodiment, optional small molecule targeting moieties are bonded, e.g., covalently bonded, to the lipid component of the nanoparticle. For example, provided herein is a nanoparticle comprising a therapeutic agent, a polymeric matrix comprising functionalized and non-functionalized polymers, optionally a lipid, and optionally a low-molecular weight PSMA targeting ligand, wherein the targeting ligand is bonded, e.g., covalently bonded, to the lipid component of the nanoparticle. In one embodiment, the lipid component that is bonded to the low-molecular weight targeting moiety is of the Formula V. In another embodiment, a target-specific nanoparticle is provided comprising a therapeutic agent, a polymeric matrix, DSPE, and a low-molecular weight PSMA targeting ligand, wherein the ligand is bonded, e.g., covalently bonded, to DSPE. For example, the nanoparticle may comprise a polymeric matrix comprising PLGA-DSPE-PEG-Ligand.

Targeting Moieties

Provided herein are nanoparticles that may include an optional targeting moiety, i.e., a moiety able to bind to or otherwise associate with a biological entity, for example, a membrane component, a cell surface receptor, prostate specific membrane antigen, or the like. A targeting moiety present on the surface of the particle may allow the particle to become localized at a particular targeting site, for instance, a tumor, a disease site, a tissue, an organ, a type of cell, etc. As such, the nanoparticle may then be "target specific." The drug or other payload may then, in some cases, be released from the particle and allowed to interact locally with the particular targeting site.

In one embodiment, a disclosed nanoparticle includes a targeting moiety that is a low-molecular weight ligand, e.g., a low-molecular weight PSMA ligand. The term "bind" or "binding," as used herein, refers to the interaction between a corresponding pair of molecules or portions thereof that exhibit mutual affinity or binding capacity, typically due to specific or non-specific binding or interaction, including, but not limited to, biochemical, physiological, and/or chemical interactions. "Biological binding" defines a type of interaction that occurs between pairs of molecules including proteins, nucleic acids, glycoproteins, carbohydrates, hormones, or the like. The term "binding partner" refers to a molecule that can undergo binding with a particular molecule. "Specific binding" refers to molecules, such as polynucleotides, that are able to bind to or recognize a binding partner (or a limited number of binding partners) to a substantially higher degree than to other, similar biological entities. In one set of embodiments, the targeting moiety has an affinity (as measured via a disassociation constant) of less than about 1 micromolar, at least about 10 micromolar, or at least about 100 micromolar.

For example, a targeting portion may cause the particles to become localized to a tumor (e.g., a solid tumor) a disease site, a tissue, an organ, a type of cell, etc. within the body of a subject, depending on the targeting moiety used. For example, a low-molecular weight PSMA ligand may become localized to a solid tumor, e.g., breast or prostate tumors or cancer cells. The subject may be a human or non-human animal. Examples of subjects include, but are not limited to, a mammal such as a dog, a cat, a horse, a donkey, a rabbit, a cow, a pig, a sheep, a goat, a rat, a mouse, a guinea pig, a hamster, a primate, a human or the like.

Contemplated targeting moieties may include small molecules. In certain embodiments, the term "small molecule" refers to organic compounds, whether naturally-occurring or artificially created (e.g., via chemical synthesis) that have relatively low molecular weight and that are not proteins, polypeptides, or nucleic acids. Small molecules typically have multiple carbon-carbon bonds. In certain embodiments, small molecules are less than about 2000 g/mol in size. In some embodiments, small molecules are less than about 1500 g/mol or less than about 1000 g/mol. In some embodiments, small molecules are less than about 800 g/mol or less than about 500 g/mol, for example about 100 g/mol to about 600 g/mol, or about 200 g/mol to about 500 g/mol.

For example, a targeting moiety may target prostate cancer tumors, for example a target moiety may be PSMA peptidase inhibitor. These moieties are also referred to herein as "low-molecular weight PSMA ligands." When compared with expression in normal tissues, expression of prostate specific membrane antigen (PSMA) is at least 10-fold overexpressed in malignant prostate relative to normal tissue, and the level of PSMA expression is further up-regulated as the disease progresses into metastatic phases (Silver et al. 1997, *Clin. Cancer Res.*, 3:81).

In some embodiments, the low-molecular weight PSMA ligand is of the Formulae I, II, III or IV:

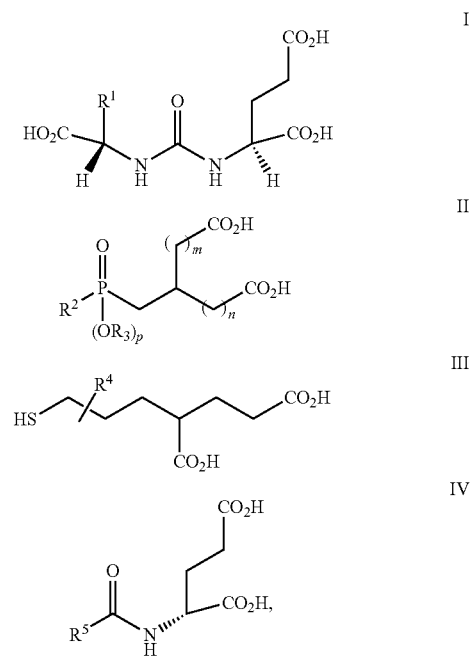

and enantiomers, stereoisomers, rotamers, tautomers, diastereomers, or racemates thereof;

wherein m and n are each, independently, 0, 1, 2 or 3; p is 0 or 1;

$R^1$, $R^2$, $R^4$, and $R^5$ are each, independently, selected from the group consisting of substituted or unsubstituted alkyl (e.g., $C_{1-10}$-alkyl, $C_{1-6}$-alkyl, or $C_{1-4}$-alkyl), substituted or unsubstituted aryl (e.g., phenyl or pyridinyl), and any combination thereof; and $R^3$ is H or $C_{1-6}$-alkyl (e.g., $CH_3$).

For compounds of Formulae I, II, III and IV, $R^1$, $R^2$, $R^4$ or $R^5$ comprise points of attachment to the nanoparticle, e.g., a point of attachment to a polymer that forms part of a disclosed nanoparticle, e.g., PEG. The point of attachment may be formed by a covalent bond, ionic bond, hydrogen bond, a bond formed by adsorption including chemical adsorption and physical adsorption, a bond formed from van der Waals bonds, or dispersion forces. For example, if $R^1$, $R^2$, $R^4$, or $R^5$ are defined as an aniline or $C_{1-6}$-alkyl-$NH_2$ group, any hydrogen (e.g., an amino hydrogen) of these functional groups could be removed such that the low-molecular weight PSMA ligand is covalently bound to the polymeric matrix (e.g., the PEG-block of the polymeric matrix) of the nanoparticle. As used herein, the term "covalent bond" refers to a bond between two atoms formed by sharing at least one pair of electrons.

In particular embodiments of the Formulae I, II, III or IV, $R^1$, $R^2$, $R^4$, and $R^5$ are each, independently, $C_{1-6}$-alkyl or phenyl, or any combination of $C_{1-6}$-alkyl or phenyl, which are independently substituted one or more times with OH, SH, NH$_2$, or CO$_2$H, and wherein the alkyl group may be interrupted by N(H), S, or O. In another embodiment, R$^1$, R$^2$, R$^4$, and R$^5$ are each, independently, CH$_2$-Ph, (CH$_2$)$_2$—SH, CH$_2$—SH, (CH$_2$)$_2$C(H)(NH$_2$)CO$_2$H, CH$_2$C(H)(NH$_2$)CO$_2$H, CH(NH$_2$)CH$_2$CO$_2$H, (CH$_2$)$_2$C(H)(SH)CO$_2$H, CH$_2$—N(H)-Ph, O—CH$_2$-Ph, or O—(CH$_2$)$_2$-Ph, wherein each Ph may be independently substituted one or more times with OH, NH$_2$, CO$_2$H, or SH. For these formulae, the NH$_2$, OH or SH groups serve as the point of covalent attachment to the nanoparticle (e.g., —N(H)-PEG, —O-PEG, or —S-PEG).

In still another embodiment, the low-molecular weight PSMA ligand is selected from the group consisting of

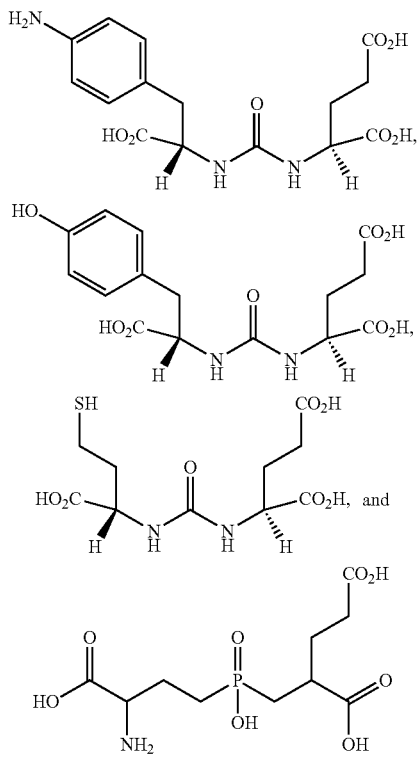

and enantiomers, stereoisomers, rotamers, tautomers, diastereomers, or racemates thereof, and wherein the NH$_2$, OH, or SH groups serve as the point of covalent attachment to the nanoparticle (e.g., —N(H)-PEG, —O-PEG, or —S-PEG).

In another embodiment, the low-molecular weight PSMA ligand is selected from the group consisting of

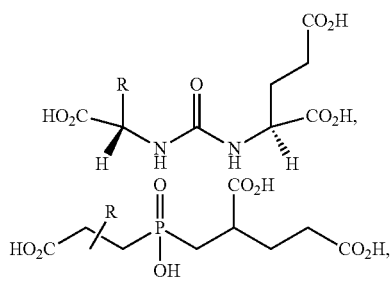

and enantiomers, stereoisomers, rotamers, tautomers, diastereomers, or racemates thereof, wherein R is independently selected from the group consisting of NH$_2$, SH, OH, CO$_2$H, C$_{1-6}$-alkyl that is substituted with NH$_2$, SH, OH, or CO$_2$H, and phenyl that is substituted with NH$_2$, SH, OH, or CO$_2$H, and wherein R serves as the point of covalent attachment to the nanoparticle (e.g., —N(H)-PEG, —S-PEG, —O-PEG, or CO$_2$-PEG).

In another embodiment, the low-molecular weight PSMA ligand is selected from the group consisting of

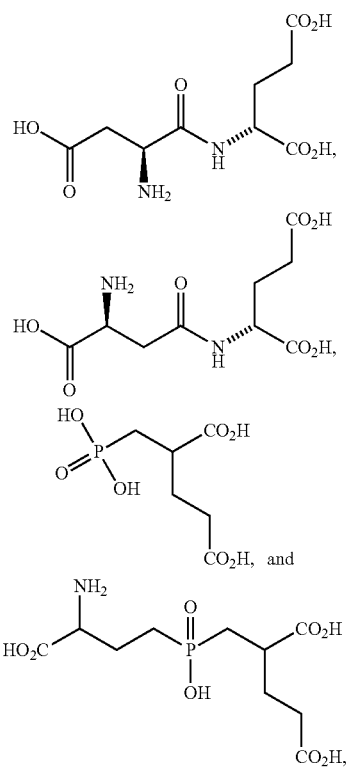

and enantiomers, stereoisomers, rotamers, tautomers, diastereomers, or racemates thereof, wherein the NH$_2$ or CO$_2$H groups serve as the point of covalent attachment to the nanoparticle (e.g., —N(H)-PEG, or CO$_2$-PEG). These compounds may be further substituted with NH$_2$, SH, OH, CO$_2$H, C$_{1-6}$-alkyl that is substituted with NH$_2$, SH, OH, or CO$_2$H, or phenyl that is substituted with NH$_2$, SH, OH or CO$_2$H, wherein these functional groups can also serve as the point of covalent attachment to the nanoparticle.

In another embodiment, the low-molecular weight PSMA ligand is

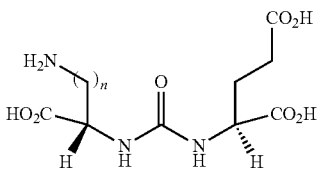

and enantiomers, stereoisomers, rotamers, tautomers, diastereomers, or racemates thereof, wherein n is 1, 2, 3, 4, 5, or 6. For this ligand, the $NH_2$ group serves as the point of covalent attachment to the nanoparticle (e.g., —N(H)-PEG).

In still another embodiment, the low-molecular weight PSMA ligand is

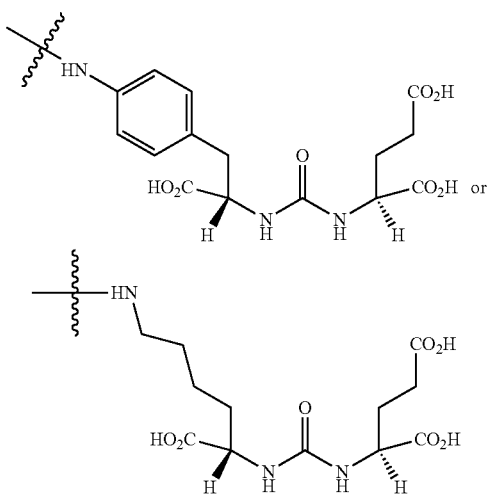

and enantiomers, stereoisomers, rotamers, tautomers, diastereomers, or racemates thereof. Particularly, the butyl-amine compound has the advantage of ease of synthesis, especially because of its lack of a benzene ring. Furthermore, without wishing to be bound by theory, the butyl-amine compound will likely break down into naturally occurring molecules (i.e., lysine and glutamic acid), thereby minimizing toxicity concerns.

In some embodiments, small molecule targeting moieties that may be used to target cells associated with solid tumors such as prostate or breast cancer tumors include PSMA peptidase inhibitors such as 2-PMPA, GPI5232, VA-033, phenylalkylphosphonamidates and/or analogs and derivatives thereof. In some embodiments, small molecule targeting moieties that may be used to target cells associated with prostate cancer tumors include thiol and indole thiol derivatives, such as 2-MPPA and 3-(2-mercaptoethyl)-1H-indole-2-carboxylic acid derivatives. In some embodiments, small molecule targeting moieties that may be used to target cells associated with prostate cancer tumors include hydroxamate derivatives. In some embodiments, small molecule targeting moieties that may be used to target cells associated with prostate cancer tumors include PBDA- and urea-based inhibitors, such as ZJ 43, ZJ 11, ZJ 17, ZJ 38 and/or and analogs and derivatives thereof, androgen receptor targeting agents (ARTAs), polyamines, such as putrescine, spermine, and spermidine, inhibitors of the enzyme glutamate carboxylase II (GCPII), also known as NAAG Peptidase or NAALADase.

In another embodiment, the targeting moiety can be a ligand that targets Her2, EGFR, folate receptor or toll receptors. In another embodiment, the targeting moiety is folate, folic acid, or an EGFR binding molecule.

For example, contemplated the targeting moieties may include a nucleic acid, polypeptide, glycoprotein, carbohydrate, or lipid. For example, a targeting moiety can be a nucleic acid targeting moiety (e.g. an aptamer, e.g., the A10 aptamer) that binds to a cell type specific marker. In general, an aptamer is an oligonucleotide (e.g., DNA, RNA, or an analog or derivative thereof) that binds to a particular target, such as a polypeptide. In some embodiments, a targeting moiety may be a naturally occurring or synthetic ligand for a cell surface receptor, e.g., a growth factor, hormone, LDL, transferrin, etc. A targeting moiety can be an antibody, which term is intended to include antibody fragments, characteristic portions of antibodies, single chain targeting moieties can be identified, e.g., using procedures such as phage display.

Targeting moieties may be a targeting peptide or targeting peptidomimetic has a length of up to about 50 residues. For example, a targeting moieties may include the amino acid sequence AKERC, CREKA, ARYLQKLN, or AXYLZZLN, wherein X and Z are variable amino acids, or conservative variants or peptidomimetics thereof. In particular embodiments, the targeting moiety is a peptide that includes the amino acid sequence AKERC, CREKA, ARYLQKLN, or AXYLZZLN, wherein X and Z are variable amino acids, and has a length of less than 20, 50 or 100 residues. The CREKA (Cys Arg Glu Lys Ala) peptide or a peptidomimetic thereof peptide or the octapeptide AXYLZZLN are also contemplated as targeting moieties, as well as peptides, or conservative variants or peptidomimetics thereof, that binds or forms a complex with collagen IV, or the targets tissue basement membrane (e.g., the basement membrane of a blood vessel), can be used as a targeting moiety. Exemplary targeting moieties include peptides that target ICAM (intercellular adhesion molecule, e.g., ICAM-1).

Targeting moieties disclosed herein can be, in some embodiments, conjugated to a disclosed polymer or copolymer (e.g., PLA-PEG), and such a polymer conjugate may form part of a disclosed nanoparticle.

In some embodiments, a therapeutic nanoparticle may include a polymer-drug conjugate. For example, a drug may be conjugated to a disclosed polymer or copolymer (e.g., PLA-PEG), and such a polymer-drug conjugate may form part of a disclosed nanoparticle. For example, a disclosed therapeutic nanoparticle may optionally include about 0.2 to about 30 weight percent of a PLA-PEG or PLGA-PEG, wherein the PEG is functionalized with a drug (e.g., PLA-PEG-Drug).

A disclosed polymeric conjugate may be formed using any suitable conjugation technique. For instance, two compounds such as a targeting moiety or drug and a biocompatible polymer (e.g., a biocompatible polymer and a poly (ethylene glycol)) may be conjugated together using techniques such as EDC-NHS chemistry (1-ethyl-3-(3-dimethylaminopropyl)carbodiimide hydrochloride and N-hydroxysuccinimide) or a reaction involving a maleimide or a carboxylic acid, which can be conjugated to one end of a thiol, an amine, or a similarly functionalized polyether. The conjugation of a targeting moiety or drug and a polymer to form a polymer-targeting moiety conjugate or a polymer-drug conjugate can be performed in an organic solvent, such as, but not limited to, dichloromethane, acetonitrile, chloroform, dimethylformamide, tetrahydrofuran, acetone, or the like. Specific reaction conditions can be determined by those of ordinary skill in the art using no more than routine experimentation.

In another set of embodiments, a conjugation reaction may be performed by reacting a polymer that comprises a carboxylic acid functional group (e.g., a poly(ester-ether) compound) with a polymer or other moiety (such as a targeting moiety or drug) comprising an amine. For instance, a targeting moiety, such as a low-molecular weight PSMA ligand, or a drug, such as dasatinib, may be reacted with an amine to form an amine-containing moiety, which can then be conjugated to the carboxylic acid of the polymer. Such a reaction may occur as a single-step reaction, i.e., the conjugation is performed without using intermediates such as N-hydroxysuccinimide or a maleimide. In some embodiments, a drug may be reacted with an amine-containing linker to form an amine-containing drug, which can then be conjugated to the carboxylic acid of the polymer as described above. The conjugation reaction between the amine-containing moiety and the carboxylic acid-terminated polymer (such as a poly(ester-ether) compound) may be achieved, in one set of embodiments, by adding the amine-containing moiety, solubilized in an organic solvent such as (but not limited to) dichloromethane, acetonitrile, chloroform, tetrahydrofuran, acetone, formamide, dimethylformamide, pyridines, dioxane, or dimethylsulfoxide, to a solution containing the carboxylic acid-terminated polymer. The carboxylic acid-terminated polymer may be contained within an organic solvent such as, but not limited to, dichloromethane, acetonitrile, chloroform, dimethylformamide, tetrahydrofuran, or acetone. Reaction between the amine-containing moiety and the carboxylic acid-terminated polymer may occur spontaneously, in some cases. Unconjugated reactants may be washed away after such reactions, and the polymer may be precipitated in solvents such as, for instance, ethyl ether, hexane, methanol, or ethanol. In certain embodiments, a conjugate may be formed between an alcohol-containing moiety and carboxylic acid functional group of a polymer, which can be achieved similarly as described above for conjugates of amines and carboxylic acids.

As a specific example, a low-molecular weight PSMA ligand may be prepared as a targeting moiety in a particle as follows. Carboxylic acid modified poly(lactide-co-glycolide) (PLGA-COOH) may be conjugated to an amine-modified heterobifunctional poly(ethylene glycol) (NH$_2$-PEG-COOH) to form a copolymer of PLGA-PEG-COOH. By using an amine-modified low-molecular weight PSMA ligand (NH$_2$-Lig), a triblock polymer of PLGA-PEG-Lig may be formed by conjugating the carboxylic acid end of the PEG to the amine functional group on the ligand. The multiblock polymer can then be used, for instance, as discussed below, e.g., for therapeutic applications.

Nanoparticles

Disclosed nanoparticles may be stable (e.g., retain substantially all therapeutic agent) for example in a solution that may contain a saccharide, for at least about 3 days, about 4 days or at least about 5 days at room temperature, or at 25° C.

In some embodiments, disclosed nanoparticles may also include a fatty alcohol, which may increase the rate of drug release. For example, disclosed nanoparticles may include a $C_8$-$C_{30}$ alcohol such as cetyl alcohol, octanol, stearyl alcohol, arachidyl alcohol, docosanal, or octasonal.

Nanoparticles may have controlled release properties, e.g., may be capable of delivering an amount of a therapeutic agent to a patient, e.g., to specific site in a patient, over an extended period of time, e.g., over 1 day, 1 week, or more.

In some embodiments, after administration to a subject or patient of a disclosed nanoparticle or a composition that includes a disclosed nanoparticle, the peak plasma concentration ($C_{max}$) of the therapeutic agent in the patient is substantially higher as compared to a $C_{max}$ of the therapeutic agent if administered alone (e.g., not as part of a nanoparticle).

In another embodiment, a disclosed nanoparticle including a therapeutic agent, when administered to a subject, may have a $t_{max}$ of therapeutic agent substantially longer as compared to a $t_{max}$ of the therapeutic agent administered alone.

Libraries of such particles may also be formed. For example, by varying the ratios of the two (or more) polymers within the particle, these libraries can be useful for screening tests, high-throughput assays, or the like. Entities within the library may vary by properties such as those described above, and in some cases, more than one property of the particles may be varied within the library. Accordingly, one embodiment is directed to a library of nanoparticles having different ratios of polymers with differing properties. The library may include any suitable ratio(s) of the polymers.

In some embodiments, the biocompatible polymer is a hydrophobic polymer. Non-limiting examples of biocompatible polymers include polylactide, polyglycolide, and/or poly(lactide-co-glycolide).

In a different embodiment, this disclosure provides for a nanoparticle comprising 1) a polymeric matrix; 2) optionally, an amphiphilic compound or layer that surrounds or is dispersed within the polymeric matrix forming a continuous or discontinuous shell for the particle; 3) a non-functionalized polymer that may form part of the polymeric matrix, and 4) optionally, a low molecular weight ligand that binds to a target protein conjugate such as PSMA, covalently attached to a polymer, which may form part of the polymeric matrix. For example, an amphiphilic layer may reduce water penetration into the nanoparticle, thereby enhancing drug encapsulation efficiency and slowing drug release.

As used herein, the term "amphiphilic" refers to a property where a molecule has both a polar portion and a non-polar portion. Often, an amphiphilic compound has a polar head attached to a long hydrophobic tail. In some embodiments, the polar portion is soluble in water, while the non-polar portion is insoluble in water. In addition, the polar portion may have either a formal positive charge, or a formal negative charge. Alternatively, the polar portion may have both a formal positive and a negative charge, and be a zwitterion or inner salt. In some embodiments, the amphiphilic compound can be, but is not limited to, one or a plurality of the following: naturally derived lipids, surfactants, or synthesized compounds with both hydrophilic and hydrophobic moieties.

Specific examples of amphiphilic compounds include, but are not limited to, phospholipids, such as 1,2 distearoyl-sn-glycero-3-phosphoethanolamine (DSPE), dipalmitoylphosphatidylcholine (DPPC), distearoylphosphatidylcholine (DSPC), diarachidoylphosphatidylcholine (DAPC), dibehenoylphosphatidylcholine (DBPC), ditricosanoylphosphatidylcholine (DTPC), and dilignoceroylphatidylcholine (DLPC), incorporated at a ratio of between 0.01-60 (weight lipid/w polymer), most preferably between 0.1-30 (weight lipid/w polymer). Phospholipids which may be used include, but are not limited to, phosphatidic acids, phosphatidyl cholines with both saturated and unsaturated lipids, phosphatidyl ethanolamines, phosphatidylglycerols, phosphatidylserines, phosphatidylinositols, lysophosphatidyl derivatives, cardiolipin, and β-acyl-y-alkyl phospholipids. Examples of phospholipids include, but are not limited to, phosphatidylcholines such as dioleoylphosphatidylcholine, dimyristoylphosphatidylcholine, dipentadecanoylphosphatidylcholine dilauroylphosphatidylcholine, dipalmitoylphosphatidylcholine (DPPC), distearoylphosphatidylcholine (DSPC), diarachidoylphosphatidylcholine (DAPC), dibehenoylphosphatidylcholine (DBPC), ditricosanoylphosphatidylcholine (DTPC), dilignoceroylphatidylcholine (DLPC); and phosphatidylethanolamines such as dioleoylphosphatidylethanolamine or 1-hexadecyl-2-palmitoylglycerophosphoethanolamine. Synthetic phospholipids with asymmetric acyl chains (e.g., with one acyl chain of 6 carbons and another acyl chain of 12 carbons) may also be used.

In a particular embodiment, an amphiphilic component that can be used to form an amphiphilic layer is lecithin, and, in particular, phosphatidylcholine. Lecithin is an amphiphilic lipid and, as such, forms a phospholipid bilayer having the hydrophilic (polar) heads facing their surroundings, which are oftentimes aqueous, and the hydrophobic tails facing each other. Lecithin has an advantage of being a natural lipid that is available from, e.g., soybean, and already has FDA approval for use in other delivery devices. In addition, a mixture of lipids such as lethicin is more advantageous than one single pure lipid.

In certain embodiments a disclosed nanoparticle has an amphiphilic monolayer, meaning the layer is not a phospholipid bilayer, but exists as a single continuous or discontinuous layer around, or within, the nanoparticle. The amphiphilic layer is "associated with" the nanoparticle, meaning it is positioned in some proximity to the polymeric matrix, such as surrounding the outside of the polymeric shell, or dispersed within the polymers that make up the nanoparticle.

Preparation of Nanoparticles

Another aspect of this disclosure is directed to systems and methods of making disclosed nanoparticles. In some embodiments, using two or more different polymers (e.g., copolymers, e.g., block copolymers) in different ratios and producing particles from the polymers (e.g., copolymers, e.g., block copolymers), properties of the particles be controlled. For example, one polymer (e.g., copolymer, e.g., block copolymer) may include a low-molecular weight PSMA ligand, while another polymer (e.g., copolymer, e.g., block copolymer) may be chosen for its biocompatibility and/or its ability to control immunogenicity of the resultant particle.

In some embodiments, a solvent used in a nanoparticle preparation process (e.g., a nanoprecipitation process or a nanoemulsion process as discussed below) may include an acid, which may confer advantageous properties to the nanoparticles prepared using the process. As discussed above, in some cases, the acid may improve drug loading of disclosed nanoparticles. Furthermore, in some instances, the controlled release properties of disclosed nanoparticles may be improved by the use of the acid. In some cases, the acid may be included in for example, an organic solution or an aqueous solution used in the process. In one embodiment, the drug (i.e., therapeutic agent) is combined with an organic solution and the acid and optionally one or more polymers. The acid concentration in a solution used to dissolve the drug may be, for example, between about 0.5 weight percent and about 10 weight percent, between about 2 weight percent and about 10 weight percent, between about 5 weight percent and about 10 weight percent, between about 1.5 weight percent and about 5 weight percent, between about 2 weight percent and about 5 weight percent, or between about 2.5 weight percent and about 3.5 weight percent. In one embodiment, the acid concentration in the organic solution may be at least about 3 weight percent. In certain embodiments, the concentration of acid in a drug solution may be at least about 1 weight percent, in some embodiments at least about 2 weight percent, in some embodiments at least about 3 weight percent, in some embodiments at least about 10 weight percent.

In one set of embodiments, the particles are formed by providing a solution comprising one or more polymers, and contacting the solution with a polymer nonsolvent to produce the particle. The solution may be miscible or immiscible with the polymer nonsolvent. For example, a water-miscible liquid such as acetonitrile may contain the polymers, and particles are formed as the acetonitrile is contacted with water, a polymer nonsolvent, e.g., by pouring the acetonitrile into the water at a controlled rate. The polymer contained within the solution, upon contact with the polymer nonsolvent, may then precipitate to form particles such as nanoparticles. Two liquids are said to be "immiscible" or not miscible, with each other when one is not soluble in the other to a level of at least 10% by weight at ambient temperature and pressure. Typically, an organic solution (e.g., dichloromethane, acetonitrile, chloroform, tetrahydrofuran, acetone, formamide, dimethylformamide, pyridines, dioxane, dimethylsulfoxide, etc.) and an aqueous liquid (e.g., water, or water containing dissolved salts or other species, cell or biological media, ethanol, etc.) are immiscible with respect to each other. For example, the first solution may be poured into the second solution (at a suitable rate or speed). In some cases, particles such as nanoparticles may be formed as the first solution contacts the immiscible second liquid, e.g., precipitation of the polymer upon contact causes the polymer to form nanoparticles while the first solution is poured into the second liquid, and in some cases, for example, when the rate of introduction is carefully controlled and kept at a relatively slow rate, nanoparticles may form. The control of such particle formation can be readily optimized by one of ordinary skill in the art using only routine experimentation.

Properties such as surface functionality, surface charge, size, zeta (ζ) potential, hydrophobicity, ability to control immunogenicity, and the like, may be highly controlled using a disclosed process. For instance, a library of particles may be synthesized, and screened to identify the particles having a particular ratio of polymers that allows the particles to have a specific density of moieties (e.g., low-molecular weight PSMA ligands) present on the surface of the particle. This allows particles having one or more specific properties to be prepared, for example, a specific size and a specific surface density of moieties, without an undue degree of effort. Accordingly, certain embodiments are directed to screening techniques using such libraries, as well as any particles identified using such libraries. In addition, identification may occur by any suitable method. For instance, the identification may be direct or indirect, or proceed quantitatively or qualitatively.

In some embodiments, already-formed nanoparticles are functionalized with a targeting moiety using procedures analogous to those described for producing ligand-functionalized polymeric conjugates. For example, a first copolymer (PLGA-PEG, poly(lactide-co-glycolide) and poly(ethylene glycol)) is mixed with the therapeutic agent to form particles. The particles are then associated with a low-molecular weight ligand to form nanoparticles that can be used for the treatment of cancer. The particles can be associated with varying amounts of low-molecular weight ligands in order to control the ligand surface density of the nanoparticle, thereby altering the therapeutic characteristics of the nanoparticle. Furthermore, for example, by controlling parameters such as molecular weight, the molecular weight of PEG, and the nanoparticle surface charge, very precisely controlled particles may be obtained.

Figure 2:
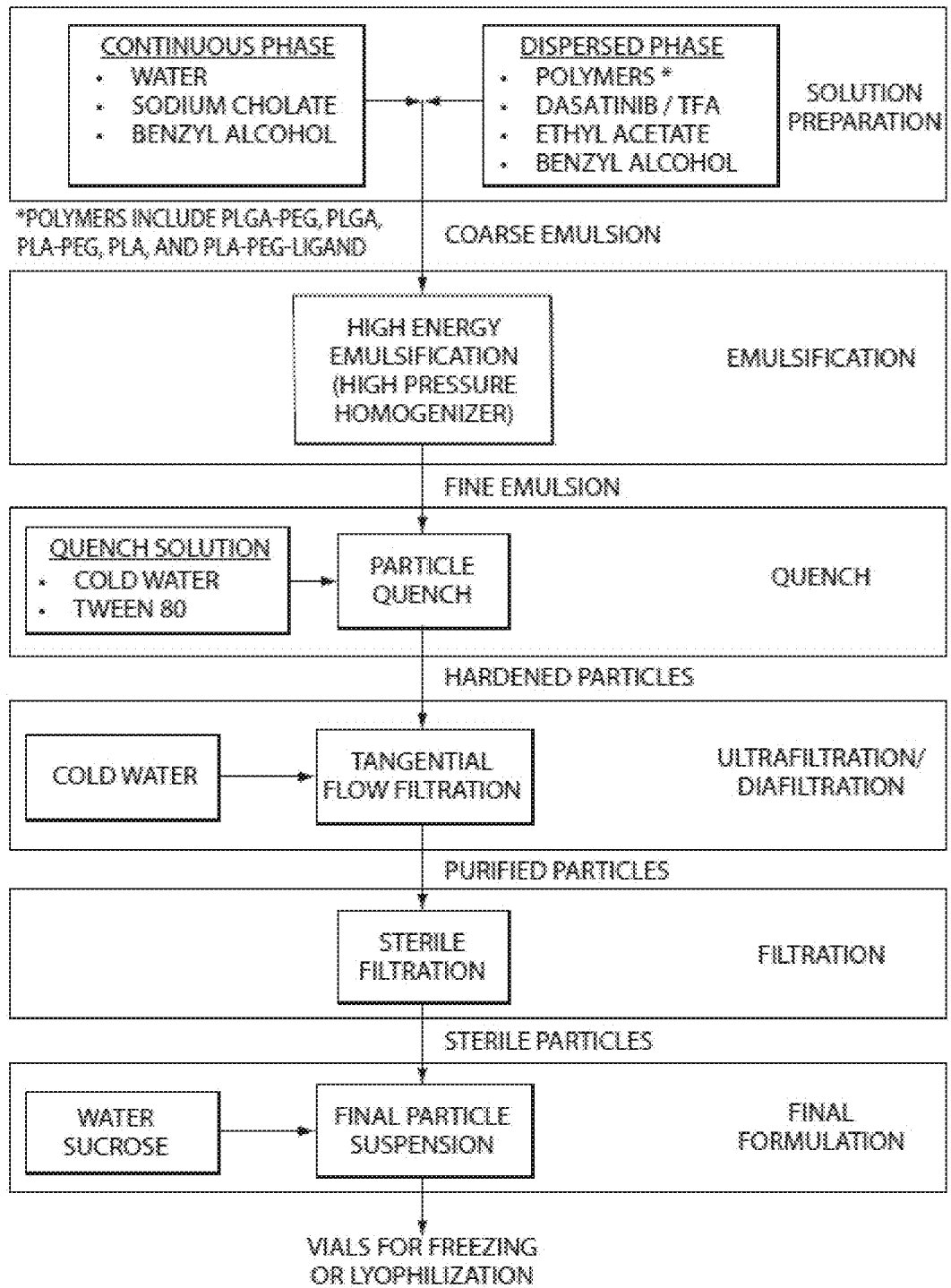
FIG. 2 is flow chart for an emulsion process for forming a disclosed nanoparticle.
Figure 3A:
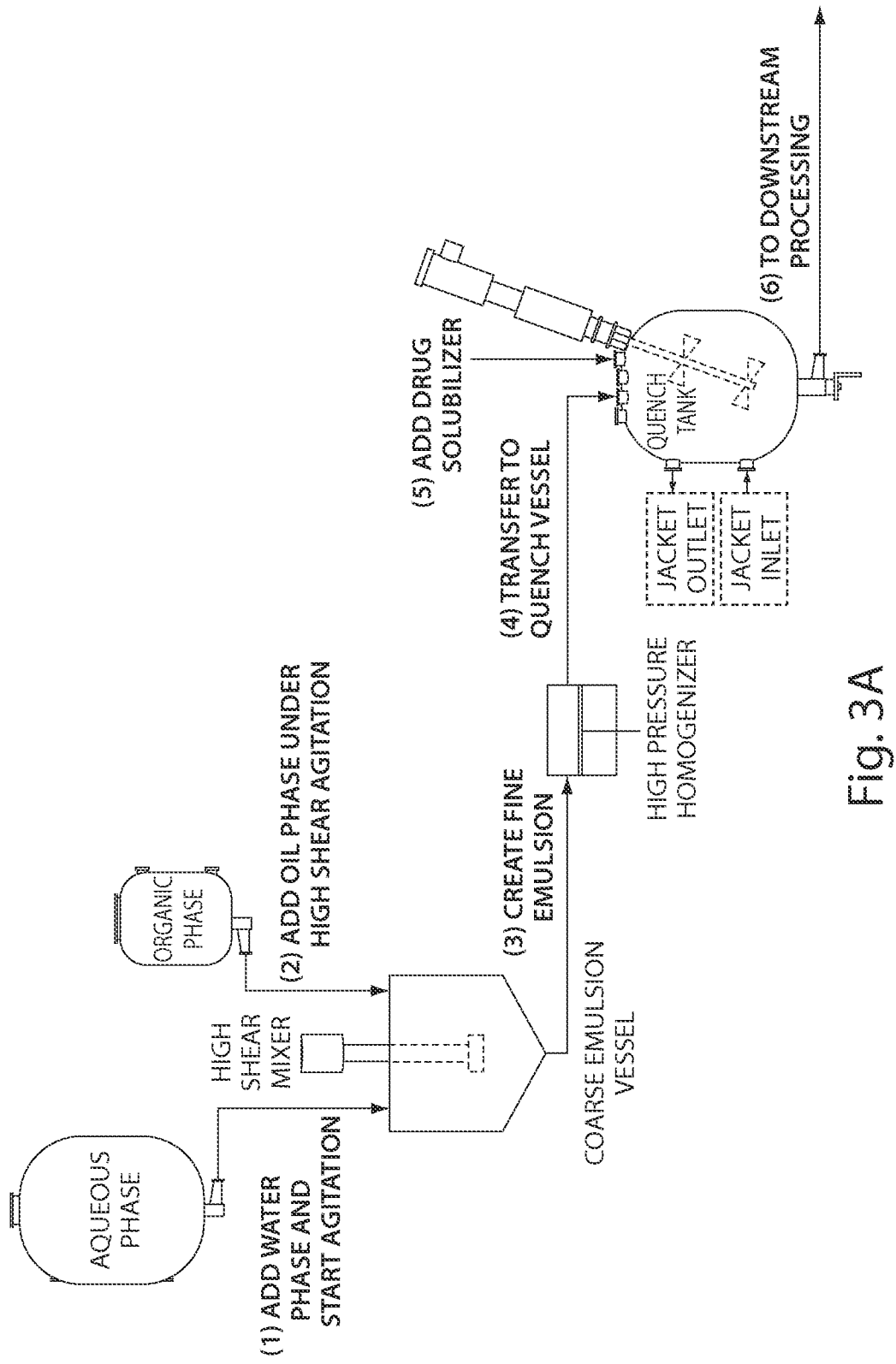
FIG. 3A is a flow diagram for a disclosed emulsion process.
Figure 3B:
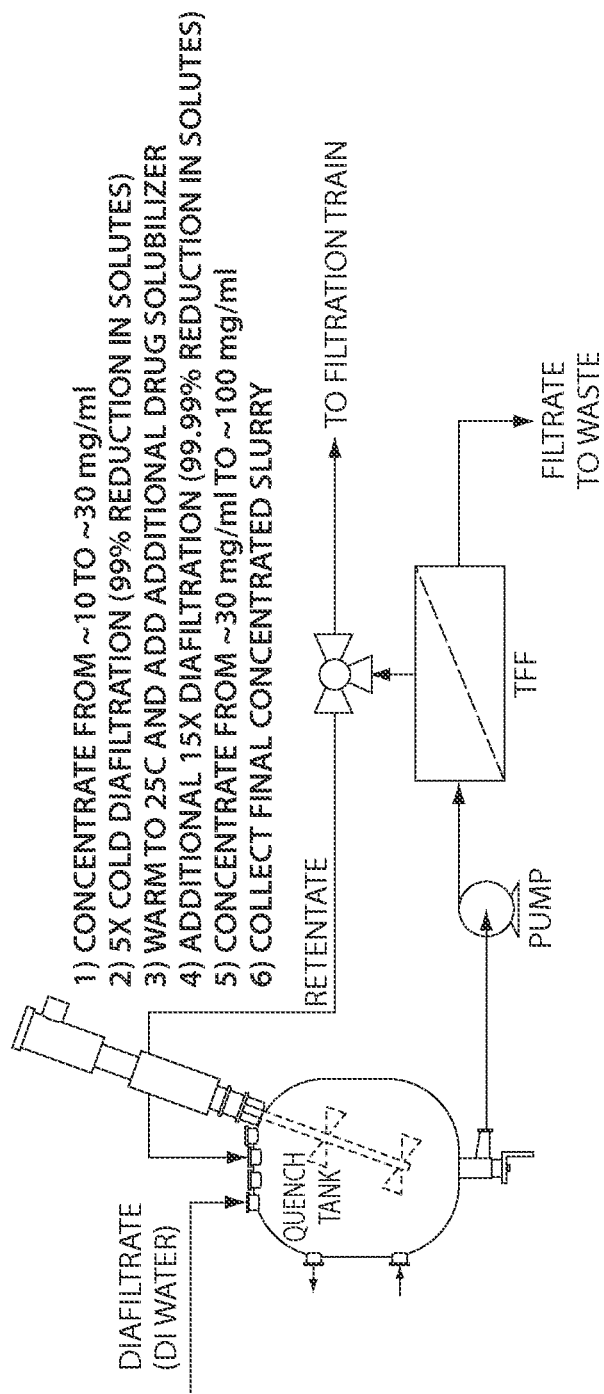
FIG. 3B is a flow diagram for a disclosed emulsion process.

In another embodiment, a nanoemulsion process is provided, such as the process represented in FIGS. 2, 3A, and 3B. For example, a therapeutic agent, an acid, a first polymer (for example, a diblock co-polymer such as PLA-PEG or PLGA-PEG, either of which may be optionally bound to a ligand) and an optional second polymer (e.g., (PL(G)A-PEG or PLA), may be combined with an organic solution to form a first organic phase. Such first phase may include about 1 to about 50% weight solids, about 5 to about 50% weight solids, about 5 to about 40% weight solids, about 1 to about 15% weight solids, or about 10 to about 30% weight solids. The first organic phase may be combined with a first aqueous solution to form a second phase. The organic solution can include, for example, toluene, methyl ethyl ketone, acetonitrile, tetrahydrofuran, ethyl acetate, isopropyl alcohol, isopropyl acetate, dimethylformamide, methylene chloride, dichloromethane, chloroform, acetone, benzyl alcohol, Tween 80, Span 80, or the like, and combinations thereof. In an embodiment, the organic phase may include benzyl alcohol, ethyl acetate, and combinations thereof. The second phase can be between about 0.1 and 50 weight %, between about 1 and 50 weight %, between about 5 and 40 weight %, or between about 1 and 15 weight %, solids. The aqueous solution can be water, optionally in combination with one or more of sodium cholate, ethyl acetate, polyvinyl acetate and benzyl alcohol.

For example, the oil or organic phase may use a solvent that is only partially miscible with the nonsolvent (water). Therefore, when mixed at a low enough ratio and/or when using water pre-saturated with the organic solvents, the oil phase remains liquid. The oil phase may be emulsified into an aqueous solution and, as liquid droplets, sheared into nanoparticles using, for example, high energy dispersion systems, such as homogenizers or sonicators. The aqueous portion of the emulsion, otherwise known as the "water phase", may be a surfactant solution consisting of sodium cholate and pre-saturated with ethyl acetate and benzyl alcohol.

Emulsifying the second phase to form an emulsion phase may be performed, for example, in one or two emulsification steps. For example, a primary emulsion may be prepared, and then emulsified to form a fine emulsion. The primary emulsion can be formed, for example, using simple mixing, a high pressure homogenizer, probe sonicator, stir bar, or a rotor stator homogenizer. The primary emulsion may be formed into a fine emulsion through the use of e.g., probe sonicator or a high pressure homogenizer, e.g., by using 1, 2, 3, or more passes through a homogenizer. For example, when a high pressure homogenizer is used, the pressure used may be about 1000 to about 8000 psi, about 2000 to about 4000 psi, about 4000 to about 8000 psi, or about 4000 to about 5000 psi, e.g., about 2000, 2500, 4000 or 5000 psi.

Either solvent evaporation or dilution may be needed to complete the extraction of the solvent and solidify the particles. For better control over the kinetics of extraction and a more scalable process, a solvent dilution via aqueous quench may be used. For example, the emulsion can be diluted into cold water to a concentration sufficient to dissolve all of the organic solvent to form a quenched phase. In some embodiments, quenching may be performed at least partially at a temperature of about 5° C. or less. For example, water used in the quenching may be at a temperature that is less that room temperature (e.g., about 0 to about 10° C., or about 0 to about 5° C.).

In some embodiments, not all of the therapeutic agent is encapsulated in the particles at this stage, and a drug solubilizer is added to the quenched phase to form a solubilized phase. The drug solubilizer may be for example, Tween 80, Tween 20, polyvinyl pyrrolidone, cyclodextran, sodium dodecyl sulfate, sodium cholate, diethylnitrosamine, sodium acetate, urea, glycerin, propylene glycol, glycofurol, poly(ethylene)glycol, bris(polyoxyethyleneglycolddodecyl ether, sodium benzoate, sodium salicylate, or combinations thereof. For example, Tween-80 may be added to the quenched nanoparticle suspension to solubilize the free drug and prevent the formation of drug crystals. In some embodiments, a ratio of drug solubilizer to the therapeutic agent is about 200:1 to about 10:1, or in some embodiments about 100:1 to about 10:1.

The solubilized phase may be filtered to recover the nanoparticles. For example, ultrafiltration membranes may be used to concentrate the nanoparticle suspension and substantially eliminate organic solvent, free drug (i.e., unencapsulated therapeutic agent), drug solubilizer, and other processing aids (surfactants). Exemplary filtration may be performed using a tangential flow filtration system. For example, by using a membrane with a pore size suitable to retain nanoparticles while allowing solutes, micelles, and organic solvent to pass, nanoparticles can be selectively separated. Exemplary membranes with molecular weight cut-offs of about 300-500 kDa (~5-25 nm) may be used.

Diafiltration may be performed using a constant volume approach, meaning the diafiltrate (cold deionized water, e.g., about 0 to about 5° C., or 0 to about 10° C.) may added to the feed suspension at the same rate as the filtrate is removed from the suspension. In some embodiments, filtering may include a first filtering using a first temperature of about 0 to about 5° C., or 0 to about 10° C., and a second temperature of about 20 to about 30° C., or 15 to about 35° C. In some embodiments, filtering may include processing about 1 to about 30, in some cases about 1 to about 15, or in some cases 1 to about 6 diavolumes. For example, filtering may include processing about 1 to about 30, or in some cases about 1 to about 6 diavolumes, at about 0 to about 5° C., and processing at least one diavolume (e.g., about 1 to about 15, about 1 to about 3, or about 1 to about 2 diavolumes) at about 20 to about 30° C. In some embodiments, filtering comprises processing different diavolumes at different distinct temperatures.

After purifying and concentrating the nanoparticle suspension, the particles may be passed through one, two or more sterilizing and/or depth filters, for example, using ~0.2 μm depth pre-filter. For example, a sterile filtration step may involve filtering the therapeutic nanoparticles using a filtration train at a controlled rate. In some embodiments, the filtration train may include a depth filter and a sterile filter.

In another embodiment of preparing nanoparticles, an organic phase is formed composed of a mixture of a therapeutic agent, an acid, and polymer (homopolymer, co-polymer, and co-polymer with ligand). The organic phase is mixed with an aqueous phase at approximately a 1:5 ratio (oil phase:aqueous phase) where the aqueous phase is composed of a surfactant and some dissolved solvent. The primary emulsion is formed by the combination of the two phases under simple mixing or through the use of a rotor stator homogenizer. The primary emulsion is then formed into a fine emulsion through the use of a high pressure homogenizer. The fine emulsion is then quenched by addition to deionized water under mixing. In some embodiments, the quench:emulsion ratio may be about 2:1 to about 40:1, or in some embodiments about 5:1 to about 15:1. In some embodiments, the quench:emulsion ratio is approximately 8.5:1. Then a solution of Tween (e.g., Tween 80) is added to the quench to achieve approximately 2% Tween overall. This serves to dissolve free, unencapsulated therapeutic agent. The nanoparticles are then isolated through either centrifugation or ultrafiltration/diafiltration.

It will be appreciated that the amounts of polymer, therapeutic agent, and acid that are used in the preparation of the formulation may differ from a final formulation. For example, some of the therapeutic agent may not become completely incorporated in a nanoparticle and such free therapeutic agent may be e.g., filtered away. For example, in an embodiment, about 30 weight percent of therapeutic agent and about 70 weight percent polymer (e.g., the polymer may include about 2.5 mol percent of a targeting moiety conjugated to a polymer and about 97.5 mol percent PLA-PEG) in an organic solution containing about 1% acid may be used in the preparation of a formulation that results in, e.g., a final nanoparticle comprising about 2.5 weight percent therapeutic agent, about 97.5 weight percent polymer (where the polymer may include about 1.25 mol percent of a targeting moiety conjugated to a polymer and about 98.75 mol percent PLA-PEG), and less than about 0.5% acid. Such processes may provide final nanoparticles suitable for administration to a patient that includes about 1 to about 20 percent by weight therapeutic agent, e.g., about 1, about 2, about 3, about 4, about 5, about 8, about 10, or about 15 percent therapeutic agent by weight.

Therapeutic Agents

As discussed above, the disclosed processes may be used to formulate any suitable therapeutic agent in nanoparticles. Such particles may be useful, for example, in embodiments where a targeting moiety may be used to direct a particle containing a drug to a particular localized location within a subject, e.g., to allow localized delivery of the drug to occur. In one set of embodiments, a combination of more than one therapeutic agents may be used. Exemplary therapeutic agents include chemotherapeutic agents such Bcr-Abl tyrosine-kinase inhibitors (e.g., imatinib, nilotinib, dasatinib, bosutinib, ponatinib, and bafetinib), doxorubicin (adriamycin), gemcitabine (gemzar), daunorubicin, procarbazine, mitomycin, cytarabine, etoposide, methotrexate, venorelbine, 5-fluorouracil (5-FU), vinca alkaloids such as vinblastine or vincristine; bleomycin, paclitaxel (taxol), docetaxel (taxotere), cabazitaxel, aldesleukin, asparaginase, busulfan, carboplatin, cladribine, camptothecin, CPT-11,10-hydroxy-7-ethylcamptothecin (SN38), dacarbazine, S-I capecitabine, ftorafur, 5' deoxyfluorouridine, UFT, eniluracil, deoxycytidine, 5-azacytosine, 5-azadeoxycytosine, allopurinol, 2-chloroadenosine, trimetrexate, aminopterin, methylene-10-deazaminopterin (MDAM), oxaplatin, picoplatin, tetraplatin, satraplatin, platinum-DACH, ormaplatin, CI-973, JM-216, and analogs thereof, epirubicin, etoposide phosphate, 9-aminocamptothecin, 10,11-methylenedioxycamptothecin, karenitecin, 9-nitrocamptothecin, TAS 103, vindesine, L-phenylalanine mustard, ifosphamidemefosphamide, perfosfamide, trophosphamide carmustine, semustine, epothilones A-E, tomudex, 6-mercaptopurine, 6-thioguanine, amsacrine, etoposide phosphate, karenitecin, acyclovir, valacyclovir, ganciclovir, amantadine, rimantadine, lamivudine, zidovudine, bevacizumab, trastuzumab, rituximab, 5-Fluorouracil, and combinations thereof.

Non-limiting examples of potentially suitable combination drugs include anti-cancer agents, including, for example, cabazitaxel, mitoxantrone, and mitoxantrone hydrochloride. In another embodiment, the payload may be an anti-cancer drug such as 20-epi-1, dihydroxyvitamin D3,4-ipomeanol, 5-ethynyluracil, 9-dihydrotaxol, abiraterone, acivicin, aclarubicin, acodazole hydrochloride, acronine, acylfiilvene, adecypenol, adozelesin, aldesleukin, all-tk antagonists, altretamine, ambamustine, ambomycin, ametantrone acetate, amidox, amifostine, aminoglutethimide, aminolevulinic acid, amrubicin, amsacrine, anagrelide, anastrozole, andrographolide, angiogenesis inhibitors, antagonist D, antagonist G, antarelix, anthramycin, anti-dorsalizdng morphogenetic protein-1, antiestrogen, antineoplaston, antisense oligonucleotides, aphidicolin glycinate, apoptosis gene modulators, apoptosis regulators, apurinic acid, ARA-CDP-DL-PTBA, arginine deaminase, asparaginase, asperlin, asulacrine, atamestane, atrimustine, axinastatin 1, axinastatin 2, axinastatin 3, azacitidine, azasetron, azatoxin, azatyrosine, azetepa, azotomycin, baccatin III derivatives, balanol, batimastat, benzochlorins, benzodepa, benzoylstaurosporine, beta lactam derivatives, beta-alethine, betaclamycin B, betulinic acid, BFGF inhibitor, bicalutamide, bisantrene, bisantrene hydrochloride, bisazuidinyl-spermine, bisnafide, bisnafide dimesylate, bistratene A, bizelesin, bleomycin, bleomycin sulfate, BRC/ABL antagonists, breflate, brequinar sodium, bropirimine, budotitane, busulfan, buthionine sulfoximine, cactinomycin, calcipotriol, calphostin C, calusterone, camptothecin derivatives, canarypox IL-2, capecitabine, caraceraide, cabazitaxel, carbetimer, carboplatin, carboxamide-amino-triazole, carboxyamidotriazole, carest M3, carmustine, earn 700, cartilage derived inhibitor, carubicin hydrochloride, carzelesin, casein kinase inhibitors, castanosperrnine, cecropin B, cedefingol, cetrorelix, chlorambucil, chlorins, chloroquinoxaline sulfonamide, cicaprost, cirolemycin, cisplatin, cis-porphyrin, cladribine, clomifene analogs, clotrimazole, collismycin A, collismycin B, combretastatin A4, combretastatin analog, conagenin, crambescidin 816, crisnatol, crisnatol mesylate, cryptophycin 8, cryptophycin A derivatives, curacin A, cyclopentanthraquinones, cyclophosphamide, cycloplatam, cypemycin, cytarabine, cytarabine ocfosfate, cytolytic factor, cytostatin, dacarbazine, dacliximab, dactinomycin, daunorubicin hydrochloride, decitabine, dehydrodidemnin B, deslorelin, dexifosfamide, dexormaplatin, dexrazoxane, dexverapamil, dezaguanine, dezaguanine mesylate, diaziquone, didemnin B, didox, diethyhiorspermine, dihydro-5-azacytidine, dioxamycin, diphenyl spiromustine, docetaxel, docosanol, dolasetron, doxifluridine, doxorubicin, doxorubicin hydrochloride, droloxifene, droloxifene citrate, dromostanolone propionate, dronabinol, duazomycin, duocannycin SA, ebselen, ecomustine, edatrexate, edelfosine, edrecolomab, eflomithine, eflomithine hydrochloride, elemene, elsarnitrucin, emitefur, enloplatin, enpromate, epipropidine, epirubicin, epirubicin hydrochloride, episteride, erbulozole, erythrocyte gene therapy vector system, esorubicin hydrochloride, estramustine, estramustine analog, estramustine phosphate sodium, estrogen agonists, estrogen antagonists, etanidazole, etoposide, etoposide phosphate, etoprine, exemestane, fadrozole, fadrozole hydrochloride, fazarabine, fenretinide, filgrastim, finasteride, flavopiridol, flezelastine, floxuridine, fluasterone, fludarabine, fludarabine phosphate, fluorodaunorunicin hydrochloride, fluorouracil, fluorocitabine, forfenimex, formestane, fosquidone, fostriecin, fostriecin sodium, fotemustine, gadolinium texaphyrin, gallium nitrate, galocitabine, ganirelix, gelatinase inhibitors, gemcitabine, gemcitabine hydrochloride, glutathione inhibitors, hepsulfam, heregulin, hexamethylene bisacetamide, hydroxyurea, hypericin, ibandronic acid, idarubicin, idarubicin hydrochloride, idoxifene, idramantone, ifosfamide, ihnofosine, ilomastat, imidazoacridones, imiquimod, immunostimulant peptides, insulin-like growth factor-1 receptor inhibitor, interferon agonists, interferon alpha-2A, interferon alpha-2B, interferon alpha-N1, interferon alpha-N3, interferon beta-IA, interferon gamma-IB, interferons, interleukins, iobenguane, iododoxorubicin, iproplatm, irinotecan, irinotecan hydrochloride, iroplact, irsogladine, isobengazole, isohomohalicondrin B, itasetron, jasplakinolide, kahalalide F, lamellarin-N triacetate, lanreotide, lanreotide acetate, leinamycin, lenograstim, lentinan sulfate, leptolstatin, letrozole, leukemia inhibiting factor, leukocyte alpha interferon, leuprolide acetate, leuprolide/estrogen/progesterone, leuprorelin, levamisole, liarozole, liarozole hydrochloride, linear polyamine analog, lipophilic disaccharide peptide, lipophilic platinum compounds, lissoclinamide, lobaplatin, lombricine, lometrexol, lometrexol sodium, lomustine, lonidamine, losoxantrone, losoxantrone hydrochloride, lovastatin, loxoribine, lurtotecan, lutetium texaphyrin lysofylline, lytic peptides, maitansine, mannostatin A, marimastat, masoprocol, maspin, matrilysin inhibitors, matrix metalloproteinase inhibitors, maytansine, mechlorethamine hydrochloride, megestrol acetate, melengestrol acetate, melphalan, menogaril, merbarone, mercaptopurine, meterelin, methioninase, methotrexate, methotrexate sodium, metoclopramide, metoprine, meturedepa, microalgal protein kinase C inhibitors, MIF inhibitor, mifepristone, miltefosine, mirimostim, mismatched double stranded RNA, mitindomide, mitocarcin, mitocromin, mitogillin, mitoguazone, mitolactol, mitomalcin, mitomycin, mitomycin analogs, mitonafide, mitosper, mitotane, mitotoxin fibroblast growth factor-saporin, mitoxantrone, mitoxantrone hydrochloride, mofarotene, molgramostim, monoclonal antibody, human chorionic gonadotrophin, monophosphoryl lipid a/myobacterium cell wall SK, mopidamol, multiple drug resistance gene inhibitor, multiple tumor suppressor 1-based therapy, mustard anticancer agent, mycaperoxide B, mycobacterial cell wall extract, mycophenolic acid, myriaporone, n-acetyldinaline, nafarelin, nagrestip, naloxone/pentazocine, napavin, naphterpin, nartograstim, nedaplatin, nemorubicin, neridronic acid, neutral endopeptidase, nilutamide, nisamycin, nitric oxide modulators, nitroxide antioxidant, nitrullyn, nocodazole, nogalamycin, n-substituted benzamides, O6-benzylguanine, octreotide, okicenone, oligonucleotides, onapristone, ondansetron, oracin, oral cytokine inducer, ormaplatin, osaterone, oxaliplatin, oxaunomycin, oxisuran, paclitaxel, paclitaxel analogs, paclitaxel derivatives, palauamine, palmitoylrhizoxin, pamidronic acid, panaxytriol, panomifene, parabactin, pazelliptine, pegaspargase, peldesine, peliomycin, pentamustine, pentosan polysulfate sodium, pentostatin, pentrozole, peplomycin sulfate, perflubron, perfosfamide, perillyl alcohol, phenazinomycin, phenylacetate, phosphatase inhibitors, picibanil, pilocarpine hydrochloride, pipobroman, piposulfan, pirarubicin, piritrexim, piroxantrone hydrochloride, placetin A, placetin B, plasminogen activator inhibitor, platinum complex, platinum compounds, platinum-triamine complex, plicamycin, plomestane, porfimer sodium, porfiromycin, prednimustine, procarbazine hydrochloride, propyl bis-acridone, prostaglandin J2, prostatic carcinoma antiandrogen, proteasome inhibitors, protein A-based immune modulator, protein kinase C inhibitor, protein tyrosine phosphatase inhibitors, purine nucleoside phosphorylase inhibitors, puromycin, puromycin hydrochloride, purpurins, pyrazorurin, pyrazoloacridine, pyridoxylated hemoglobin polyoxyethylene conjugate, RAF antagonists, raltitrexed, ramosetron, RAS farnesyl protein transferase inhibitors, RAS inhibitors, RAS-GAP inhibitor, retelliptine demethylated, rhenium RE 186 etidronate, rhizoxin, riboprine, ribozymes, RH retinamide, RNAi, rogletimide, rohitukine, romurtide, roquinimex, rubiginone B1, ruboxyl, safingol, safingol hydrochloride, saintopin, sarcnu, sarcophytol A, sargramostim, SDI1 mimetics, semustine, senescence derived inhibitor 1, sense oligonucleotides, signal transduction inhibitors, signal transduction modulators, simtrazene, single chain antigen binding protein, sizofiran, sobuzoxane, sodium borocaptate, sodium phenylacetate, solverol, somatomedin binding protein, sonermin, sparfosafe sodium, sparfosic acid, sparsomycin, spicamycin D, spirogermanium hydrochloride, spiromustine, spiroplatin, splenopentin, spongistatin 1, squalamine, stem cell inhibitor, stem-cell division inhibitors, stipiamide, streptonigrin, streptozocin, stromelysin inhibitors, sulfinosine, sulofenur, superactive vasoactive intestinal peptide antagonist, suradista, suramin, swainsonine, synthetic glycosaminoglycans, talisomycin, tallimustine, tamoxifen methiodide, tauromustine, tazarotene, tecogalan sodium, tegafur, tellurapyrylium, telomerase inhibitors, teloxantrone hydrochloride, temoporfin, temozolomide, teniposide, teroxirone, testolactone, tetrachlorodecaoxide, tetrazomine, thaliblastine, thalidomide, thiamiprine, thiocoraline, thioguanine, thiotepa, thrombopoietin, thrombopoietin mimetic, thymalfasin, thymopoietin receptor agonist, thymotrinan, thyroid stimulating hormone, tiazofurin, tin ethyl etiopurpurin, tirapazamine, titanocene dichloride, topotecan hydrochloride, topsentin, toremifene, toremifene citrate, totipotent stem cell factor, translation inhibitors, trestolone acetate, tretinoin, triacetyluridine, triciribine, triciribine phosphate, trimetrexate, trimetrexate glucuronate, triptorelin, tropisetron, tubulozole hydrochloride, turosteride, tyrosine kinase inhibitors, tyrphostins, UBC inhibitors, ubenimex, uracil mustard, uredepa, urogenital sinus-derived growth inhibitory factor, urokinase receptor antagonists, vapreotide, variolin B, velaresol, veramine, verdins, verteporfin, vinblastine sulfate, vincristine sulfate, vindesine, vindesine sulfate, vinepidine sulfate, vinglycinate sulfate, vinleurosine sulfate, vinorelbine or vinorelbine tartrate, vinrosidine sulfate, vinxaltine, vinzolidine sulfate, vitaxin, vorozole, zanoterone, zeniplatin, zilascorb, zinostatin, zinostatin stimalamer, or zorubicin hydrochloride.

Pharmaceutical Formulations

Nanoparticles disclosed herein may be combined with pharmaceutically acceptable carriers to form a pharmaceutical composition, according to another aspect. As would be appreciated by one of skill in this art, the carriers may be chosen based on the route of administration as described below, the location of the target issue, the drug being delivered, the time course of delivery of the drug, etc.

The pharmaceutical compositions can be administered to a patient by any means known in the art including oral and parenteral routes. The term "patient," as used herein, refers to humans as well as non-humans, including, for example, mammals, birds, reptiles, amphibians, and fish. For instance, the non-humans may be mammals (e.g., a rodent, a mouse, a rat, a rabbit, a monkey, a dog, a cat, a primate, or a pig). In certain embodiments parenteral routes are desirable since they avoid contact with the digestive enzymes that are found in the alimentary canal. According to such embodiments, inventive compositions may be administered by injection (e.g., intravenous, subcutaneous or intramuscular, intraperitoneal injection), rectally, vaginally, topically (as by powders, creams, ointments, or drops), or by inhalation (as by sprays).

In a particular embodiment, the nanoparticles are administered to a subject in need thereof systemically, e.g., by IV infusion or injection.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension, or emulsion in a nontoxic parenterally acceptable diluent or solvent, for example, as a solution in 1,3-butanediol. Among the acceptable vehicles and solvents that may be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. In one embodiment, the inventive conjugate is suspended in a carrier fluid comprising 1% (w/v) sodium carboxymethyl cellulose and 0.1% (v/v) TWEEN™ 80. The injectable formulations can be sterilized, for example, by filtration through a bacteria-retaining filter, or by incorporating sterilizing agents in the form of sterile solid compositions which can be dissolved or dispersed in sterile water or other sterile injectable medium prior to use.

Solid dosage forms for oral administration include capsules, tablets, pills, powders, and granules. In such solid dosage forms, the encapsulated or unencapsulated conjugate is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar-agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may also comprise buffering agents.

It will be appreciated that the exact dosage of a nanoparticle containing a therapeutic agent is chosen by the individual physician in view of the patient to be treated, in general, dosage and administration are adjusted to provide an effective amount of the therapeutic agent nanoparticle to the patient being treated. As used herein, the "effective amount" of a nanoparticle containing a therapeutic agent refers to the amount necessary to elicit the desired biological response. As will be appreciated by those of ordinary skill in this art, the effective amount of a nanoparticle containing a therapeutic agent may vary depending on such factors as the desired biological endpoint, the drug to be delivered, the target tissue, the route of administration, etc. For example, the effective amount of a nanoparticle containing a therapeutic agent might be the amount that results in a reduction in tumor size by a desired amount over a desired period of time. Additional factors which may be taken into account include the severity of the disease state; age, weight and gender of the patient being treated; diet, time and frequency of administration; drug combinations; reaction sensitivities; and tolerance/response to therapy.

The nanoparticles may be formulated in dosage unit form for ease of administration and uniformity of dosage. The expression "dosage unit form" as used herein refers to a physically discrete unit of nanoparticle appropriate for the patient to be treated. It will be understood, however, that the total daily usage of the compositions will be decided by the attending physician within the scope of sound medical judgment. For any nanoparticle, the therapeutically effective dose can be estimated initially either in cell culture assays or in animal models, usually mice, rabbits, dogs, or pigs. The animal model is also used to achieve a desirable concentration range and route of administration. Such information can then be used to determine useful doses and routes for administration in humans. Therapeutic efficacy and toxicity of nanoparticles can be determined by standard pharmaceutical procedures in cell cultures or experimental animals, e.g., $ED_{50}$ (the dose is therapeutically effective in 50% of the population) and $LD_{50}$ (the dose is lethal to 50% of the population). The dose ratio of toxic to therapeutic effects is the therapeutic index, and it can be expressed as the ratio, $LD_{50}/ED_{50}$. Pharmaceutical compositions which exhibit large therapeutic indices may be useful in some embodiments. The data obtained from cell culture assays and animal studies can be used in formulating a range of dosage for human use.

In an embodiment, compositions disclosed herein may include less than about 10 ppm of palladium, or less than about 8 ppm, or less than about 6 ppm of palladium. For example, provided here is a composition that includes nanoparticles having a polymeric conjugate wherein the composition has less than about 10 ppm of palladium.

In some embodiments, a composition suitable for freezing is contemplated, including nanoparticles disclosed herein and a solution suitable for freezing, e.g., a sugar such as a mono, di, or poly saccharide, e.g. sucrose and/or a trehalose, and/or a salt and/or a cyclodextrin solution is added to the nanoparticle suspension. The sugar (e.g. sucrose or trehalose) may act, e.g., as a cryoprotectant to prevent the particles from aggregating upon freezing. For example, provided herein is a nanoparticle formulation comprising a plurality of disclosed nanoparticles, sucrose, an ionic halide, and water; wherein the nanoparticles/sucrose/water/ionic halide is about 3-40%/10-40%/20-95%/0.1-10% (w/w/w/w) or about 5-10%/10-15%/80-90%/1-10% (w/w/w/w). For example, such solution may include nanoparticles as disclosed herein, about 5% to about 20% by weight sucrose and an ionic halide such as sodium chloride, in a concentration of about 10-100 mM. In another example, provided herein is a nanoparticle formulation comprising a plurality of disclosed nanoparticles, trehalose, cyclodextrin, and water; wherein the nanoparticles/trehalose/water/cyclodextrin is about 3-40%/1-25%/20-95%/1-25% (w/w/w/w) or about 5-10%/1-25%/80-90%/10-15% (w/w/w/w).

For example, a contemplated solution may include nanoparticles as disclosed herein, about 1% to about 25% by weight of a disaccharide such as trehalose or sucrose (e.g. about 5% to about 25% trehalose or sucrose, e.g. about 10% trehalose or sucrose, or about 15% trehalose or sucrose, e.g. about 5% sucrose) by weight) and a cyclodextrin such as β-cyclodextrin, in a concentration of about 1% to about 25% by weight (e.g. about 5% to about 20%, e.g. 10% or about 20% by weight, or about 15% to about 20% by weight cyclodextrin). Contemplated formulations may include a plurality of disclosed nanoparticles (e.g. nanoparticles having PLA-PEG and an active agent), and about 2% to about 15 wt % (or about 4% to about 6 wt %, e.g. about 5 wt %)

sucrose and about 5 wt % to about 20% (e.g. about 7% wt percent to about 12 wt %, e.g. about 10 wt %) of a cyclodextrin, e.g., HPbCD).

The present disclosure relates in part to lyophilized pharmaceutical compositions that, when reconstituted, have a minimal amount of large aggregates. Such large aggregates may have a size greater than about 0.5 µm, greater than about 1 µm, or greater than about 10 µm, and can be undesirable in a reconstituted solution. Aggregate sizes can be measured using a variety of techniques including those indicated in the U.S. Pharmacopeia at 32 <788>, hereby incorporated by reference. The tests outlined in USP 32 <788> include a light obscuration particle count test, microscopic particle count test, laser diffraction, and single particle optical sensing. In one embodiment, the particle size in a given sample is measured using laser diffraction and/or single particle optical sensing.

The USP 32 <788> by light obscuration particle count test sets forth guidelines for sampling particle sizes in a suspension. For solutions with less than or equal to 100 mL, the preparation complies with the test if the average number of particles present does not exceed 6000 per container that are ≥10 µm and 600 per container that are ≥25 µm.

As outlined in USP 32 <788>, the microscopic particle count test sets forth guidelines for determining particle amounts using a binocular microscope adjusted to 100±10× magnification having an ocular micrometer. An ocular micrometer is a circular diameter graticule that consists of a circle divided into quadrants with black reference circles denoting 10 µm and 25 µm when viewed at 100× magnification. A linear scale is provided below the graticule. The number of particles with reference to 10 µm and 25 µm are visually tallied. For solutions with less than or equal to 100 mL, the preparation complies with the test if the average number of particles present does not exceed 3000 per container that are ≥10 µm and 300 per container that are ≥25 µm.

In some embodiments, a 10 mL aqueous sample of a disclosed composition upon reconstitution comprises less than 600 particles per ml having a size greater than or equal to 10 microns; and/or less than 60 particles per ml having a size greater than or equal to 25 microns.

Dynamic light scattering (DLS) may be used to measure particle size, but it relies on Brownian motion so the technique may not detect some larger particles. Laser diffraction relies on differences in the index of refraction between the particle and the suspension media. The technique is capable of detecting particles at the sub-micron to millimeter range. Relatively small (e.g., about 1-5 weight %) amounts of larger particles can be determined in nanoparticle suspensions. Single particle optical sensing (SPOS) uses light obscuration of dilute suspensions to count individual particles of about 0.5 µm. By knowing the particle concentration of the measured sample, the weight percentage of aggregates or the aggregate concentration (particles/mL) can be calculated.

Formation of aggregates can occur during lyophilization due to the dehydration of the surface of the particles. This dehydration can be avoided by using lyoprotectants, such as disaccharides, in the suspension before lyophilization. Suitable disaccharides include sucrose, lactulose, lactose, maltose, trehalose, or cellobiose, and/or mixtures thereof. Other contemplated disaccharides include kojibiose, nigerose, isomaltose, β,β-trehalose, α,β-trehalose, sophorose, laminaribiose, gentiobiose, turanose, maltulose, palatinose, gentiobiulose, mannobiose, melibiose, melibiulose, rutinose, rutinulose, and xylobiose. Reconstitution shows equivalent DLS size distributions when compared to the starting suspension. However, laser diffraction can detect particles of >10 µm in size in some reconstituted solutions. Further, SPOS also may detect >10 µm sized particles at a concentration above that of the FDA guidelines ($10^4$-$10^5$ particles/mL for >10 µm particles).

In some embodiments, one or more ionic halide salts may be used as an additional lyoprotectant to a sugar, such as sucrose, trehalose or mixtures thereof. Sugars may include disaccharides, monosaccharides, trisaccharides, and/or polysaccharides, and may include other excipients, e.g. glycerol and/or surfactants. Optionally, a cyclodextrin may be included as an additional lyoprotectant. The cyclodextrin may be added in place of the ionic halide salt. Alternatively, the cyclodextrin may be added in addition to the ionic halide salt.

Suitable ionic halide salts may include sodium chloride, calcium chloride, zinc chloride, or mixtures thereof. Additional suitable ionic halide salts include potassium chloride, magnesium chloride, ammonium chloride, sodium bromide, calcium bromide, zinc bromide, potassium bromide, magnesium bromide, ammonium bromide, sodium iodide, calcium iodide, zinc iodide, potassium iodide, magnesium iodide, or ammonium iodide, and/or mixtures thereof. In one embodiment, about 1 to about 15 weight percent sucrose may be used with an ionic halide salt. In one embodiment, the lyophilized pharmaceutical composition may comprise about 10 to about 100 mM sodium chloride. In another embodiment, the lyophilized pharmaceutical composition may comprise about 100 to about 500 mM of divalent ionic chloride salt, such as calcium chloride or zinc chloride. In yet another embodiment, the suspension to be lyophilized may further comprise a cyclodextrin, for example, about 1 to about 25 weight percent of cyclodextrin may be used.

A suitable cyclodextrin may include α-cyclodextrin, β-cyclodextrin, γ-cyclodextrin, or mixtures thereof. Exemplary cyclodextrins contemplated for use in the compositions disclosed herein include hydroxypropyl-β-cyclodextrin (HPbCD), hydroxyethyl-β-cyclodextrin, sulfobutylether-β-cyclodextrin, methyl-β-cyclodextrin, dimethyl-β-cyclodextrin, carboxymethyl-β-cyclodextrin, carboxymethyl ethyl-β-cyclodextrin, diethyl-β-cyclodextrin, tri-O-alkyl-β-cyclodextrin, glocosyl-β-cyclodextrin, and maltosyl-β-cyclodextrin. In one embodiment, about 1 to about 25 weight percent trehalose (e.g. about 10% to about 15%, e.g. 5 to about 20% by weight) may be used with cyclodextrin. In one embodiment, the lyophilized pharmaceutical composition may comprise about 1 to about 25 weight percent β-cyclodextrin. An exemplary composition may comprise nanoparticles comprising PLA-PEG, an active/therapeutic agent, about 4% to about 6% (e.g. about 5% wt percent) sucrose, and about 8 to about 12 weight percent (e.g. about 10 wt. %) HPbCD.

In one aspect, a lyophilized pharmaceutical composition is provided comprising disclosed nanoparticles, wherein upon reconstitution of the lyophilized pharmaceutical composition at a nanoparticle concentration of about 50 mg/mL, in less than or about 100 mL of an aqueous medium, the reconstituted composition suitable for parenteral administration comprises less than 6000, such as less than 3000, microparticles of greater than or equal to 10 microns; and/or less than 600, such as less than 300, microparticles of greater than or equal to 25 microns.

The number of microparticles can be determined by means such as the USP 32 <788> by light obscuration particle count test, the USP 32 <788> by microscopic particle count test, laser diffraction, and single particle optical sensing.

In an aspect, a pharmaceutical composition suitable for parenteral use upon reconstitution is provided comprising a plurality of therapeutic particles each comprising a copolymer having a hydrophobic polymer segment and a hydrophilic polymer segment; an active agent; a sugar; and a cyclodextrin.

For example, the copolymer may be poly(lactic) acid-block-poly(ethylene)glycol copolymer. Upon reconstitution, a 100 mL aqueous sample may comprise less than 6000 particles having a size greater than or equal to 10 microns; and less than 600 particles having a size greater than or equal to 25 microns.

The step of adding a disaccharide and an ionic halide salt may comprise adding about 5 to about 15 weight percent sucrose or about 5 to about 20 weight percent trehalose (e.g., about 10 to about 20 weight percent trehalose), and about 10 to about 500 mM ionic halide salt. The ionic halide salt may be selected from sodium chloride, calcium chloride, and zinc chloride, or mixtures thereof. In an embodiment, about 1 to about 25 weight percent cyclodextrin is also added.

In another embodiment, the step of adding a disaccharide and a cyclodextrin may comprise adding about 5 to about 15 weight percent sucrose or about 5 to about 20 weight percent trehalose (e.g., about 10 to about 20 weight percent trehalose), and about 1 to about 25 weight percent cyclodextrin. In an embodiment, about 10 to about 15 weight percent cyclodextrin is added. The cyclodextrin may be selected from α-cyclodextrin, β-cyclodextrin, γ-cyclodextrin, or mixtures thereof.

In another aspect, a method of preventing substantial aggregation of particles in a pharmaceutical nanoparticle composition is provided comprising adding a sugar and a salt to the lyophilized formulation to prevent aggregation of the nanoparticles upon reconstitution. In an embodiment, a cyclodextrin is also added to the lyophilized formulation. In yet another aspect, a method of preventing substantial aggregation of particles in a pharmaceutical nanoparticle composition is provided comprising adding a sugar and a cyclodextrin to the lyophilized formulation to prevent aggregation of the nanoparticles upon reconstitution.

A contemplated lyophilized composition may have a therapeutic particle concentration of greater than about 40 mg/mL. The formulation suitable for parenteral administration may have less than about 600 particles having a size greater than 10 microns in a 10 mL dose. Lyophilizing may comprise freezing the composition at a temperature of greater than about −40° C., or e.g. less than about −30° C., forming a frozen composition; and drying the frozen composition to form the lyophilized composition. The step of drying may occur at about 50 mTorr at a temperature of about −25 to about −34° C., or about −30 to about −34° C.

Methods of Treatment

In some embodiments, targeted nanoparticles may be used to treat, alleviate, ameliorate, relieve, delay onset of, inhibit progression of, reduce severity of, and/or reduce incidence of one or more symptoms or features of a disease, disorder, and/or condition. In some embodiments, targeted nanoparticles may be used to treat solid tumors, e.g., cancer and/or cancer cells. In certain embodiments, targeted nanoparticles may be used to treat any cancer wherein PSMA is expressed on the surface of cancer cells or in the tumor neovasculature in a subject in need thereof, including the neovasculature of prostate or non-prostate solid tumors. Examples of the PSMA-related indication include, but are not limited to, prostate cancer, breast cancer, non-small cell lung cancer, colorectal carcinoma, and glioblastoma.

The term "cancer" includes pre-malignant as well as malignant cancers. Cancers include, but are not limited to, blood (e.g., chronic myelogenous leukemia, chronic myelomonocytic leukemia, Philadelphia chromosome positive acute lymphoblastic leukemia, mantle cell lymphoma), prostate, gastric cancer, colorectal cancer, skin cancer, e.g., melanomas or basal cell carcinomas, lung cancer (e.g., non-small cell lung cancer), breast cancer, cancers of the head and neck, bronchus cancer, pancreatic cancer, urinary bladder cancer, brain or central nervous system cancer, peripheral nervous system cancer, esophageal cancer, cancer of the oral cavity or pharynx, liver cancer (e.g., hepatocellular carcinoma), kidney cancer (e.g., renal cell carcinoma), testicular cancer, biliary tract cancer, small bowel or appendix cancer, gastrointestinal stromal tumor, salivary gland cancer, thyroid gland cancer, adrenal gland cancer, osteosarcoma, chondrosarcoma, cancer of hematological tissues, and the like. "Cancer cells" can be in the form of a tumor (i.e., a solid tumor), exist alone within a subject (e.g., leukemia cells), or be cell lines derived from a cancer.

Cancer can be associated with a variety of physical symptoms. Symptoms of cancer generally depend on the type and location of the tumor. For example, lung cancer can cause coughing, shortness of breath, and chest pain, while colon cancer often causes diarrhea, constipation, and blood in the stool. However, to give but a few examples, the following symptoms are often generally associated with many cancers: fever, chills, night sweats, cough, dyspnea, weight loss, loss of appetite, anorexia, nausea, vomiting, diarrhea, anemia, jaundice, hepatomegaly, hemoptysis, fatigue, malaise, cognitive dysfunction, depression, hormonal disturbances, neutropenia, pain, non-healing sores, enlarged lymph nodes, peripheral neuropathy, and sexual dysfunction.

In one aspect, a method for the treatment of cancer (e.g., leukemia) is provided. In some embodiments, the treatment of cancer comprises administering a therapeutically effective amount of inventive targeted particles to a subject in need thereof, in such amounts and for such time as is necessary to achieve the desired result. In certain embodiments, a "therapeutically effective amount" of an inventive targeted particle is that amount effective for treating, alleviating, ameliorating, relieving, delaying onset of, inhibiting progression of, reducing severity of, and/or reducing incidence of one or more symptoms or features of cancer.

In one aspect, a method for administering inventive compositions to a subject suffering from cancer (e.g., leukemia) is provided. In some embodiments, particles may be administered to a subject in such amounts and for such time as is necessary to achieve the desired result (i.e., treatment of cancer). In certain embodiments, a "therapeutically effective amount" of an inventive targeted particle is that amount effective for treating, alleviating, ameliorating, relieving, delaying onset of, inhibiting progression of, reducing severity of, and/or reducing incidence of one or more symptoms or features of cancer.

Inventive therapeutic protocols involve administering a therapeutically effective amount of an inventive targeted particle to a healthy individual (i.e., a subject who does not display any symptoms of cancer and/or who has not been diagnosed with cancer). For example, healthy individuals may be "immunized" with an inventive targeted particle prior to development of cancer and/or onset of symptoms of cancer; at risk individuals (e.g., patients who have a family history of cancer; patients carrying one or more genetic mutations associated with development of cancer; patients having a genetic polymorphism associated with development of cancer; patients infected by a virus associated with development of cancer; patients with habits and/or lifestyles associated with development of cancer; etc.) can be treated substantially contemporaneously with (e.g., within 48 hours, within 24 hours, or within 12 hours of) the onset of symptoms of cancer. Of course individuals known to have cancer may receive inventive treatment at any time.

In other embodiments, disclosed nanoparticles can be used to inhibit the growth of cancer cells, e.g., prostate cancer cells. As used herein, the term "inhibits growth of cancer cells" or "inhibiting growth of cancer cells" refers to any slowing of the rate of cancer cell proliferation and/or migration, arrest of cancer cell proliferation and/or migration, or killing of cancer cells, such that the rate of cancer cell growth is reduced in comparison with the observed or predicted rate of growth of an untreated control cancer cell. The term "inhibits growth" can also refer to a reduction in size or disappearance of a cancer cell or tumor, as well as to a reduction in its metastatic potential. Preferably, such an inhibition at the cellular level may reduce the size, deter the growth, reduce the aggressiveness, or prevent or inhibit metastasis of a cancer in a patient. Those skilled in the art can readily determine, by any of a variety of suitable indicia, whether cancer cell growth is inhibited.

Inhibition of cancer cell growth may be evidenced, for example, by arrest of cancer cells in a particular phase of the cell cycle, e.g., arrest at the G2/M phase of the cell cycle. Inhibition of cancer cell growth can also be evidenced by direct or indirect measurement of cancer cell or tumor size. In human cancer patients, such measurements generally are made using well known imaging methods such as magnetic resonance imaging, computerized axial tomography and X-rays. Cancer cell growth can also be determined indirectly, such as by determining the levels of circulating carcinoembryonic antigen, prostate specific antigen or other cancer-specific antigens that are correlated with cancer cell growth Inhibition of cancer growth is also generally correlated with prolonged survival and/or increased health and well-being of the subject.

Also provided herein are methods of administering to a patient a nanoparticle disclosed herein including an therapeutic agent, wherein, upon administration to a patient, such nanoparticles substantially reduces the volume of distribution and/or substantially reduces free $C_{max}$, as compared to administration of the agent alone (i.e., not as a disclosed nanoparticle).

U.S. Pat. No. 8,206,747, issued Jun. 26, 2012, entitled "Drug Loaded Polymeric Nanoparticles and Methods of Making and Using Same" is hereby incorporated by reference in its entirety.

EXAMPLES

The invention now being generally described, it will be more readily understood by reference to the following examples which are included merely for purposes of illustration of certain aspects and embodiments, and are not intended to limit the invention in any way.

Example 1: Exemplary Nanoparticle Preparation—Emulsion Process 1

Preparation of organic phase. To a 20 mL glass vial are added poly(lactic acid)-poly(ethylene glycol)diblock copolymer (PLA-PEG) (950 mg) and benzyl alcohol (9 g). The mixture is vortexed overnight to give a polymer-BA organic phase. Prior to formulation of the nanoparticles, 50 mg of drug are dissolved in the organic phase by vortexing.

Preparation of aqueous phase. To a 1 L bottle are added sodium cholate (SC) (4.75 g) and DI water (955.25 g). The mixture is stirred on a stir plate until dissolved. To the sodium cholate/water was added benzyl alcohol (40 g) and the mixture stirred on a stir plate until dissolved.

Formation of emulsion. The ratio of aqueous phase to organic phase is 5:1. The organic phase is poured into the aqueous phase and the mixture homogenized using a hand homogenizer for 10 seconds at room temperature to form a course emulsion. The course emulsion is fed through a high pressure homogenizer (110S) with pressure set at 46 psi on gauge for 2 discreet passes to form a nanoemulsion (fine emulsion). (Note: after $1^{st}$ pass, 5% SC was doped into the nanoemulsion to achieve final 0.5% SC).

Formation of nanoparticles. The nanoemulsion is poured into a quench (D.I. water) at less than 5° C. while stirring on stir plate to form a quenched phase. The ratio of quench to emulsion is 10:1. To the quenched phase is added Tween 80 in water (35% (w/w)) at a ratio of 100:1 Tween 80 to drug.

Concentration of nanoparticles through tangential flow filtration (TFF). The quenched phase is concentrated using TFF with 300 kDa Pall cassette (2 membrane) to form a nanoparticle concentrate of ~200 mL. The nanoparticle concentrate is diafiltered with ~20 diavolumes (4 L) of cold DI water. The volume of the diafiltered nanoparticle concentrate is reduced to a minimal volume. Cold water (100 mL) is added to the vessel and pumped through the membrane to rinse and form a slurry. The slurry (~100 mL) is collected in a glass vial.

Determination of solids concentration of unfiltered final slurry. To a tared 20 mL scintillation vial is added a volume of final slurry, which is dried under vacuum on a lyophilizer/oven. The weight of nanoparticles in the volume of dried slurry is determined. To the final slurry is added concentrated sucrose (0.666 g/g) to attain 10% sucrose.

Determination of solids concentration of 0.45 µm filtered final slurry. A portion of the final slurry sample is filtered through a 0.45 µm syringe filter before addition of sucrose. To a tared 20 mL scintillation vial is added a volume of filtered sample, which is dried under vacuum using a lyophilizer/oven. The remaining sample of unfiltered final slurry with sucrose is frozen.

Example 2: Exemplary Nanoparticle Preparation—Emulsion Process 2

Preparation of organic phase. To a first 20 mL glass vial are added poly(lactic acid)-poly(ethylene glycol)diblock copolymer (PLA-PEG) (700 mg) and ethyl acetate (16.22 g). The mixture is vortexed overnight to give a polymer-EA solution. To a second 20 mL glass vial are added 300 mg of dasatinib and about 5 g of freshly prepared 3% trifluoroacetic acid (TFA) in benzyl alcohol (BA) and the mixture vortexed overnight to give a drug-acid-BA solution. Prior to formulation of the nanoparticles, polymer-EA solution is added to the drug-acid-BA solution and the mixture vortexed to form the organic phase.

Preparation of aqueous phase. To a 1 L bottle are added sodium cholate (SC) (5 g) and DI water (955 g). The mixture is stirred on a stir plate until dissolved. To the sodium cholate/water was added benzyl alcohol (40 g) and the mixture stirred on a stir plate until dissolved.

Formation of emulsion. The ratio of aqueous phase to organic phase is 5:1. The organic phase is poured into the aqueous phase and the mixture homogenized using a hand homogenizer for 10 seconds at room temperature to form a course emulsion. The course emulsion is fed through a high pressure homogenizer (110S) with pressure set at 45 psi on gauge for 1 pass to form a nanoemulsion (fine emulsion).

Formation of nanoparticles. The nanoemulsion is poured into a quench (D.I. water) at less than 5° C. while stirring on stir plate to form a quenched phase. The ratio of quench to emulsion is 10:1. To the quenched phase is added Tween 80 in water (35% (w/w)) at a ratio of 100:1 Tween 80 to drug.

Concentration of nanoparticles through tangential flow filtration (TFF). The quenched phase is concentrated using TFF with 300 kDa Pall cassette (2 membrane) to form a nanoparticle concentrate of ~200 mL. The nanoparticle concentrate is diafiltered with ~20 diavolumes (4 L) of cold DI water. The volume of the diafiltered nanoparticle concentrate is reduced to a minimal volume. Cold water (100 mL) is added to the vessel and pumped through the membrane to rinse and form a slurry. The slurry (~100 mL) is collected in a glass vial.

Determination of solids concentration of unfiltered final slurry. To a tared 20 mL scintillation vial is added a volume of final slurry, which is dried under vacuum on a lyophilizer/oven. The weight of nanoparticles in the volume of dried slurry is determined. To the final slurry is added concentrated sucrose (0.666 g/g) to attain 10% sucrose.

Determination of solids concentration of 0.45 μm filtered final slurry. A portion of the final slurry sample is filtered through a 0.45 μm syringe filter before addition of sucrose. To a tared 20 mL scintillation vial is added a volume of filtered sample, which is dried under vacuum using a lyophilizer/oven. The remaining sample of unfiltered final slurry with sucrose is frozen.

Example 3: Formulations

Six dasatinib formulations were made, with or without acid doping. The theoretical loading and solid concentration are listed in Table 1:

TABLE 1

Formulations.

| Lot # | Description | Dasatinib Theoretical Loading | Solids Concentration |
|---|---|---|---|
| 1 | Surmodics 16-5 PLA-PEG Crude, BA only | 5% | 10% |
| 2 | Surmodics 16-5 PLA-PEG Fine, BA only | 5% | 10% |
| 3 | 47-5 PLA-PEG, BA only | 5% | 10% |

TABLE 1-continued

Formulations.

| Lot # | Description | Dasatinib Theoretical Loading | Solids Concentration |
|---|---|---|---|
| 4 | Surmodics 16-5 PLA-PEG Crude, 1% TFA, 20/80 BA/EA | 20% | 4.70% |
| 5 | Surmodics 16-5 PLA-PEG Crude, 3% TFA, 20/80 BA/EA | 30% | 4.70% |
| 6 | Surmodics 16-5 PLA-PEG Crude, 6% oleic acid, 20/80 BA/EA | 7.5% | 4.70% |

With no acid doping, 5% theoretical drug load and 10% solids are used due to low drug solubility in BA (9.45 mg/mL). With acid doping, drug solubility in the organic phase (BA containing TFA or oleic acid) is much higher, as shown in Table 2, higher drug loadings could be used. All solids percentages of acid-doped formulations are maintained at 4.7% to simulate acid doped formulations of kinase inhibitors. In addition, when acid-BA mixture was used as drug solvent, 20/80 BA/EA mixture was used as final organic phase solvent 80% (wt.) by adding polymer-EA to drug-BA solution right before formulations.

TABLE 2

Dasatinib solubility in selected solvents with or without acid doping.

| Solvents with or without acid doping | Dasatinib solubility (mg/mL, by HPLC) |
|---|---|
| BA | 9.45 |
| EA | 0.32 |
| 7.5% Water in BA | 32.76 |
| 1% TFA in BA | 56.49 |
| 2% TFA in BA | 102.87 |
| 3% TFA in BA | 140.92 |
| 3% TFA in 7.5% Water in BA | 157.16 |
| 3% Oleic Acid in BA | 16.82 |
| 6% Oleic Acid in BA | 25.18 |
| 9% Oleic Acid in BA | 29.84 |

The characterization data are compiled in Table 3. The particle sizes of the formulations were within the range of about 100-150 nm. Four lots had a particle size of 110±10 nm, two lots gave a little bit larger sizes, 137.2 nm and 143.1 nm, respectively.

Two 16/5 lots (1 & 2) and one 47/5 lot (3), without acid doping, gave a drug loading of <1%. Using 1% TFA or 6% oleic acid in BA (4 & 6) also gave a drug loading of <1%. Dasatinib had the highest solubility in 3% TFA, which allowed a much higher theoretical drug loading of 30% (5). Drug loading was improved to 2.54% for 3% TFA.

TABLE 3

Formulation characterizations.

| Lot # | Formulation | Loading % | size (nm) | Notes |
|---|---|---|---|---|
| 1 | Crude 16-5 PLA-PEG, BA only, 10% solid, 5% target load | 0.87% | 113.3 | 0.475% SC, 1@46 psi, doped with 0.35 g 5% SC to ~0.50%, 1@46 psi |
| 2 | Fine 16-5 PLA-PEG, BA only, 10% solid, 5% target load | 0.98% | 106.4 | 0.475% SC, 1@45 psi, doped with 0.37 g 5% SC to ~0.50%, 1@45 psi |

TABLE 3-continued

Formulation characterizations.

| Lot # | Formulation | Loading % | size (nm) | Notes |
|---|---|---|---|---|
| 3 | 47-5 PLA-PEG, BA only, 10% solid, 5% target load | 0.46% | 112.9 | 1.2% SC, 1@45 psi, doped with 3.73 g 5% SC to ~1.4%, 1@45 psi |
| 4 | Crude 16-5 PLA-PEG, 4.7% solid, 30% target load, 1% TFA, 20/80 BA/EA | 0.34% | 137.2 | 0.30% SC, 1@45 psi |
| 5 | Crude 16-5 PLA-PEG, 4.7% solid, 30% target load, 3% TFA, 20/80 BA/EA | 2.54% | 143.1 | 0.50% SC, 1@45 psi |
| 6 | Crude 16-5 PLA-PEG, 4.7% solid, 10% target load, 6% oleic acid, 20/80 BA/EA | 0.54% | 113.6 | 0.125% SC, 1@45 psi |

Figure 4:
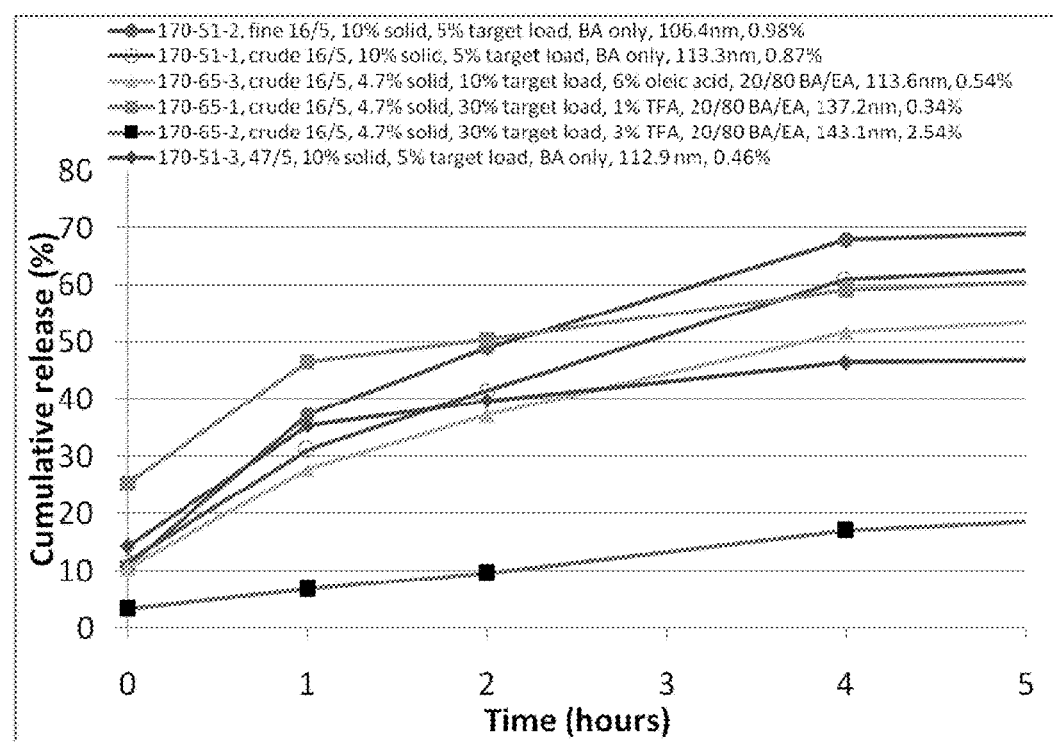
FIG. 4 depicts in vitro release profiles for various nanoparticle formulations.

The in vitro data are shown in FIG. 4 and Table 3. Three no-acid lots and one oleic acid lot gave similar burst release of about 10% of the drug. The release of drug by two no-acid 16/5 lots was the fastest with a 4 hr release of about 60% of the drug. The oleic acid lot and the no-acid 47/5 lot showed a 4 hr release of about 50%.

The 1% TFA lot (4) showed the highest burst release, with about 25.44% of the drug released. The release of drug from lot (4) occurred about as fast as no-acid 16/5 lots with a 4 hr release of 59.22% of the drug.

Among all formulations, the 3% TFA lot (5) gave the lowest burst, 3.4%. In addition, the release was significantly slower as compared to the two no-acid 16/5 lots, with a 4 hr release of 17.06% of the drug.

Release data of 24 hr and 48 hr, in Table 4, are underlined because the drug recovered at these two time points show significant degradation (data are shown in the bottom of the table in the Drug Recovery section). After 4 hr incubation at 37° C., degradation of dasatinib is observed.

TABLE 4

Results and drug recovery during in vitro experiments.

| Time (hours) | Lot 1 | Lot 2 | Lot 3 | Lot 4 | Lot 5 | Lot 6 |
|---|---|---|---|---|---|---|
| 0 | 11.62 | 10.92 | 14.28 | 25.44 | 3.40 | 10.50 |
| 1 | 31.22 | 37.22 | 35.42 | 46.64 | 6.79 | 27.84 |
| 2 | 41.52 | 49.05 | 39.71 | 50.48 | 9.58 | 37.27 |
| 4 | 60.99 | 67.90 | 46.51 | 59.22 | 17.06 | 51.71 |
| 24 | 90.89 | 88.27 | 53.11 | 86.13 | 47.72 | 84.67 |
| 48 | 83.80 | 87.14 | 37.09 | 85.14 | 55.56 | 82.00 |
| Drug recovery (%) | | | | | | |
| 1 | 99.6% | 98.5% | 99.1% | 99.1% | 100.6% | 99.5% |
| 4 | 93.2% | 88.9% | 92.3% | 89.7% | 96.3% | 94.0% |
| 24 | 45.90% | 42.94% | 56.16% | 43.77% | 64.92% | 44.27% |
| 48 | 14.19% | 12.07% | 29.65% | 13.53% | 30.60% | 13.26% |

The above formulations demonstrate the ability of 3% TFA addition to BA for both improving drug loading and slowing down drug release, as observed for the kinase inhibitor formulations.

EQUIVALENTS

Those skilled in the art will recognize, or be able to ascertain using no more than routine experimentation, many equivalents to the specific embodiments of the invention described herein. Such equivalents are intended to be encompassed by the following claims.

INCORPORATION BY REFERENCE

The entire contents of all patents, published patent applications, websites, and other references cited herein are hereby expressly incorporated herein in their entireties by reference.

What is claimed is:

1. A method of preparing a plurality of therapeutic nanoparticles, comprising:
   combining a therapeutic agent, a first polymer, and an organic acid with an organic solvent to form a first organic phase having about 1 to about 50% solids, wherein the organic acid has a $pK_a$ of less than about 3.5 at 25° C., and wherein the therapeutic agent has a solubility in a first solution consisting of the therapeutic agent, the organic solvent, and the organic acid that is at least 5 times higher as compared to a second solution consisting of the therapeutic agent and the organic solvent;
   combining the first organic phase with a first aqueous solution to form the plurality of therapeutic nanoparticles; and
   recovering the therapeutic nanoparticles by filtration,
   wherein the organic solvent comprises a solvent selected from the group consisting of ethyl acetate, benzyl alcohol, methylene chloride, chloroform, toluene, methyl ethyl ketone, dimethyl formamide, dimethyl sulfoxide, acetone, acetonitrile, acetic acid, polysorbate 80, sorbitan monostearate 80, and combinations of two or more thereof;

wherein the organic acid comprises an acid selected from the group consisting of formic acid, oxalic acid, malonic acid, maleic acid, malic acid, tartaric acid, citric acid, gluconic acid, aspartic acid, glutaminic acid, fumaric acid, itaconic acid, a halogenated carboxylic acid, triflic acid, methanesulfonic acid, benzenesulfonic acid, p-toluenesulfonic acid, and combinations thereof; and wherein the therapeutic agent is an anticancer agent.

2. The method of claim 1, wherein the therapeutic nanoparticles comprise about 1 to about 10 weight percent of the therapeutic agent.

3. The method of claim 1, wherein the method is a first method and the therapeutic nanoparticles have a therapeutic agent loading at least about 2 times higher as compared to therapeutic nanoparticles prepared by a second method, wherein the second method is identical to the first method except that the second method does not include the organic acid.

4. The method of claim 3, wherein the therapeutic nanoparticles have a therapeutic agent loading at least about 5 times higher.

5. The method of claim 1, wherein the concentration of the organic acid is between about 1 to about 10 weight percent.

6. The method of claim 1, wherein the organic acid is a halogenated carboxylic acid.

7. The method of claim 1, wherein the therapeutic nanoparticles substantially immediately release less than about 5% of the therapeutic agent when placed in a phosphate buffer solution at 37° C.

8. The method of claim 1, wherein the therapeutic nanoparticles release about 0.01 to about 25% of the therapeutic agent over about 1 hour when placed in a phosphate buffer solution at 37° C.

9. The method of claim 1, wherein the therapeutic nanoparticles release about 10 to about 45% of the therapeutic agent over about 4 hours when placed in a phosphate buffer solution at 37° C.

10. The method of claim 1, wherein the therapeutic nanoparticles have a diameter of about 60 nm to about 150 nm.

11. The method of claim 1, wherein combining the first organic phase with the first aqueous solution comprises emulsifying a second phase, formed from combining the first organic phase with the first aqueous solution, to form an emulsion phase.

12. The method of claim 11, further comprising quenching the emulsion phase to form a quenched phase.

13. The method of claim 12, further comprising adding a drug solubilizer to the quenched phase to form a solubilized phase of unencapsulated therapeutic agent.

14. The method of claim 11, wherein emulsifying the second phase comprises:
emulsifying the second phase to form a coarse emulsion, and
emulsifying the coarse emulsion to form a fine emulsion phase.

15. The method of claim 12, wherein quenching is performed at about 0° C. to about 5° C.

16. The method of claim 12, wherein the quench:emulsion ratio is about 2:1 to about 40:1.

17. The method of claim 13, wherein the drug solubilizer is selected from the group consisting of polysorbate 80, polysorbate 20, polyvinyl pyrrolidone, cyclodextran, sodium dodecyl sulfate, sodium cholate, diethylnitrosamine, sodium acetate, urea, glycerin, propylene glycol, glycofurol, poly(ethylene)glycol, bris polyoxyethylene glycol dodecyl ether, sodium benzoate, and sodium salicylate.

18. The method of claim 1, wherein filtration comprises filtering at a first temperature of about 0° C. to about 5° C.

19. The method of claim 18, further comprising filtering at a second temperature of about 20° C. to about 30° C.

20. The method of claim 13, further comprising purifying the solubilized phase before the filtration to substantially remove the organic solvent, unencapsulated therapeutic agent, and/or drug solubilizer.

21. The method of claim 1, wherein filtration comprises sterile filtration.

22. The method of claim 21, wherein the sterile filtration comprises filtering the therapeutic nanoparticles using a filtration train at a controlled rate.

23. The method of claim 1, wherein the first polymer is a diblock poly(lactic) acid-poly(ethylene)glycol copolymer.

24. The method of claim 1, wherein the organic acid is triflouroacetic acid.

* * * * *